United States Patent
Chen et al.

(10) Patent No.: US 8,268,870 B2
(45) Date of Patent: Sep. 18, 2012

(54) AMINOTETRAHYDROINDAZOLOACETIC ACIDS

(75) Inventors: Li Chen, Shanghai (CN); Fariborz Firooznia, Florham Park, NJ (US); Paul Gillespie, Westfield, NJ (US); Yun He, Shanghai (CN); Tai-An Lin, Pequannock, NJ (US); Sung-Sau So, Verona, NJ (US); HongYing Yun, Shanghai (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/324,650

(22) Filed: Dec. 13, 2011

(65) Prior Publication Data
US 2012/0095053 A1 Apr. 19, 2012

Related U.S. Application Data

(62) Division of application No. 12/497,786, filed on Jul. 6, 2009, now Pat. No. 8,124,641.

(60) Provisional application No. 61/080,703, filed on Jul. 15, 2008.

(51) Int. Cl.
*A61K 31/4439* (2006.01)
*C07D 401/12* (2006.01)

(52) U.S. Cl. .................... 514/338; 546/275.7

(58) Field of Classification Search .............. None
See application file for complete search history.

(56) References Cited

U.S. PATENT DOCUMENTS

| | | | |
|---|---|---|---|
| 3,899,529 A | 8/1975 | Witzel | |
| 4,868,331 A | 9/1989 | Niewohner et al. | |
| 4,921,998 A | 5/1990 | Niewohner et al. | |
| 2005/0014749 A1 | 1/2005 | Chen et al. | |
| 2006/0154965 A1 | 7/2006 | Harris et al. | |
| 2010/0041713 A1 | 2/2010 | Firooznia et al. | |
| 2010/0041760 A1 | 2/2010 | Blanc et al. | |
| 2010/0125058 A1 | 5/2010 | Chen et al. | |
| 2010/0125061 A1 | 5/2010 | Firooznia et al. | |

*Primary Examiner* — Kamal Saeed
(74) *Attorney, Agent, or Firm* — George W. Johnston; Dennis P. Tramaloni; Brian C. Remy

(57) ABSTRACT

The invention is concerned with the compounds of formula I:

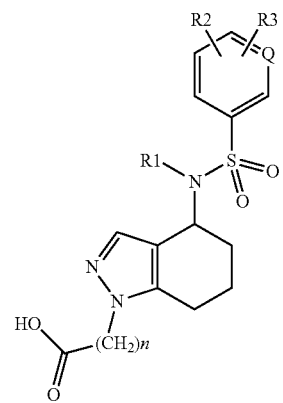

and pharmaceutically acceptable salts and esters thereof, wherein Q, R1-R3 and n are defined in the detailed description and claims. In addition, the present invention relates to methods of manufacturing and using the compounds of formula I as well as pharmaceutical compositions containing such compounds. The compounds of formula I are antagonists at the CRTH2 receptor and may be useful in treating diseases and disorders associated with that receptor such as asthma.

20 Claims, No Drawings

AMINOTETRAHYDROINDAZOLOACETIC ACIDS

PRIORITY TO RELATED APPLICATIONS

This application is a divisional application of U.S. application Ser. No. 12/497,786, filed Jul. 6, 2009, now allowed; which claims the benefit of U.S. Provisional Application No. 61/080,703, filed Jul. 15, 2008, which is hereby incorporated by reference in its entirety.

BACKGROUND OF THE INVENTION

The present invention relates to novel aminotetrahydroindazoloacetic acids, their manufacture, pharmaceutical compositions containing them and their use as CRTH2 antagonists.

Prostaglandin $D_2$ (PGD2) is the major prostanoid produced by activated mast cells and has been implicated in the pathogenesis of allergic diseases such as allergic asthma and atopic dermatitis. Chemoattractant Receptor-homologous molecule expressed on T-helper type cells (CRTH2) is one of the prostaglandin $D_2$ receptors and is expressed on the effector cells involved in allergic inflammation such as T helper type 2 (Th2) cells, eosinophils, and basophils (Nagata et al., *FEBS Lett* 459: 195-199, 1999). It has been shown to mediate PGD2-stimulated chemotaxis of Th2 cells, eosinophils, and basophils (Hirai et al., *J Exp Med* 193: 255-261, 2001). Moreover, CRTH2 mediates the respiratory burst and degranulation of eosinophils (Gervais et al., *J Allergy Clin Immunol* 108: 982-988, 2001), induces the production of proinflammatory cytokines in Th2 cells (Xue et al., *J Immunol* 175: 6531-6536), and enhances the release of histamine from basophils (Yoshimura-Uchiyama et al., *Clin Exp Allergy* 34:1283-1290). Sequence variants of the gene encoding CRTH2, which differentially influence its mRNA stability, are shown to be associated with asthma (Huang et al., *Hum Mol Genet.* 13, 2691-2697, 2004). Increased numbers of circulating T cells expressing CRTH2 have also been correlated with severity of atopic dermatitis (Cosmi et al., *Eur J Immunol* 30, 2972-2979, 2000). These findings suggest that CRTH2 plays a proinflammatory role in allergic diseases. Therefore, antagonists of CRTH2 are believed to be useful for treating disorders such as asthma, allergic inflammation, COPD, allergic rhinitis, and atopic dermatitis.

SUMMARY OF THE INVENTION

The invention is concerned with the compounds of formula I:

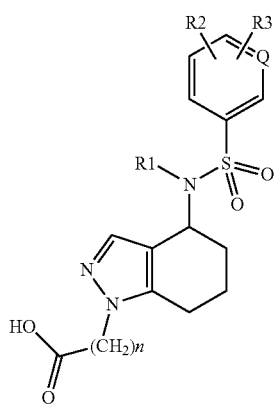

I and pharmaceutically acceptable salts and esters thereof, wherein Q, R1-R3 and n are defined in the detailed description and claims. In addition, the present invention relates to methods of manufacturing and using the compounds of formula I as well as pharmaceutical compositions containing such compounds. The compounds of formula I are antagonists at the CRTH2 receptor and may be useful in treating diseases and disorders associated with that receptor such as asthma.

DETAILED DESCRIPTION OF THE INVENTION

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the variables R1, R2, and R3 of formula I refer to moieties that are attached to the core structure of formula I by one or more chemical bonds as indicated.

In reference to a particular moiety with one or more hydrogen atoms, the term "substituted" refers to the fact that at least one of the hydrogen atoms of that moiety is replaced by another substituent or moiety. For example, the term "lower alkyl substituted by halogen" refers to the fact that one or more hydrogen atoms of a lower alkyl (as defined below) is replaced by one or more halogen atoms (i.e., trifluoromethyl, difluoromethyl, fluoromethyl, chloromethyl, etc.). Similarly, the term "lower cycloalkyl substituted by lower alkyl" refers to the fact that one or more hydrogen atoms of a lower cycloalkyl (as defined below) is replaced by one or more lower alkyls (i.e., 1-methyl-cyclopropyl, 1-ethyl-cyclopropyl, etc.)

The term "optionally substituted" refers to the fact that one or more hydrogen atoms of a moiety (with one or more hydrogen atoms) can, be but does not necessarily have to be, substituted with another substituent.

The term "alkyl" refers to an aliphatic straight-chain or branched-chain saturated hydrocarbon moiety having 1 to 20 carbon atoms. In particular embodiments the alkyl has 1 to 10 carbon atoms.

The term "lower alkyl" refers to an alkyl moiety having 1 to 7 carbon atoms. In particular embodiments the lower alkyl has 1 to 4 carbon atoms and in other particular embodiments the lower alkyl has 1 to 3 carbon atoms. Examples of lower alkyls include methyl, ethyl, propyl, isopropyl, butyl, isobutyl, sec-butyl and tert-butyl.

The term "lower cycloalkyl" refers to a saturated or partly unsaturated non-aromatic hydrocarbon ring moiety having 3 to 7 carbon atoms bonded together to form a ring structure. Examples of cycloalkyls include cyclopropyl, cyclobutyl, cyclopentyl, cyclohexyl and cycloheptyl.

The term "lower alkenyl" refers to an aliphatic straight-chain or branched-chain hydrocarbon moiety having 2 to 7 carbon atoms and having at least one carbon-to-carbon double bond. In particular embodiments the lower alkenyl has 2 to 4 carbon atoms, and in other embodiments, 2 to 3 carbon atoms. Examples of lower alkenyls include ethenyl, 1-propenyl, 2-propenyl, 1-butenyl, 2-butenyl, 3-butenyl and isobutenyl.

The term "lower alkynyl" refers to an aliphatic straight-chain or branched-chain hydrocarbon moiety having 2 to 7 carbon atoms and having at least one carbon-to-carbon triple bond. In particular embodiments the lower alkynyl has 2 to 4 carbon atoms, and in other embodiments, 2 to 3 carbon atoms. Examples of lower alkynyls include ethynyl, 1-propynyl, and 2-propynyl.

The term "lower alkoxy" refers to the moiety —O—R, wherein R is lower alkyl as defined previously. Examples of lower alkoxy moieties include methoxy, ethoxy, n-propoxy, isopropoxy, n-butoxy, isobutoxy, sec-butoxy and tert-butoxy.

The term "lower cycloalkoxy" refers to the moiety —O—R, wherein R is lower cycloalkyl as defined previously. Examples of lower cycloalkoxy moieties include cyclobutoxy and cyclopentoxy.

The term "lower alkanoyl" refers to the moiety —C(O)—R, wherein R is lower alkyl as defined previously. An example of a lower alkanoyl is acetyl.

The term "heteroatom" refers to nitrogen, oxygen, or sulfur.

The term "lower heterocycloalkyl" refers to a saturated or partly unsaturated non-aromatic ring moiety having 3 to 7 ring atoms bonded together to form a ring structure wherein one, two or three of the ring atoms is a heteroatom while the remaining ring atoms are carbon atoms. An example of a lower heterocycloalkyl is tetrahydropyran-4-yl.

The term "lower heterocycloalkyloxy" refers to the moiety R'—O—, wherein R' is a lower heterocycloalkyl as defined above. An example of a lower heterocycloalkyloxy is tetrahydropyran-4-yloxy.

The term "lower alkylsulfanyl" refers to the moiety —S—R, wherein R is lower alkyl as defined previously. Examples of lower alkylsulfanyls include methylsulfanyl and ethylsulfanyl.

The term "lower cycloalkylsulfanyl" refers to the moiety —S—R, wherein R is lower cycloalkyl as defined previously. Examples of lower cycloalkylsulfanyls include cyclopropylsulfanyl, cyclobutylsulfanyl and cyclopentylsulfanyl.

The term "lower heterocycloalkylsulfanyl" refers to the moiety —S—R, wherein R is lower heterocycloalkyl as defined previously. An example of a lower heterocycloalkylsulfanyl is pyrrolidin-1-ylsulfanyl.

The term "lower alkylsulfinyl" refers to the moiety —S(O)—R, wherein R is lower alkyl as defined previously. Examples of lower alkylsulfinyls include methylsulfinyl and ethylsulfinyl.

The term "lower cycloalkylsulfinyl" refers to the moiety —S(O)—R, wherein R is lower cycloalkyl as defined previously. Examples of lower cycloalkylsulfinyls include cyclopropylsulfinyl, cyclobutylsulfinyl and cyclopentylsulfinyl.

The term "lower heterocycloalkylsulfinyl" refers to the moiety —S(O)—R, wherein R is lower heterocycloalkyl as defined previously. An example of a lower heterocycloalkylsulfinyl is pyrrolidin-1-ylsulfinyl.

The term "lower alkylsulfonyl" refers to the moiety —S(O)$_2$—R, wherein R is lower alkyl as defined previously. Examples of lower alkylsulfonyls include methylsulfonyl and ethylsulfonyl.

The term "lower cycloalkylsulfonyl" refers to the moiety —S(O)$_2$—R, wherein R is lower cycloalkyl as defined previously. Examples of lower cycloalkylsulfonyls include cyclopropylsulfonyl, cyclobutylsulfonyl and cyclopentylsulfonyl.

The term "lower heterocycloalkylsulfonyl" refers to the moiety —S(O)$_2$—R, wherein R is lower heterocycloalkyl as defined previously. An example of a lower heterocycloalkylsulfonyl is pyrrolidin-1-ylsulfonyl.

The term "lower alkylcarbonylamino" refers to the moiety —N(H)C(O)R, wherein R is lower alkyl as defined previously. Examples of lower alkylcarbonylaminos include methylcarbonylamino and ethylcarbonylamino.

The term "lower alkylsulfonylamino" refers to the moiety —N(H)S(O)$_2$R, wherein R is lower alkyl as defined previously. Examples of lower alkylsulfonylaminos include methylsulfonylamino and ethylsulfonylamino.

The term "lower dialkylamino" refers to the moiety —N(R)(R'), wherein R and R' are lower alkyl as defined previously. An example of a lower dialkylamino is dimethylamino. The term "lower trialkylsilyl" refers to the moiety —Si(R)(R')(R") wherein R, R' and R" are lower alkyl as defined previously. An example of a lower trialkylsilyl is trimethylsilyl.

The term "halogen" refers to a moiety of fluoro, chloro, bromo or iodo.

Unless otherwise indicated, the term "hydrogen" or "hydro" refers to the moiety of a hydrogen atom (—H) and not $H_2$.

Unless otherwise indicated, the term "a compound of the formula" or "a compound of formula" or "compounds of the formula" or "compounds of formula" refers to any compound selected from the genus of compounds as defined by the formula (Including any pharmaceutically acceptable salt or ester of any such compound).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. The compounds of the present invention can also be present in the form of zwitterions. Particularly preferred pharmaceutically acceptable salts of the compounds of the present invention are the hydrochloride salts. The compounds of the present invention can also be present in the form of pharmaceutically acceptable esters (i.e., the methyl and ethyl esters of the acids of formula I to be used as prodrugs). The compounds of the present invention can also be solvated, i.e. hydrated. The solvation can be affected in the course of the manufacturing process or can take place i.e. as a consequence of hygroscopic properties of an initially anhydrous compound of formula I (hydration).

Compounds that have the same molecular formula but differ in the nature or sequence of bonding of their atoms or the arrangement of their atoms in space are termed "isomers." Isomers that differ in the arrangement of their atoms in space are termed "stereoisomers". Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

In detail, the present invention relates to the compounds of formula I:

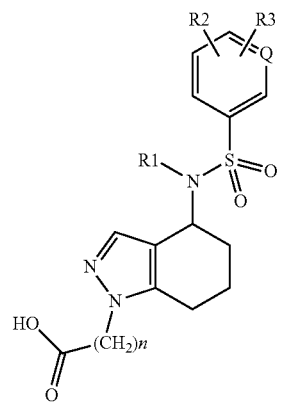

and pharmaceutically acceptable salts and esters thereof, wherein:
- Q is carbon or nitrogen;
- R1 is hydrogen or lower alkyl optionally substituted by halogen;
- R2 and R3 are bonded to the ring containing Q by substitution of a hydrogen atom of a ring carbon atom; and R2 and R3 are independently selected from the group consisting of:
  (1) hydrogen;
  (2) halogen;
  (3) —NH$_2$;
  (4) —NO$_2$;
  (5) lower alkyl optionally substituted by halogen,
  (6) lower cycloalkyl optionally substituted by lower alkyl;
  (7) lower alkenyl;
  (8) lower alkynyl;

(9) lower alkanoyl;
(10) lower alkoxy;
(11) lower cycloalkoxy;
(12) lower heterocycloalkyl;
(13) lower heterocycloalkyloxy;
(14) lower alkylsulfanyl, lower cycloalkylsulfanyl, or lower heterocycloalkylsulfanyl;
(15) lower alkylsulfinyl, lower cycloalkylsulfinyl, or lower heterocycloalkylsulfinyl;
(16) lower alkylsulfonyl, lower cycloalkylsulfonyl, or lower heterocycloalkylsulfonyl;
(17) lower alkylcarbonylamino;
(18) lower alkylsulfonylamino;
(19) lower dialkylamino; and
(20) lower trialkylsilyl;

wherein at least one of R2 or R3 is a moiety other than hydrogen that is bonded to a ring carbon atom of the ring containing Q; and n is 1 or 2.

Unless indicated otherwise, the term "Q is carbon or nitrogen" indicates: (1) when Q is carbon as depicted in formula I, the carbon is either unsubstituted by being bonded to a hydrogen (C—H) or substituted by being bonded to the moiety R2 (C—R2) or bonded to the moiety R3 (C—R3); and (2) when Q is nitrogen, the nitrogen is not bonded to either a hydrogen or R2 or R3.

Unless indicated otherwise, the term "R2 and R3 are bonded to the ring containing Q by substitution of a hydrogen atom of a ring carbon atom" refers to the fact that R2 and R3 as depicted in formula I (independently of each other) are bonded to one of the ring carbon atoms (of the aromatic ring in formula I containing Q) in place of a hydrogen atom that would otherwise be bonded to that carbon atom absent being substituted by R2 or R3; with the understanding that R2 and R3 are not simultaneously bonded to the same carbon atom.

Unless indicated otherwise, the genus of formula I and any subgenera thereof encompass all possible stereoisomers (i.e., (R)-enantiomers and (S)-enantiomers) as well as racemic and scalemic mixtures thereof. In one embodiment of the invention, the compounds of formula I are (R)-enantiomers or pharmaceutically acceptable salts or esters thereof as depicted in the following subgeneric structural formula for the (R)-enantiomers of formula I:

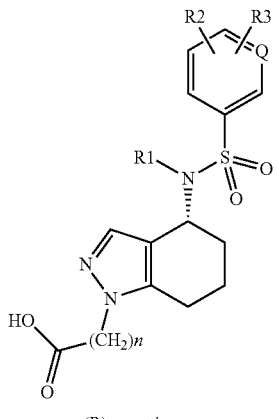

(R)-enantiomer wherein Q and R1 to R3 and n are as defined previously.

In another embodiment, the compounds of formula I are (S)-enantiomers or pharmaceutically acceptable salts or esters thereof as depicted in the following subgeneric structural formula for the (S)-enantiomers of formula I:

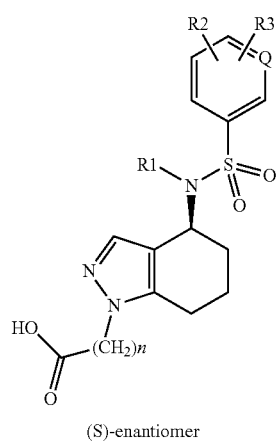

(S)-enantiomer wherein Q, R1 to R3 and n are as defined previously.

In another embodiment the present invention is directed to a composition comprising a mixture (racemic or otherwise) of the (R)-enantiomers and (S)-enantiomers of a compound of formula I.

In some embodiments the present invention is directed to the compounds of formula IA or pharmaceutically acceptable salts or esters thereof (a subgenus of formula I wherein Q represents CH) as shown below:

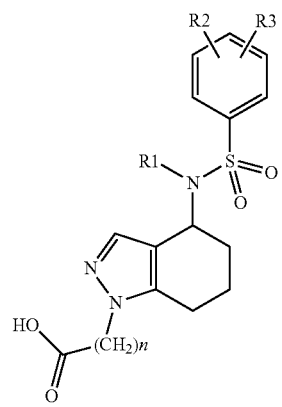

IA wherein R1 to R3 and n are as defined previously for formula I.

In other embodiments the present invention is directed to the compounds of formula IB or pharmaceutically acceptable salts or esters thereof (a subgenus of formula I wherein Q represents N) as shown below:

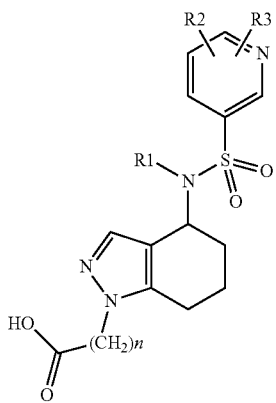

IB wherein R1 to R3 and n are as defined previously for formula I.

In one embodiment the present invention is directed to the compounds of formula I or pharmaceutically acceptable salts or esters thereof wherein R1 is hydrogen.

In another embodiment the present invention is directed to the compounds of formula I or pharmaceutically acceptable salts or esters thereof wherein R1 is lower alkyl.

In another embodiment the present invention is directed to the compounds of formula I or pharmaceutically acceptable salts or esters thereof wherein R1 is methyl.

In another embodiment the present invention is directed to the compounds of formula I or pharmaceutically acceptable salts or esters thereof wherein n is 1.

In another embodiment the present invention is directed to the compounds of formula I or pharmaceutically acceptable salts or esters thereof wherein n is 2.

In another embodiment the present invention is directed to the compounds of formula I or pharmaceutically acceptable salts or esters thereof wherein R2 and R3, independently of each other, are bonded to the ring containing Q at positions 3, 4, or 5 but not at the same position as each other, where such positions are indicated below:

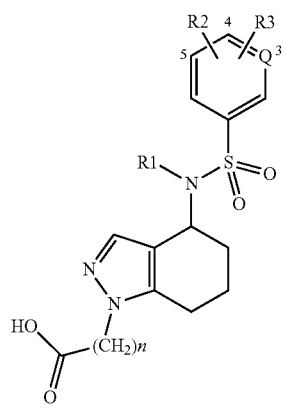

I

In another embodiment the present invention is directed to the compounds of formula I or pharmaceutically acceptable salts or esters thereof wherein R2 and R3 are independently selected from the group consisting of:
(1) halogen;
(2) lower alkyl optionally substituted by halogen,
(3) lower cycloalkyl optionally substituted by lower alkyl;
(4) lower alkenyl;
(5) lower alkynyl;
(6) lower alkanoyl;
(7) lower alkoxy;
(8) lower cycloalkoxy;
(9) lower alkylsulfonyl, lower cycloalkylsulfonyl, or lower heterocycloalkylsulfonyl;
(10) lower alkylcarbonylamino;
(11) lower alkylsulfonylamino;
(12) lower dialkylamino; and
(13) lower trialkylsilyl.

In another embodiment the present invention is directed to the compounds of formula I or pharmaceutically acceptable salts or esters thereof wherein R2 and R3 are independently selected from the group consisting of:
(1) halogen;
(2) lower alkyl optionally substituted by halogen,
(3) lower cycloalkyl optionally substituted by lower alkyl;
(4) lower alkenyl;
(5) lower alkynyl;
(6) lower alkanoyl;
(7) lower alkoxy;
(8) lower cycloalkoxy; and
(9) lower alkylsulfonyl, lower cycloalkylsulfonyl, or lower heterocycloalkylsulfonyl.

In another embodiment the present invention is directed to the compounds of formula I or pharmaceutically acceptable salts or esters thereof wherein R2 and R3 are independently selected from the group consisting of:
(1) halogen;
(2) lower alkyl optionally substituted by halogen,
(3) lower cycloalkyl optionally substituted by lower alkyl;
(4) lower alkoxy;
(5) lower cycloalkoxy; and
(6) lower alkylsulfonyl or lower cycloalkylsulfonyl.

In another embodiment the present invention is directed to the compounds of formula I or pharmaceutically acceptable salts or esters thereof wherein R2 and R3 are independently selected from the group consisting of:
(1) halogen;
(2) lower alkyl optionally substituted by halogen, and
(3) lower alkylsulfonyl or lower cycloalkylsulfonyl.

In another embodiment the present invention is directed to the compounds of formula I or pharmaceutically acceptable salts or esters thereof wherein R2 and R3 are independently selected from the group consisting of trifluoromethyl, lower alkylsulfonyl and lower cycloalkylsulfonyl.

In another embodiment the present invention is directed to the compounds of formula I or pharmaceutically acceptable salts or esters thereof wherein at least one of R2 or R3 is trifluoromethyl.

In another embodiment the present invention is directed to the compounds of formula I or pharmaceutically acceptable salts or esters thereof wherein one of R2 or R3 is trifluoromethyl and the other is selected from the group consisting of:
(1) halogen;
(2) lower alkyl optionally substituted by halogen,
(3) lower cycloalkyl optionally substituted by lower alkyl;
(4) lower alkenyl;
(5) lower alkynyl;

(6) lower alkanoyl;
(7) lower alkoxy;
(8) lower cycloalkoxy; and
(9) lower alkylsulfonyl, lower cycloalkylsulfonyl, or lower heterocycloalkylsulfonyl.

In another embodiment the present invention is directed to the compounds of formula I or pharmaceutically acceptable salts or esters thereof wherein one of R2 or R3 is bonded to position 3 when Q is carbon and the other is bonded to position 5 on the ring containing Q.

In another embodiment the present invention is directed to the compounds of formula I or pharmaceutically acceptable salts or esters thereof wherein both R2 and R3 are not hydrogen.

In another embodiment the present invention is directed to the compounds of formula I or pharmaceutically acceptable salts or esters thereof wherein R1 is methyl and n is 1.

In another embodiment the present invention is directed to the compounds of formula I or pharmaceutically acceptable salts or esters thereof which are (R)-enantiomers and wherein R1 is methyl and n is 1.

In another embodiment the present invention is directed to the compounds of formula I or pharmaceutically acceptable salts or esters thereof which are (R)-enantiomers and wherein R1 is methyl, n is 1, and wherein one of R2 or R3 is bonded to position 3 and the other is bonded to position 5 on the ring containing Q, and wherein both R2 and R3 are not hydrogen.

In another embodiment the present invention is directed to the compounds of formula I or pharmaceutically acceptable salts or esters thereof which are (R)-enantiomers and wherein R1 is methyl, n is 1, one of R2 or R3 is bonded to position 3 and the other is bonded to position 5 on the ring containing Q, and at least one of R2 or R3 is trifluoromethyl.

In a more specific embodiment the present invention is directed to a compound of formula I selected from the group consisting of:

[(R)-4-(3-bromo-5-trifluoromethyl-benzenesulfonylamino)-4,5,6,7-tetrahydro-indazol-1-yl]-acetic acid ethyl ester;
[4-(3,5-Dichloro-benzenesulfonylamino)-4,5,6,7-tetrahydro-indazol-1-yl]-acetic acid ethyl ester;
[4-(2,4-Dichloro-benzenesulfonylamino)-4,5,6,7-tetrahydro-indazol-1-yl]-acetic acid ethyl ester;
[(R)-4-(3,5-Bis-trifluoromethyl-benzenesulfonylamino)-4,5,6,7-tetrahydro-indazol-1-yl]-acetic acid ethyl ester;
[4-(4-Methyl-3-nitro-benzenesulfonylamino)-4,5,6,7-tetrahydro-indazol-1-yl]-acetic acid ethyl ester;
[4-(3,5-Dimethyl-benzenesulfonylamino)-4,5,6,7-tetrahydro-indazol-1-yl]-acetic acid ethyl ester;
[4-(3-Bromo-5-trifluoromethyl-benzenesulfonylamino)-4,5,6,7-tetrahydro-indazol-1-yl]-acetic acid ethyl ester;
[4-(4-Bromo-3-fluoro-benzenesulfonylamino)-4,5,6,7-tetrahydro-indazol-1-yl]-acetic acid ethyl ester;
[4-(4-Bromo-3-methyl-benzenesulfonylamino)-4,5,6,7-tetrahydro-indazol-1-yl]-acetic acid ethyl ester;
[4-(4-Bromo-3-trifluoromethyl-benzenesulfonylamino)-4,5,6,7-tetrahydro-indazol-1-yl]-acetic acid ethyl ester;
[4-(5-Bromo-6-chloro-pyridine-3-sulfonylamino)-4,5,6,7-tetrahydro-indazol-1-yl]-acetic acid ethyl ester;
[(R)-4-(3-Methoxy-5-trifluoromethyl-benzenesulfonylamino)-4,5,6,7-tetrahydro-indazol-1-yl]-acetic acid ethyl ester;
[4-(2,5-Bis-trifluoromethyl-benzenesulfonylamino)-4,5,6,7-tetrahydro-indazol-1-yl]-acetic acid ethyl ester;
[4-(3-Methanesulfonyl-benzenesulfonylamino)-4,5,6,7-tetrahydro-indazol-1-yl]-acetic acid ethyl ester;
[4-(4-Methoxy-3-trifluoromethyl-benzenesulfonylamino)-4,5,6,7-tetrahydro-indazol-1-yl]-acetic acid ethyl ester;
[(R)-4-(3,5-Bis-methanesulfonyl-benzenesulfonylamino)-4,5,6,7-tetrahydro-indazol-1-yl]-acetic acid ethyl ester;
[4-(3-Chloro-4-methyl-benzenesulfonylamino)-4,5,6,7-tetrahydro-indazol-1-yl]-acetic acid ethyl ester;
3-[(R)-4-(3,5-Bis-trifluoromethyl-benzenesulfonylamino)-4,5,6,7-tetrahydro-indazol-1-yl]-propionic acid methyl ester;
[(R)-4-(3-bromo-5-trifluoromethyl-benzenesulfonylamino)-4,5,6,7-tetrahydro-indazol-1-yl]-acetic acid;
[4-(3,5-Dichloro-benzenesulfonylamino)-4,5,6,7-tetrahydro-indazol-1-yl]-acetic acid;
[4-(2,4-Dichloro-benzenesulfonylamino)-4,5,6,7-tetrahydro-indazol-1-yl]-acetic acid;
[(R)-4-(3,5-Bis-trifluoromethyl-benzenesulfonylamino)-4,5,6,7-tetrahydro-indazol-1-yl]-acetic acid;
[4-(4-Methyl-3-nitro-benzenesulfonylamino)-4,5,6,7-tetrahydro-indazol-1-yl]-acetic acid;
[4-(3,5-Dimethyl-benzenesulfonylamino)-4,5,6,7-tetrahydro-indazol-1-yl]-acetic acid;
[4-(3-Bromo-5-trifluoromethyl-benzenesulfonylamino)-4,5,6,7-tetrahydro-indazol-1-yl]-acetic acid;
[4-(4-Bromo-3-fluoro-benzenesulfonylamino)-4,5,6,7-tetrahydro-indazol-1-yl]-acetic acid;
[4-(4-Bromo-3-methyl-benzenesulfonylamino)-4,5,6,7-tetrahydro-indazol-1-yl]-acetic acid;
[4-(4-Bromo-3-trifluoromethyl-benzenesulfonylamino)-4,5,6,7-tetrahydro-indazol-1-yl]-acetic acid;
[4-(5-Bromo-6-chloro-pyridine-3-sulfonylamino)-4,5,6,7-tetrahydro-indazol-1-yl]-acetic acid;
[(R)-4-(3-Methoxy-5-trifluoromethyl-benzenesulfonylamino)-4,5,6,7-tetrahydro-indazol-1-yl]-acetic acid;
[4-(2,5-Bis-trifluoromethyl-benzenesulfonylamino)-4,5,6,7-tetrahydro-indazol-1-yl]-acetic acid;
[4-(3-Methanesulfonyl-benzenesulfonylamino)-4,5,6,7-tetrahydro-indazol-1-yl]-acetic acid;
[4-(4-Methoxy-3-trifluoromethyl-benzenesulfonylamino)-4,5,6,7-tetrahydro-indazol-1-yl]-acetic acid;
[(R)-4-(3,5-Bis-methanesulfonyl-benzenesulfonylamino)-4,5,6,7-tetrahydro-indazol-1-yl]-acetic acid;
[4-(3-Chloro-4-methyl-benzenesulfonylamino)-4,5,6,7-tetrahydro-indazol-1-yl]-acetic acid;
3-[(R)-4-(3,5-Bis-trifluoromethyl-benzenesulfonylamino)-4,5,6,7-tetrahydro-indazol-1-yl]-propionic acid;
{(R)-4-[(3,5-bis-trifluoromethyl-benzenesulfonyl)-methyl-amino]-4,5,6,7-tetrahydro-indazol-1-yl}-acetic acid ethyl ester;
{(R)-4-[(4-Bromo-2-chloro-benzenesulfonyl)-methyl-amino]-4,5,6,7-tetrahydro-indazol-1-yl}-acetic acid ethyl ester;
{(R)-4-[(2-Chloro-4-trifluoromethyl-benzenesulfonyl)-methyl-amino]-4,5,6,7-tetrahydro-indazol-1-yl}-acetic acid ethyl ester;
{(R)-4-[(4-Bromo-2-fluoro-benzenesulfonyl)-methyl-amino]-4,5,6,7-tetrahydro-indazol-1-yl}-acetic acid ethyl ester;
{(R)-4-[(3-Bromo-5-trifluoromethyl-benzenesulfonyl)-methyl-amino]-4,5,6,7-tetrahydro-indazol-1-yl}-acetic acid ethyl ester;
{(R)-4-[(3,5-Dibromo-benzenesulfonyl)-methyl-amino]-4,5,6,7-tetrahydro-indazol-1-yl}-acetic acid ethyl ester;
{(R)-4-[(3,5-Di-tert-butyl-benzenesulfonyl)-methyl-amino]-4,5,6,7-tetrahydro-indazol-1-yl}-acetic acid ethyl ester;
3-{(R)-4-[(3,5-Bis-trifluoromethyl-benzenesulfonyl)-methyl-amino]-4,5,6,7-tetrahydro-indazol-1-yl}-propionic acid methyl ester;

{(R)-4-[(3,5-bis-trifluoromethyl-benzene-sulfonyl)-methyl-amino]-4,5,6,7-tetrahydro-indazol-1-yl}-acetic acid;
{(R)-4-[(4-Bromo-2-chloro-benzenesulfonyl)-methyl-amino]-4,5,6,7-tetrahydro-indazol-1-yl}-acetic acid;
{(R)-4-[(2-Chloro-4-trifluoromethyl-benzenesulfonyl)-methyl-amino]-4,5,6,7-tetrahydro-indazol-1-yl}-acetic acid;
{(R)-4-[(4-Bromo-2-fluoro-benzenesulfonyl)-methyl-amino]-4,5,6,7-tetrahydro-indazol-1-yl}-acetic acid;
{(R)-4-[(3-Bromo-5-trifluoromethyl-benzenesulfonyl)-methyl-amino]-4,5,6,7-tetrahydro-indazol-1-yl}-acetic acid;
{(R)-4-[(3,5-Dibromo-benzenesulfonyl)-methyl-amino]-4,5,6,7-tetrahydro-indazol-1-yl}-acetic acid;
{(R)-4-[(3,5-Di-tert-butyl-benzenesulfonyl)-methyl-amino]-4,5,6,7-tetrahydro-indazol-1-yl}-acetic acid;
3-{(R)-4-[(3,5-Bis-trifluoromethyl-benzenesulfonyl)-methyl-amino]-4,5,6,7-tetrahydro-indazol-1-yl}-propionic acid;
[4-(3-ethoxy-5-trifluoromethyl-benzenesulfonylamino)-4,5,6,7-tetrahydro-indazol-1-yl]-acetic acid ethyl ester;
[4-(5-Bromo-6-ethoxy-pyridine-3-sulfonylamino)-4,5,6,7-tetrahydro-indazol-1-yl]-acetic acid ethyl ester;
[4-(5-Bromo-6-cyclopentyloxy-pyridine-3-sulfonylamino)-4,5,6,7-tetrahydro-indazol-1-yl]-acetic acid ethyl ester;
[4-(3-Isopropoxy-5-trifluoromethyl-benzenesulfonylamino)-4,5,6,7-tetrahydro-indazol-1-yl]-acetic acid ethyl ester;
[4-(3-ethoxy-5-trifluoromethyl-benzenesulfonylamino)-4,5,6,7-tetrahydro-indazol-1-yl]-acetic acid;
[4-(5-Bromo-6-ethoxy-pyridine-3-sulfonylamino)-4,5,6,7-tetrahydro-indazol-1-yl]-acetic acid;
[4-(5-Bromo-6-cyclopentyloxy-pyridine-3-sulfonylamino)-4,5,6,7-tetrahydro-indazol-1-yl]-acetic acid;
[4-(3-Isopropoxy-5-trifluoromethyl-benzenesulfonylamino)-4,5,6,7-tetrahydro-indazol-1-yl]-acetic acid;
{(R)-4-[(3-chloro-4-fluoro-benzenesulfonyl)-methyl-amino]-4,5,6,7-tetrahydro-indazol-1-yl}-acetic acid ethyl ester;
{(R)-4-[(3-chloro-4-cyclopentyloxy-benzenesulfonyl)-methyl-amino]-4,5,6,7-tetrahydro-indazol-1-yl}-acetic acid ethyl ester;
{(R)-4-[(5-Bromo-6-cyclobutoxy-pyridine-3-sulfonyl)-methyl-amino]-4,5,6,7-tetrahydro-indazol-1-yl}-acetic acid ethyl ester;
{(R)-4-[(5-Bromo-6-isopropoxy-pyridine-3-sulfonyl)-methyl-amino]-4,5,6,7-tetrahydro-indazol-1-yl}-acetic acid ethyl ester;
((R)-4-{[5-Bromo-6-(tetrahydro-pyran-4-yloxy)-pyridine-3-sulfonyl]-methyl-amino}-4,5,6,7-tetrahydro-indazol-1-yl)-acetic acid ethyl ester;
{(R)-4-[(3-chloro-4-cyclopentyloxy-benzenesulfonyl)-methyl-amino]-4,5,6,7-tetrahydro-indazol-1-yl}-acetic acid;
{(R)-4-[(5-Bromo-6-cyclobutoxy-pyridine-3-sulfonyl)-methyl-amino]-4,5,6,7-tetrahydro-indazol-1-yl}-acetic acid;
{(R)-4-[(5-Bromo-6-isopropoxy-pyridine-3-sulfonyl)-methyl-amino]-4,5,6,7-tetrahydro-indazol-1-yl}-acetic acid;
((R)-4-{[5-Bromo-6-(tetrahydro-pyran-4-yloxy)-pyridine-3-sulfonyl]-methyl-amino}-4,5,6,7-tetrahydro-indazol-1-yl)-acetic acid;
[(R)-4-(3-methanesulfonyl-5-trifluoromethyl-benzenesulfonylamino)-4,5,6,7-tetrahydro-indazol-1-yl]-acetic acid ethyl ester;
[(R)-4-(3-methanesulfonyl-5-trifluoromethyl-benzene-sulfonylamino)-4,5,6,7-tetrahydro-indazol-1-yl]-acetic acid;
{(R)-4-[(3-methanesulfonyl-5-trifluoromethyl-benzenesulfonyl)-methyl-amino]-4,5,6,7-tetrahydro-indazol-1-yl}-acetic acid ethyl ester;
{(R)-4-[(3-methanesulfonyl-5-trifluoromethyl-benzenesulfonyl)-methyl-amino]-4,5,6,7-tetrahydro-indazol-1-yl}-acetic acid;
[(R)-4-(3-ethanesulfanyl-5-trifluoromethyl-benzenesulfonylamino)-4,5,6,7-tetrahydro-indazol-1-yl]-acetic acid ethyl ester;
[(R)-4-(3-Ethanesulfonyl-5-trifluoromethyl-benzenesulfonylamino)-4,5,6,7-tetrahydro-indazol-1-yl]-acetic acid ethyl ester;
[(R)-4-(3-Cyclopentanesulfonyl-5-trifluoromethyl-benzenesulfonylamino)-4,5,6,7-tetrahydro-indazol-1-yl]-acetic acid ethyl ester;
[(R)-4-(3-Ethanesulfonyl-5-trifluoromethyl-benzenesulfonylamino)-4,5,6,7-tetrahydro-indazol-1-yl]-acetic acid;
[(R)-4-(3-Cyclopentanesulfonyl-5-trifluoromethyl-benzenesulfonylamino)-4,5,6,7-tetrahydro-indazol-1-yl]-acetic acid;
{(R)-4-[(3-fluoro-5-trifluoro-methyl-benzenesulfonyl)-methyl-amino]-4,5,6,7-tetrahydro-indazol-1-yl}-acetic acid ethyl ester;
{(R)-4-[(3-Ethylsulfanyl-5-trifluoromethyl-benzene-sulfonyl)-methyl-amino]-4,5,6,7-tetrahydro-indazol-1-yl}-acetic acid ethyl ester;
{(R)-4-[(3-ethanesulfinyl-5-trifluoromethyl-benzenesulfonyl)-methyl-amino]-4,5,6,7-tetrahydro-indazol-1-yl}-acetic acid ethyl ester;
{(R)-4-[(3-ethanesulfinyl-5-trifluoromethyl-benzenesulfonyl)-methyl-amino]-4,5,6,7-tetrahydro-indazol-1-yl}-acetic acid;
{(R)-4-[(3-Cyclopentylsulfanyl-5-trifluoromethyl-benzene-sulfonyl)-methyl-amino]-4,5,6,7-tetrahydro-indazol-1-yl}-acetic acid ethyl ester;
{(R)-4-[(3-cyclopentylsulfanyl-5-trifluoromethyl-benzene-sulfonyl)-methyl-amino]-4,5,6,7-tetrahydro-indazol-1-yl}-acetic acid;
{(R)-4-[(3-ethanesulfonyl-5-trifluoromethyl-benzenesulfonyl)-methyl-amino]-4,5,6,7-tetrahydro-indazol-1-yl}-acetic acid ethyl ester;
{(R)-4-[(3-Cyclopentanesulfonyl-5-trifluoromethyl-benzenesulfonyl)-methyl-amino]-4,5,6,7-tetrahydro-indazol-1-yl}-acetic acid ethyl ester;
((R)-4-{Methyl-[3-(propane-2-sulfonyl)-5-trifluoromethyl-benzenesulfonyl]-amino}-4,5,6,7-tetrahydro-indazol-1-yl)-acetic acid ethyl ester;
((R)-4-{Methyl-[3-(2-methyl-propane-2-sulfonyl)-5-trifluoromethyl-benzenesulfonyl]-amino}-4,5,6,7-tetrahydro-indazol-1-yl)-acetic acid ethyl ester;
3-((R)-4-{Methyl-[3-(propane-2-sulfonyl)-5-trifluoromethyl-benzenesulfonyl]-amino}-4,5,6,7-tetrahydro-indazol-1-yl)-propionic acid methyl ester;
3-{(R)-4-[(3-Cyclopentanesulfonyl-5-trifluoromethyl-benzenesulfonyl)-methyl-amino]-4,5,6,7-tetrahydro-indazol-1-yl}-propionic acid ethyl ester;
3-((R)-4-{Methyl-[3-(2-methyl-propane-2-sulfonyl)-5-trifluoromethyl-benzenesulfonyl]-amino}-4,5,6,7-tetrahydro-indazol-1-yl)-propionic acid methyl ester;
{(R)-4-[(3-ethanesulfonyl-5-trifluoromethyl-benzenesulfonyl)-methyl-amino]-4,5,6,7-tetrahydro-indazol-1-yl}-acetic acid;
{(R)-4-[(3-Cyclopentanesulfonyl-5-trifluoromethyl-benzenesulfonyl)-methyl-amino]-4,5,6,7-tetrahydro-indazol-1-yl}-acetic acid;
((R)-4-{Methyl-[3-(propane-2-sulfonyl)-5-trifluoromethyl-benzenesulfonyl]-amino}-4,5,6,7-tetrahydro-indazol-1-yl)-acetic acid;

((R)-4-{Methyl-[3-(2-methyl-propane-2-sulfonyl)-5-trifluoromethyl-benzenesulfonyl]-amino}-4,5,6,7-tetrahydro-indazol-1-yl)-acetic acid;

3-((R)-4-{Methyl-[3-(propane-2-sulfonyl)-5-trifluoromethyl-benzenesulfonyl]-amino}-4,5,6,7-tetrahydro-indazol-1-yl)-propionic acid;

3-{(R)-4-[(3-Cyclopentanesulfonyl-5-trifluoromethyl-benzenesulfonyl)-methyl-amino]-4,5,6,7-tetrahydro-indazol-1-yl}-propionic acid;

3-((R)-4-{Methyl-[3-(2-methyl-propane-2-sulfonyl)-5-trifluoromethyl-benzenesulfonyl]-amino}-4,5,6,7-tetrahydro-indazol-1-yl)-propionic acid;

[(R)-4-(3-isopropenyl-5-trifluoromethyl-benzene-sulfonylamino)-4,5,6,7-tetrahydro-indazol-1-yl]acetic acid ethyl ester;

{(R)-4-[3-(1-methyl-cyclopropyl)-5-trifluoromethyl-benzenesulfonylamino]-4,5,6,7-tetrahydro-indazol-1-yl}-acetic acid ethyl ester;

{(R)-4-[3-(1-methyl-cyclopropyl)-5-trifluoromethyl-benzenesulfonyl-amino]-4,5,6,7-tetrahydro-indazol-1-yl}-acetic acid;

[4-(3-isopropyl-5-trifluoromethyl-benzenesulfonylamino)-4,5,6,7-tetrahydro-indazol-1-yl]-acetic acid ethyl ester;

[4-(3-isopropyl-5-trifluoromethyl-benzenesulfonyl-amino)-4,5,6,7-tetrahydro-indazol-1-yl]-acetic acid;

{(R)-4-[(3-isopropyl-5-trifluoromethyl-benzenesulfonyl)-methyl-amino]-4,5,6,7-tetrahydro-indazol-1-yl}-acetic acid ethyl ester;

{(R)-4-[(3-isopropyl-5-trifluoromethyl-benzenesulfonyl)-methyl-amino]-4,5,6,7-tetrahydro-indazol-1-yl}-acetic acid;

{(R)-4-[(3-isopropenyl-5-trifluoromethyl-benzenesulfonyl)-methyl-amino]-4,5,6,7-tetrahydro-indazol-1-yl}-acetic acid ethyl ester;

((R)-4-{methyl-[3-(1-methyl-cyclopropyl)-5-trifluoromethyl-benzenesulfonyl]-amino}-4,5,6,7-tetrahydro-indazol-1-yl)-acetic acid ethyl ester;

((R)-4-{methyl-[3-(1-methyl-cyclopropyl)-5-trifluoromethyl-benzenesulfonyl]-amino}-4,5,6,7-tetrahydro-indazol-1-yl)-acetic acid;

((R)-4-{methyl-[3-(1-methylene-propyl)-5-trifluoromethyl-benzenesulfonyl]-amino}-4,5,6,7-tetrahydro-indazol-1-yl)-acetic acid ethyl ester;

((R)-4-{[3-(1-ethyl-cyclopropyl)-5-trifluoromethyl-benzenesulfonyl]-methyl-amino}-4,5,6,7-tetrahydro-indazol-1-yl)-acetic acid ethyl ester;

((R)-4-{[3-(1-ethyl-cyclopropyl)-5-trifluoromethyl-benzenesulfonyl]-methyl-amino}-4,5,6,7-tetrahydro-indazol-1-yl)-acetic acid;

[4-(3-ethynyl-5-trifluoromethyl-benzenesulfonylamino)-4,5,6,7-tetrahydro-indazol-1-yl]-acetic acid ethyl ester;

[4-(3-ethynyl-5-trifluoromethyl-benzenesulfonylamino)-4,5,6,7-tetrahydro-indazol-1-yl]-acetic acid;

{(R)-4-[methyl-(3-trifluoromethyl-5-trimethylsilanyl-benzenesulfonyl)-amino]-4,5,6,7-tetrahydro-indazol-1-yl}-acetic acid ethyl ester;

{(R)-4-[methyl-(3-trifluoromethyl-5-trimethylsilanyl-benzenesulfonyl)-amino]-4,5,6,7-tetrahydro-indazol-1-yl}-acetic acid;

{(R)-4-[(3-cyclopentyl-5-trifluoromethyl-benzene-sulfonyl)-methyl-amino]-4,5,6,7-tetrahydro-indazol-1-yl}-acetic acid ethyl ester;

{(R)-4-[(3-cyclopentyl-5-trifluoromethyl-benzenesulfonyl)-methyl-amino]-4,5,6,7-tetrahydro-indazol-1-yl}-acetic acid;

{(R)-4-[(3-acetyl-5-trifluoromethyl-benzene-sulfonyl)-methyl-amino]-4,5,6,7-tetrahydro-indazol-1-yl}-acetic acid ethyl ester;

{(R)-4-[(3-acetyl-5-trifluoromethyl-benzene-sulfonyl)-methyl-amino]-4,5,6,7-tetrahydro-indazol-1-yl}-acetic acid;

((R)-4-{[3-(1,1-difluoro-ethyl)-5-trifluoro-methyl-benzenesulfonyl]-methyl-amino}-4,5,6,7-tetrahydro-indazol-1-yl)-acetic acid ethyl ester;

((R)-4-{[3-(1,1-difluoro-ethyl)-5-trifluoro-methyl-benzenesulfonyl]-methyl-amino}-4,5,6,7-tetrahydro-indazol-1-yl)-acetic acid;

[4-(3-nitro-benzenesulfonylamino)-4,5,6,7-tetrahydro-indazol-1-yl]-acetic acid ethyl ester;

[4-(3-amino-benzene-sulfonyl-amino)-4,5,6,7-tetrahydro-indazol-1-yl]-acetic acid ethyl ester;

[4-(3-acetylamino-benzenesulfonylamino)-4,5,6,7-tetrahydro-indazol-1-yl]-acetic acid ethyl ester;

[4-(3-Acetylamino-benzenesulfonylamino)-4,5,6,7-tetrahydro-indazol-1-yl]-acetic acid;

[4-(3-methanesulfonylamino-benzene-sulfonyl-amino)-4,5,6,7-tetrahydro-indazol-1-yl]-acetic acid ethyl ester;

[4-(3-methanesulfonylamino-benzene-sulfonyl-amino)-4,5,6,7-tetrahydro-indazol-1-yl]-acetic acid;

{(R)-4-[methyl-(3-pyrrolidin-1-yl-5-trifluoromethyl-benzenesulfonyl)-amino]-4,5,6,7-tetrahydro-indazol-1-yl}-acetic acid;

((R)-4-{[3-(Isopropyl-methyl-amino)-5-trifluoromethyl-benzenesulfonyl]-methyl-amino}-4,5,6,7-tetrahydro-indazol-1-yl)-acetic acid;

{(R)-4-[(3-Dimethylamino-5-trifluoromethyl-benzenesulfonyl)-methyl-amino]-4,5,6,7-tetrahydro-indazol-1-yl}-acetic acid;

{(R)-4-[(3-Diethylamino-5-trifluoromethyl-benzenesulfonyl)-methyl-amino]-4,5,6,7-tetrahydro-indazol-1-yl}-acetic acid;

[4-(3-cyclopropyl-5-trifluoromethyl-benzenesulfonylamino)-4,5,6,7-tetrahydro-indazol-1-yl]-acetic acid;

[4-(3-Methyl-5-trifluoromethyl-benzenesulfonylamino)-4,5,6,7-tetrahydro-indazol-1-yl]-acetic acid;

[4-(3-Isopropenyl-5-trifluoromethyl-benzenesulfonylamino)-4,5,6,7-tetrahydro-indazol-1-yl]-acetic acid;

{(R)-4-[(3-cyclopropyl-5-trifluoromethyl-benzene-sulfonyl)-methyl-amino]-4,5,6,7-tetrahydro-indazol-1-yl}-acetic acid methyl ester;

{(R)-4-[(3-cyclopropyl-5-trifluoromethyl-benzene-sulfonyl)-methyl-amino]-4,5,6,7-tetrahydro-indazol-1-yl}-acetic acid; and any pharmaceutically acceptable salt or ester thereof.

Another embodiment of the present invention is a compound selected from the group consisting of:

2-{(R)-4-[(3,5-bis-trifluoromethyl-benzenesulfonyl)-methyl-amino]-4,5,6,7-tetrahydro-indazol-1-yl}-2-methyl-propionic acid methyl ester;

2-{(R)-4-[(3,5-bis-trifluoromethyl-benzene-sulfonyl)-methyl-amino]-4,5,6,7-tetrahydro-indazol-1-yl}-2-methyl-propionic acid; and

[4-(3-trifluoromethyl-5-trimethylsilanylethynyl-benzenesulfonylamino)-4,5,6,7-tetrahydro-indazol-1-yl]-acetic acid ethyl ester.

General Synthesis of the Compounds of Formula I

The compounds of the present invention can be prepared by any conventional means. Suitable processes for synthesizing these compounds are provided in the examples. Generally, compounds of formula I can be prepared according to the schemes illustrated below.

Scheme 1

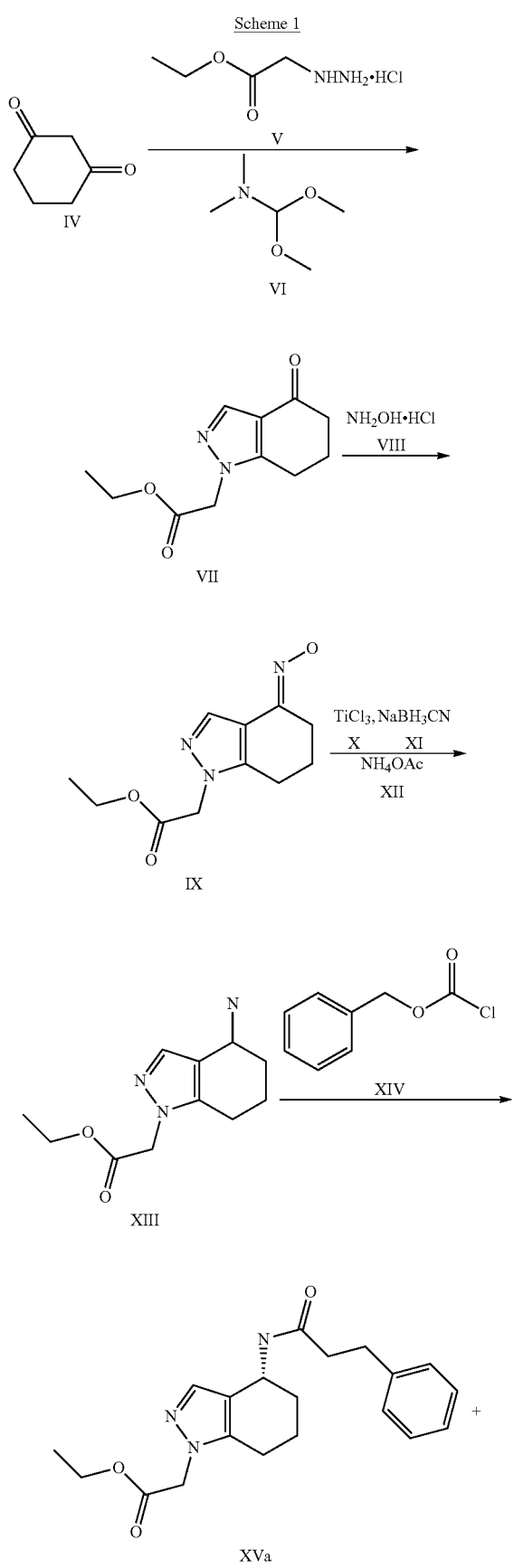

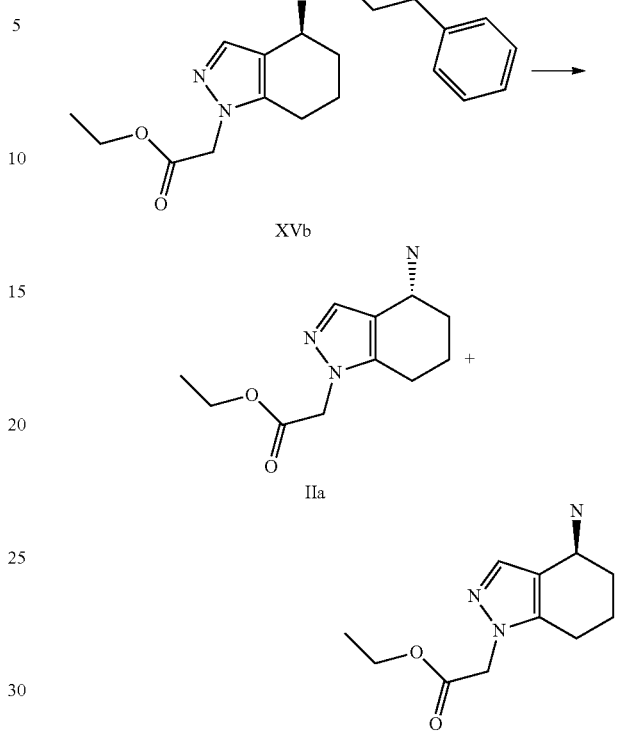

The key intermediates of formula IIa and IIb for synthesizing the compounds of interest can be prepared according to Scheme 1. In this process, a cyclization reaction involving commercially available materials, cyclohexane-1,3-dione (IV), ethyl hydrazinoacetate hydrochloride (V), and dimethoxymethyl-dimethyl-amine (VI), gives the intermediate of formula VII, which is subsequently treated with hydroxylamine hydrochloride (VIII) to produce the oxime IX. Compound IX is then converted to the corresponding amino analogue XIII, which is further functionalized to the racemic mixture of its carbamate derivatives XVa and XVb. Hydrogenolysis of either XVa or XVb (or the mixture of the two) then provides the corresponding IIa or IIb separately (or as the mixture of the two).

In the first step outlined in the Scheme 1, the intermediate VII can be prepared by treating cyclohexane-1,3-dione (IV) with an equimolar amount of ethyl hydrazinoacetate hydrochloride (V) in an inert solvent such as N,N-dimethylformamide at room temperature for about 5 minutes, followed by addition of dimethoxymethyl-dimethyl-amine (VI), and subsequently heating at 190° C. for 2 minutes under microwave irradiation (reference: Molteni, V. et al., Synthesis (2002) 1669).

Condensation of the ketone VII with hydroxylamine hydrochloride (VIII) to give the oxime IX can be achieved by heating the reaction mixture at a temperature between 70 and 90° C. (reflux temperature) for 1 to 3 hours in an alcohol solvent, such as methanol, ethanol or n-butanol. The reaction can be carried out in the presence or absence of a base such as pyridine, sodium hydroxide, or sodium acetate.

Reduction of the oxime IX to the corresponding amine XIII can be achieved by using titanium (III) chloride (X), sodium cyanoborohydride (XI), and ammonium acetate (XII). The reaction can be carried out at room temperature for several hours, under an atmosphere of an inert gas such as nitrogen or argon (reference: Leeds, J. P. et al., Synth. Comm. 18 (1988) 777).

The racemic mixture of carbamates XVa and XVb can be prepared by the condensation of the intermediate XIII with benzyl chloroformate (XIV), in the presence of an inorganic base (such as sodium carbonate, sodium bicarbonate, or sodium hydroxide) or an organic base (such as triethylamine, diisopropylethylamine or the like). The reaction solvent can be a suitable inert solvent such as tetrahydrofuran, toluene, or 1,4-dioxane when an organic base is used, or a mixture of above solvent with water when an inorganic base is used. The reaction can initially be carried out at 0° C., and then slowly allowed to warm up to room temperature during several hours. The enantiomers from the racemic mixture thus prepared can be separated at this stage to XVa and XVb using a chiral column (CHIRALPAK AS-H, 5 um, 20×250 mm) on a Gilson instrument.

Hydrogenolysis of each single enantiomer XVa or XVb (or the racemic mixture of the two) to the corresponding amine of formula IIa or IIb with retained chirality can be conveniently carried out in the presence of 10% palladium on carbon under an atmospheric pressure of hydrogen, at room temperature for several hours, in an organic solvent such as ethyl acetate, methanol, or ethanol.

Scheme 2

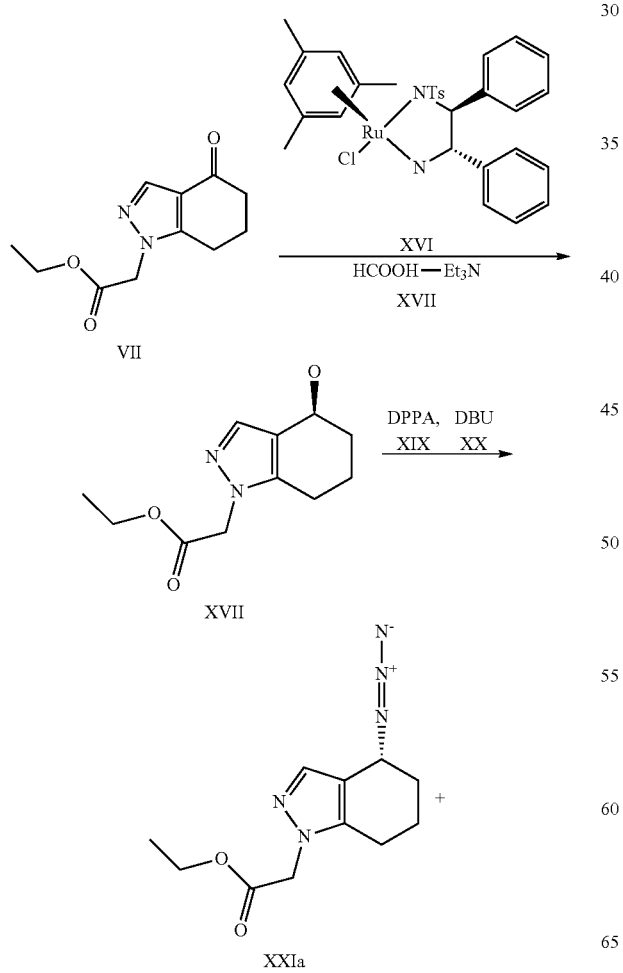

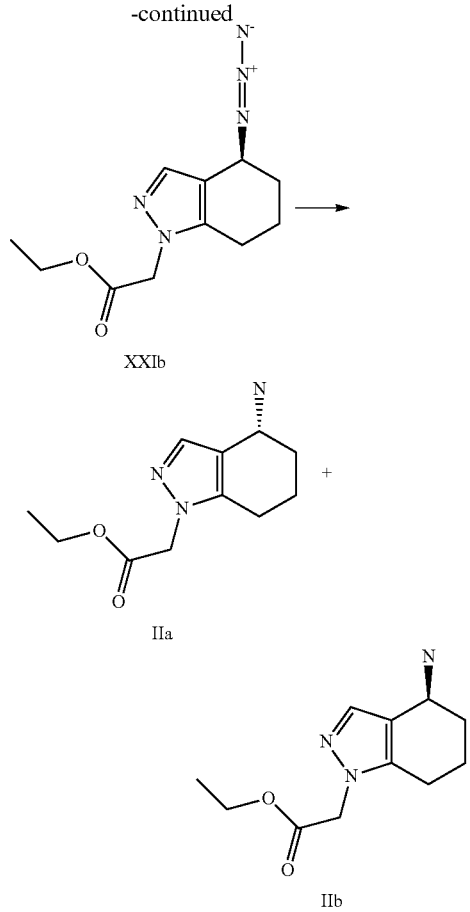

Alternatively, the key intermediate IIa or IIb can be prepared via an asymmetric synthesis approach shown in Scheme 2. This process gives predominately the enantiomer of structure IIa, which is the more preferable in this invention. Reduction of the ketone VII to the hydroxyl compound XVIII can be done enantioselectively by using the chiral catalyst of formula XVI in the presence of formic acid-triethylamine azeotropes (XVII). The hydroxyl compound XVIII is then converted to its azido analogue XXIa and XXIb with high preference for the formation of XXIa using diphenylphosphoryl azide (DPPA) (XIX) and 1,8-diazabicyclo[5,4,0]-undec-7-ene (DBU) (XX). Hydrogenation of either XXIa or XXIb gives the corresponding amine IIa or IIb with chirality intact.

Reduction of the ketone VII to the hydroxyl compound XVIII can be done enantioselectively by using a catalyst such as chloro-[(1S,2S)—N-(p-toluenesulfonyl)-1,2-diphenylethane-diamine] (mesitylene) ruthenium( ) (XVI) in formic acid-triethylamine azeotropes (molar fraction of triethylamine: 0.2857) at room temperature for several hours, and then at 45° C. for another few hours (reference: Fuji, A. et al., J. Am. Chem. Soc. 118 (1996) 2521; Wagner, K. Angew. Chem., Int. Ed. Engl. 9 (1970), 50).

Displacement of the hydroxyl group of structure XVIII to give the azido analogues XXIa and XXIb with a high selectivity for XXIa can be achieved by treating a mixture of compound XVIII and diphenylphosphoryl azide (DPPA) (XIX) with 1,8-diazabicyclo[5,4,0]-undec-7-ene (DBU) (XX) under anhydrous conditions at a temperature between −6 and 10° C. for 16 hours in an inert solvent such as toluene or N,N-dimethylformamide. The enantiomers from the mixture thus prepared can be separated by preparative HPLC with a Chiralpak IA column (reference: Ho, W-B. et al., J. Org. Chem. 65 (2000) 6743).

Hydrogenation of each enantiomer XXIa or XXIb to give the corresponding amine IIa or IIb with retained chirality can be carried out in the presence of 10% palladium on carbon under 30 psi pressure of hydrogen, at room temperature for 1 hour, in an organic solvent such as ethyl acetate, methanol, or ethanol.

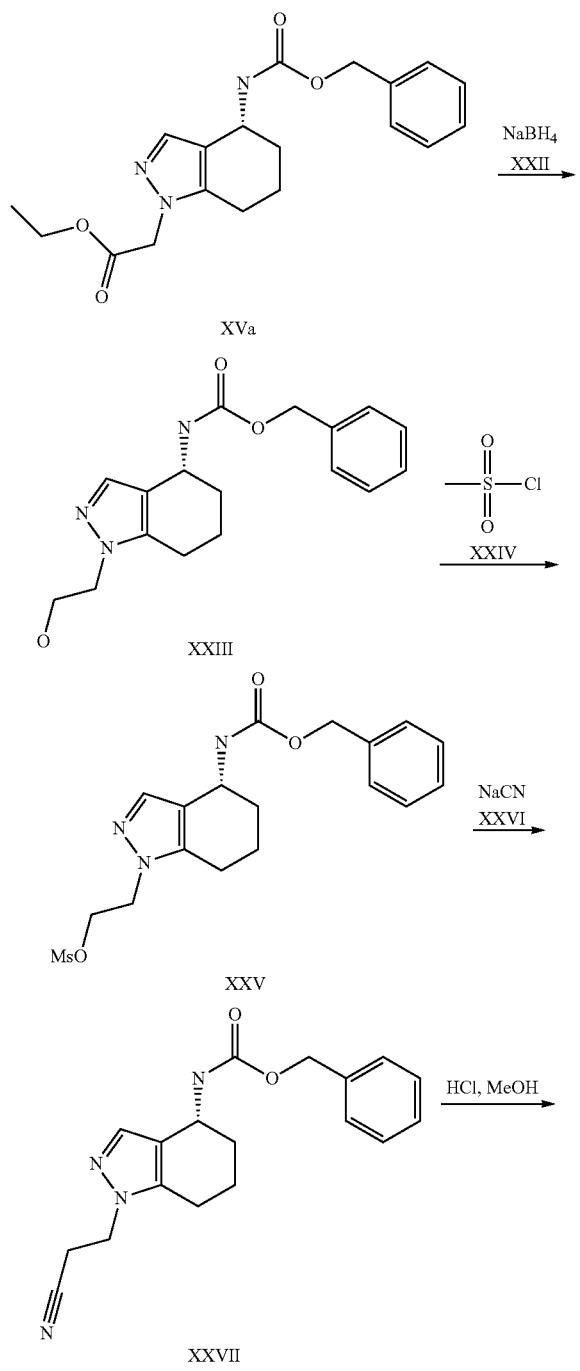

Scheme 3

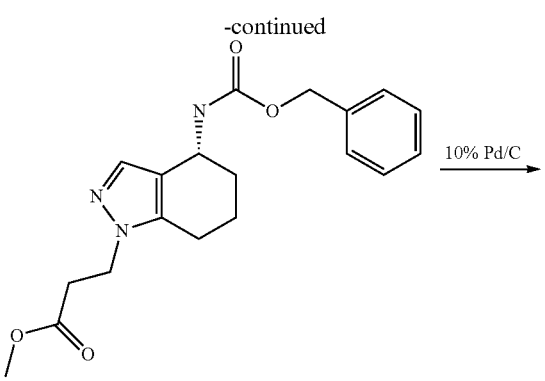

The key intermediate III can be prepared according to Scheme 3, starting with the intermediate XVa (synthesis shown in Scheme 1). Sodium borohydride reduction gives the corresponding hydroxyl compound XXIII Mesylation of the alcohol XXIII, followed by treatment with sodium cyanide (XXVI) generates the cyano derivative XXVII. Conversion of the cyanide XXVII to the methyl ester analogue XXVIII can be done easily by alcoholysis. Hydrogenolysis of the benzyl carbamate XXVIII affords compound III.

Reduction of the ester XVa to the corresponding alcohol XXIII can be easily done with a hydride-donor reagent such as sodium borohydride in an alcoholic solvent such as methanol or ethanol, at the reflux temperature of the solvent for several hours.

Reaction of the alcohol XXIII with methanesulfonyl chloride XXIV leads to the formation of the mesylate XXV. The reaction can be carried out in the presence of a base such as pyridine, triethylamine, or diisopropylethylamine in an inert solvent such as 1,4-dioxane, dichloromethane, or tetrahydrofuran at a temperature between 0° C. and room temperature for several hours.

Transformation of the mesylate XXV to the cyano derivative XXVII can be achieved by using sodium cyanide or potassium cyanide in a polar solvent such as dimethyl sulfoxide, N,N-dimethylformamide, or a mixture of ethanol and water at a temperature between 55 and 80° C. for 2 to 4 hours.

The methyl ester XXVIII can be prepared by acid catalyzed alcoholysis of the cyano derivative XXVII in a solution of hydrogen chloride in methanol at room temperature for 30 hours, or at a higher temperature (reflux temperature) for a shorter period of time.

Hydrogenolysis of the benzyl carbamate XXVIII gives the key intermediate III. The reaction can be carried out in the presence of 10% palladium on carbon under an atmospheric pressure of hydrogen in a solvent such as ethanol, ethyl acetate, or methanol at room temperature for several hours.

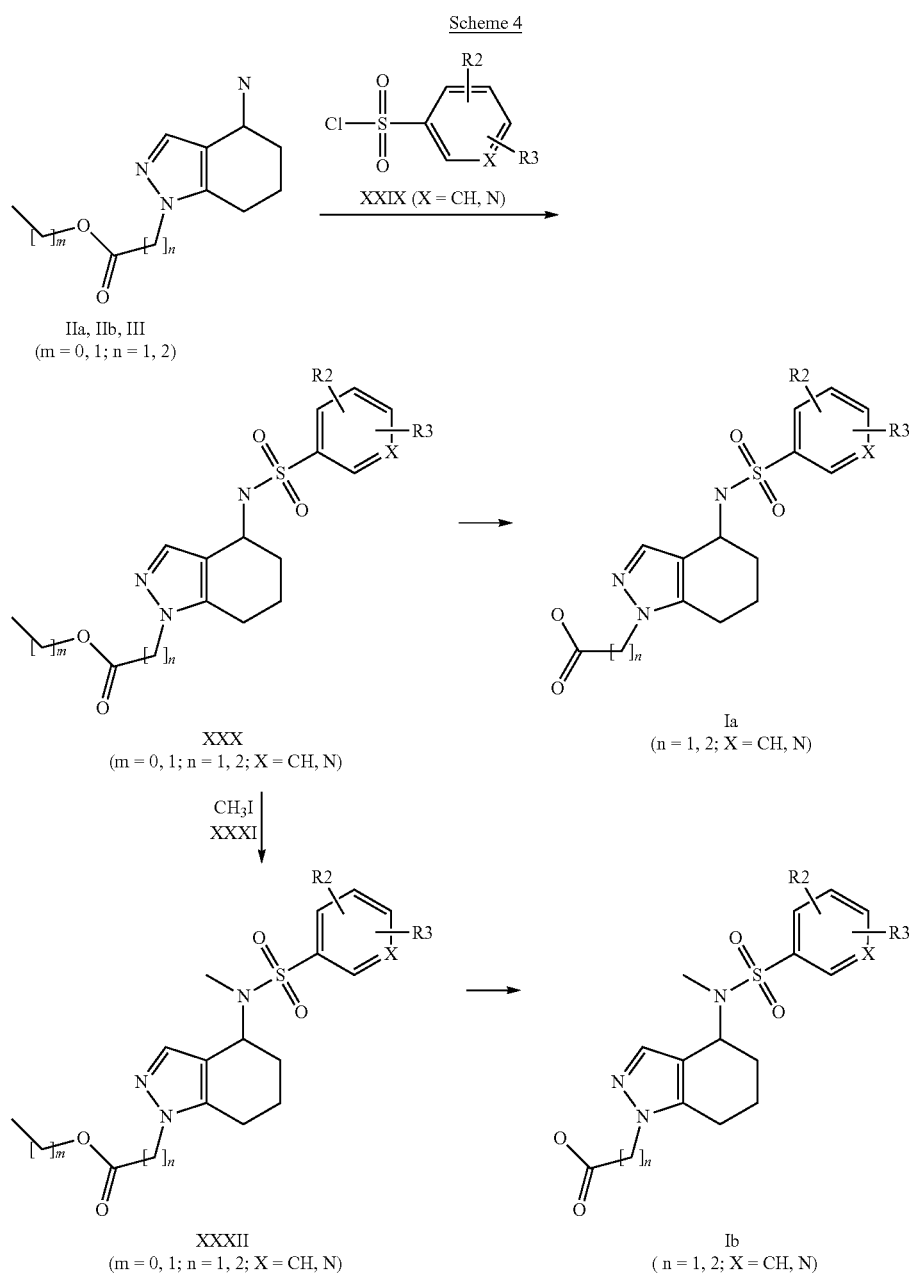

The compounds of interest of formula Ia or Ib can be prepared according to Scheme 4. Sulfonylation of the amine IIa, IIb or III leads to the corresponding sulfonamides XXX. Hydrolysis of the esters XXX gives the compounds of interest Ia. The N-methyl compounds Ib can be obtained through methylation of the intermediates XXX, followed by a hydrolysis reaction.

Sulfonylation of the amine IIa, IIb or III with sulfonyl chlorides XXIX to give the sulfonamides XXX can be easily accomplished using methods well known to someone skilled in the art. The reaction is typically carried out in the presence of a base such as triethylamine, pyridine, or dimethyl-pyridin-4-yl-amine in a suitable inert solvent such as dichloromethane, acetonitrile, 1,4-dioxane, or tetrahydrofuran and mixtures thereof, at room temperature for 16 hours.

The compounds of interest of formula Ia can be conveniently prepared via hydrolysis of the esters XXX. The reaction can be carried out in the presence of an aqueous inorganic base such as sodium hydroxide or potassium hydroxide, in an inert solvent such as 1,4-dioxane or tetrahydrofuran, at room temperature for several hours.

N-methylation of compounds XXX to produce the derivatives XXXII can be achieved by treating compounds XXX with methyl iodide (XXXI) in the presence of a weak base such as potassium carbonate or sodium carbonate, in an inert solvent such as tetrahydrofuran, acetonitrile or N,N-dimethylformamide, at 65° C. for 5 hours.

Hydrolysis of compounds XXXII gives the compounds of interest of formula Ib. The reaction can be carried out in the presence of an aqueous inorganic base such as sodium hydroxide or potassium hydroxide, in an inert solvent such as 1,4-dioxane or tetrahydrofuran, at room temperature for several hours.

Hydrolysis of compounds XXXV gives the compounds of interest of formula Ic. The reaction can be carried out in the presence of an aqueous inorganic base such as sodium hydroxide or potassium hydroxide, in an inert solvent such as tetrahydrofuran or 1,4-dioxane, at room temperature for several hours.

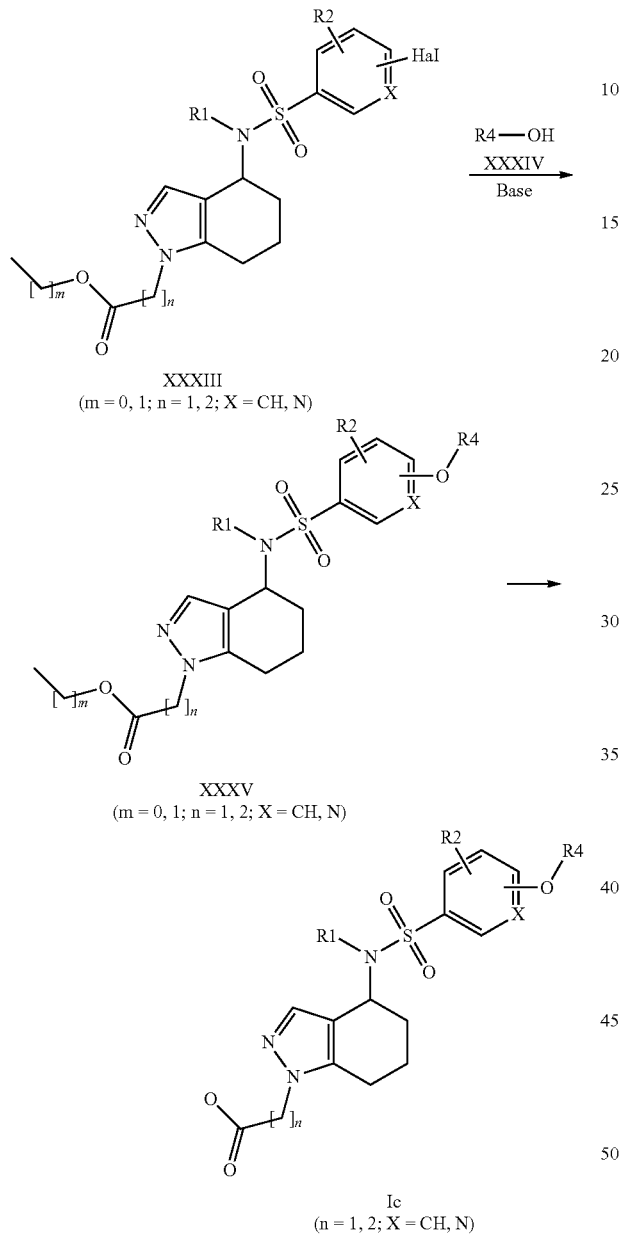

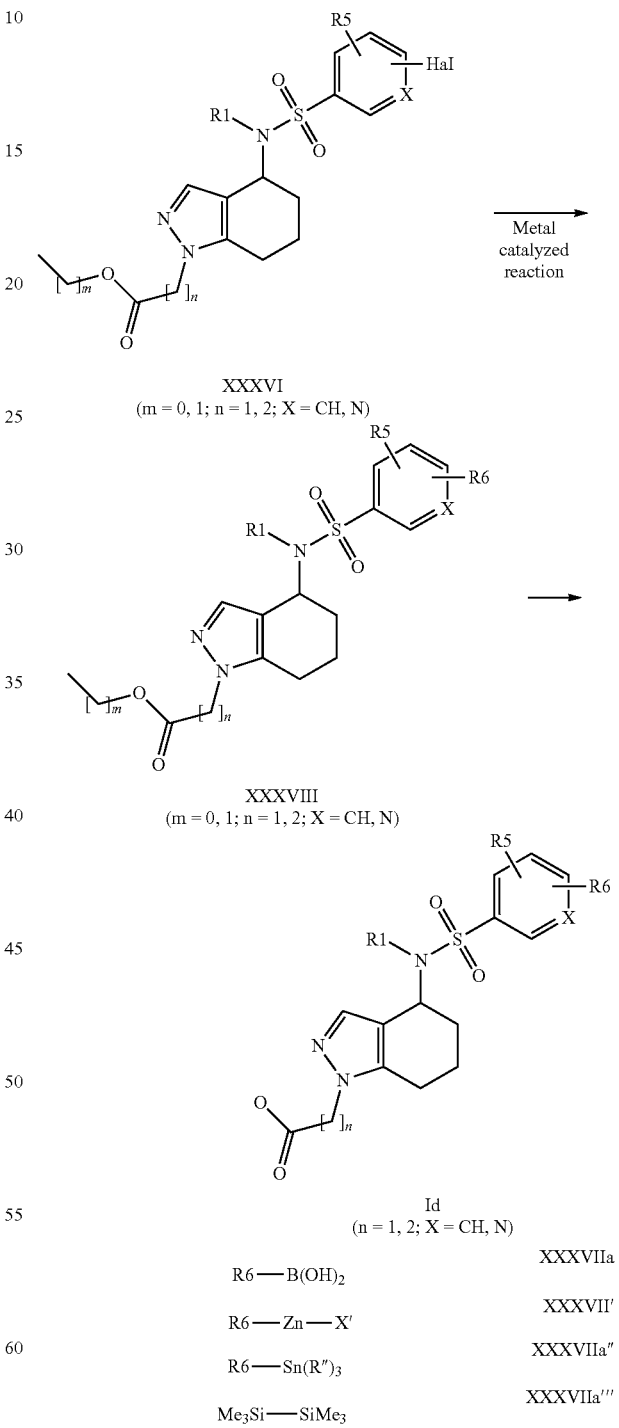

Compounds Ic, where an alkyl group (R4) is linked to the aromatic ring through an ether linkage, can be prepared according to Scheme 5, by starting with nucleophilic substitution of compounds XXXIII (prepared similarly to XXX or XXXII) with the alkyl alcohols XXXIV to give the ether XXXV, followed by a base-catalyzed hydrolysis.

Conversion of compounds XXXIII to compounds XXXV can be achieved by a nucleophilic substitution reaction with an alkyl alcohol XXXIV, which is well known to those skilled in the art, in the presence of a base such as sodium hydride or potassium carbonate, in an inert solvent such as N,N-dimethylformamide at a temperature between 100 and 150° C. for 15 to 60 minutes under microwave irradiation.

Synthesis of the compounds of interest Id is illustrated in Scheme 6. This process can give more diversified compounds of interest via transition metal (such as palladium) catalyzed coupling reactions such as Suzuki coupling, Negishi coupling, Stille coupling, or catalytic silylation. In this sequence, palladium catalyzed reaction of the aryl halide compounds XXXVI (prepared similar to compounds XXX, or XXXII) with the appropriate reactants XXXVII (boronic acids, organotin, organozinc, hexamethyldisilane), followed by hydrolysis can afford the compounds of interest Id.

In the first step of this sequence, various metal catalyzed coupling reactions, which are well know to the one skilled in the art, can be used to diversify the substituents on the aromatic sulfonamide ring. For example, Suzuki coupling reactions of the alkyl boronic acids XXXVIIa with the aryl halide compounds XXXVI to give compounds XXXVIII can be carried out in the presence of a palladium catalyst such as tetrakis(triphenylphosphine)palladium(0) $(Pd(PPh_3)_4)$, or [1,1'-bis(diphenylphosphino)ferrocene]dichloropalladium (II) $(PdCl_2(dppf))$, and a base such as potassium tert-butoxide, sodium carbonate, or sodium hydroxide, in a suitable solvent such as N,N-dimethylformamide, dimethyl sulfoxide, toluene, tetrahydrofuran, water or mixtures thereof, at a temperature between 130 and 180° C. for 15 to 30 minutes under microwave irradiation. Alternatively, the reactions can be carried out without the use of a microwave at a heated temperature such as 130° C. for a longer reaction time.

Compounds XXXVIII can also be prepared via Negishi coupling reactions, which involve the aryl halides XXXVI and the organozinc compounds XXXVIIa' and a nickel or palladium catalyst. Typically, the catalysts are tris(dibenzylideneacetone)dipalladium(0) $(Pd_2(dba)_3)$, tetrakis(triphenylphosphine)palladium(0) $(Pd(PPh_3)_4)$, palladium acetate $(Pd(OAc)_2)$, bis(triphenylphosphine)dichloronickel $(NiCl_2(PPh_3)_2)$. Ligands such as triphenylphosphine, 1,2-bis(diphenylphosphino)ethane, tris(tert-butyl)phosphine are also sometimes needed. The reactions can be carried out in a suitable solvent such as tetrahydrofuran, N,N-dimethylformamide, acetyldimethylamine, or toluene at a temperature between 0° C. and reflux temperature for several hours (reference: Wooten, A. et al., J. Am. Chem. Soc. 128 (2006) 4624).

Alternatively, Stille coupling reactions of the aryl halides XXXVI with the organotin derivatives XXXVIIa" also give compounds XXXVIII. The reaction is typically carried out in the presence of a palladium catalyst such as tris(dibenzylideneacetone)dipalladium(0) $(Pd_2(dba)_3)$, tetrakis(triphenylphosphine)palladium(0) $(Pd(PPh_3)_4)$ in a suitable solvent such as N,N-dimethylformamide, toluene, 1,4-dioxane, or hexamethylphosphoramide at a temperature between room temperature and 100° C. (reference: Sturino, C. F. et al., J. Med. Chem., 50 (2007) 794).

Silylation of the aryl halide compounds XXXVI can be done by treating compounds XXXVI with hexamethyldisilane XXXVIIa''' in the presence of a palladium catalyst such as tris(dibenzylideneacetone)dipalladium(0) $(Pd_2(dba)_3)$ in combination with a phosphine such as 2-(di-t-butylphosphino)biphenyl $(P(t-Bu)_2Ph_2)$, or diphenyl-2'-pyridyl phosphine $(PPh_2Py)$ and an inorganic base such as potassium carbonate, or potassium fluoride, in a polar solvent such as 1,3-dimethyl-3,4,5,6-tetrahydro-2(1H)-pyrimidinone (DMPU), hexamethylphosphoramide (HMPA), or N,N-dimethylformamide at 100° C. for several hours (Gooßen, L. J. et al. Synlett (2000) 1801).

Hydrolysis of compounds XXXVIII gives the compounds of interest of formula Id. The reaction can be carried out in the presence of an aqueous inorganic base such as sodium hydroxide, or potassium hydroxide, in an inert solvent such as 1,4-dioxane or tetrahydrofuran, at room temperature for several hours.

Scheme 7

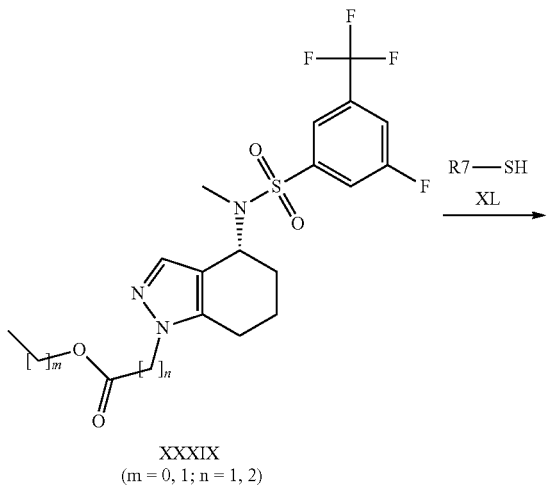

XXXIX
(m = 0, 1; n = 1, 2)

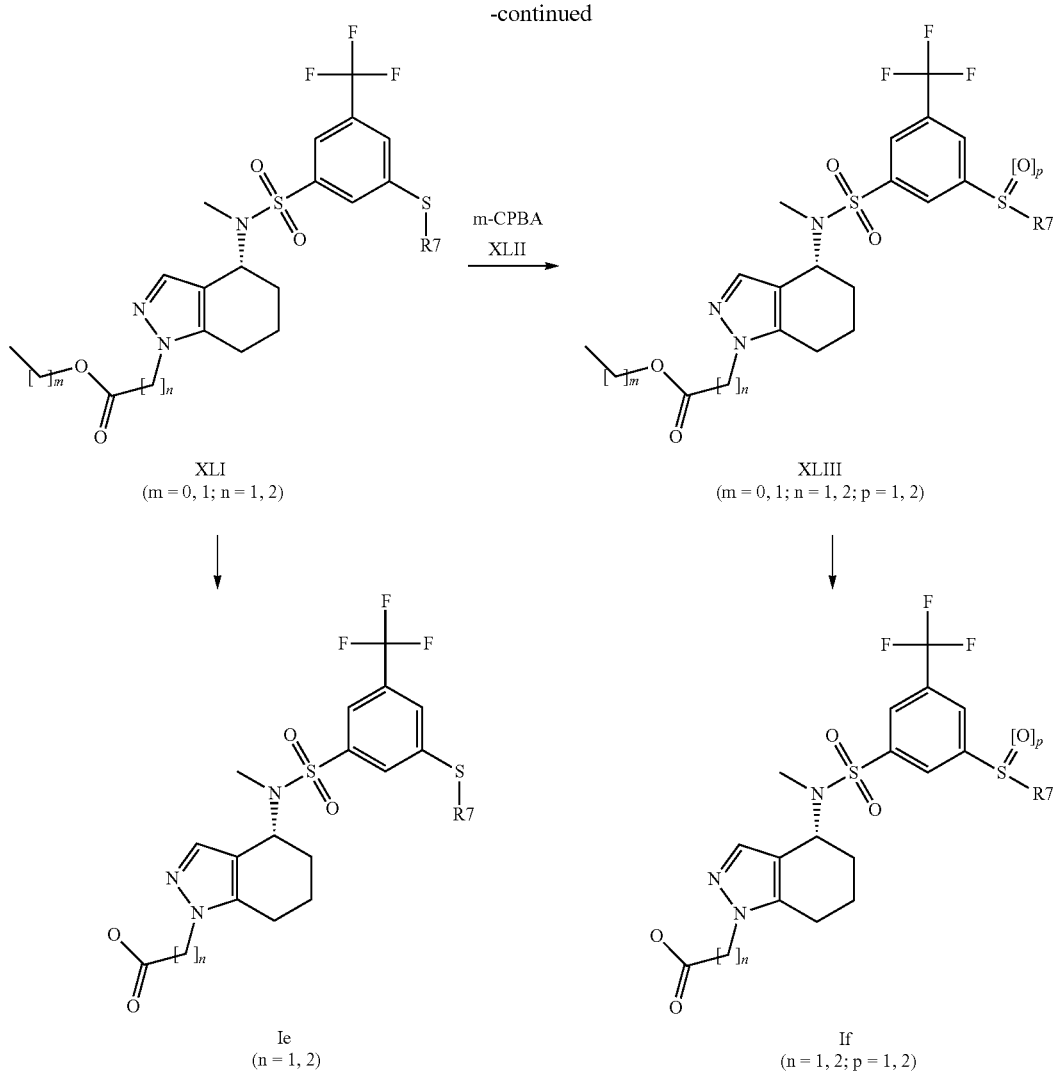

The compounds of interest of structure Ie and If, are designated in Scheme 7. Compounds Ie, where there is an alkyl sulfanyl group on the aromatic ring can be prepared by nucleophilic substitution of the fluoro-substituted compounds XXXIX (which may be prepared using the reactions described above for the preparation of compounds XXX or XXXII) with the lower alkyl thiols XL, followed by a hydrolysis reaction. Compounds If, where there is an alkyl sulfinyl group or an alkyl sulfonyl group on the aromatic ring, can be prepared by oxidation of the sulfanyl compounds XLI to the corresponding sulfoxides or sulfones, followed by a hydrolysis reaction.

Nucleophilic substitution of the fluoro-substituted compounds XXXIX with the lower alkyl thiols XL to give the 3-alkylsulfanyl analogues XLI can be done in the presence of a base, such as potassium carbonate, cesium carbonate, potassium hydroxide, sodium acetate, or triethylamine, in a solvent such as N,N-dimethylformamide, dimethyl sulfoxide, ethanol, water or mixtures thereof, at a temperature between 100 and 150° C. for about 30 to 60 minutes under microwave irradiation. Alternatively, the reaction can be also carried out without the use of a microwave at a moderately elevated temperature for a longer period of time.

Hydrolysis of compounds XLI gives the compounds of interest of formula Ie. The reaction can be carried out in the presence of an aqueous inorganic base such as sodium hydroxide, or potassium hydroxide in an inert solvent such as 1,4-dioxane or tetrahydrofuran at room temperature for several hours.

Oxidation of the sulfanyl compounds XLI to the sulfinyl or sulfonyl analogues XLIII can be achieved using an oxidant such as hydrogen peroxide or m-chloroperoxybenzoic acid (m-CPBA) (XLII), in an inert solvent such as dichloromethane or dichloroethane (or an aqueous solution if hydrogen peroxide is used), at a temperature between 0° C. and room temperature for several hours.

Hydrolysis of compounds XLIII gives the compounds of interest of formula If. The reaction can be carried out in the presence of an aqueous inorganic base such as sodium hydroxide or potassium hydroxide, in an inert solvent such as 1,4-dioxane or tetrahydrofuran, at room temperature for several hours.

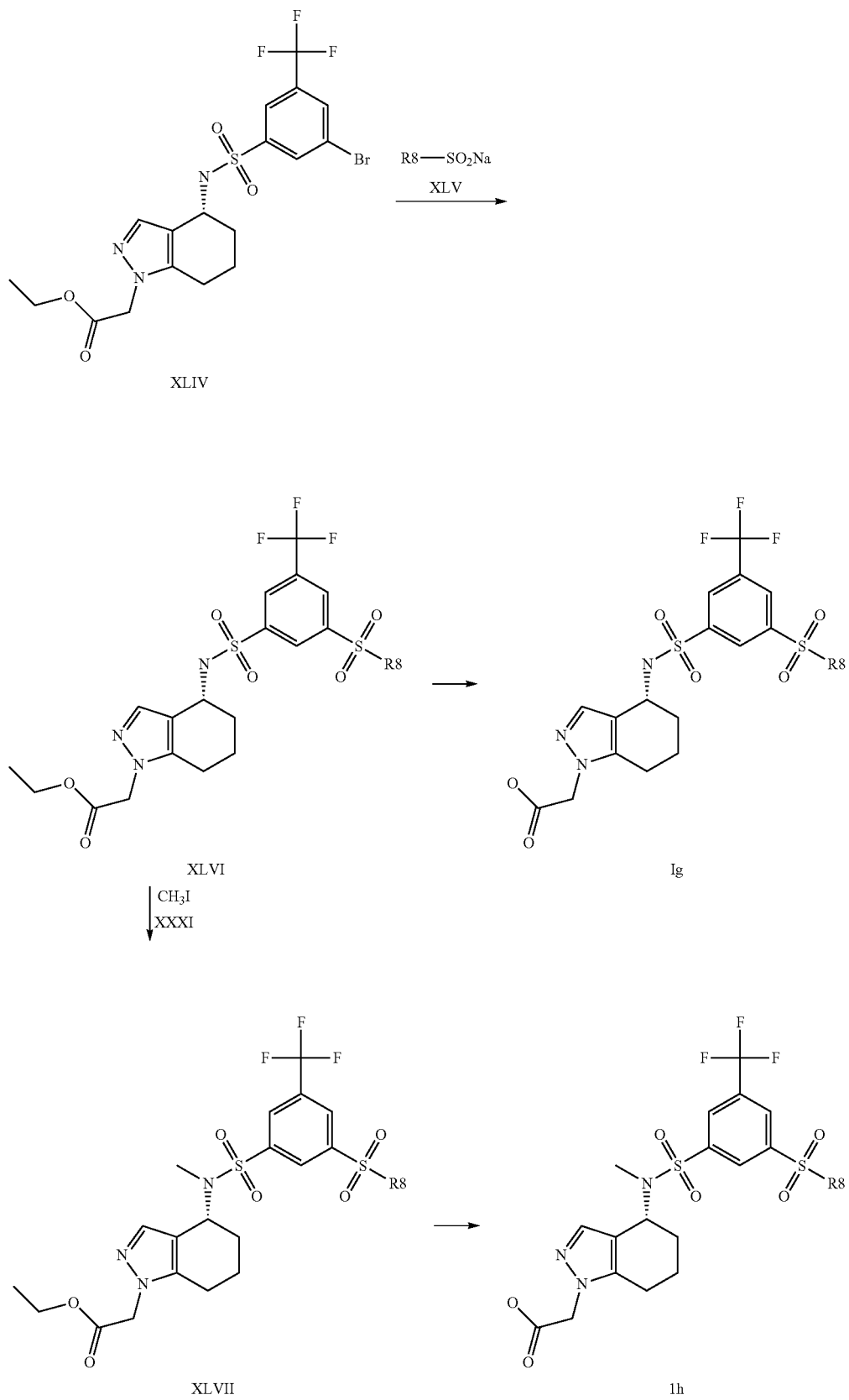

Alternatively, compounds Ig and Ih can be prepared, according to Scheme 8. Compound Ig can be obtained by substitution of the 3-bromo compounds XLIV with commercially available sulfinic acid sodium salts (XLV), followed by base-catalyzed hydrolysis. The N-methyl compounds Ih can be obtained through methylation of the intermediates XLVI, followed by a hydrolysis reaction.

In this process, the intermediate sulfonyl compounds XLVI can be formed via a copper (I) iodide catalyzed reaction of the bromo derivative XLIV with methanesulfinic acid sodium salts (XLV). The reaction can be carried out in the presence of catalysts copper(I) iodide and L-proline sodium salt in a polar solvent such as N,N-dimethylformamide, 1-methylpyrrolidine, or 1,4-dioxane at a temperature of 150° C. for 30 minutes under microwave irradiation (Zhu, W. et al., J. Org. Chem. 70 (2005) 2696).

Hydrolysis of compounds XLVI gives the compounds of interest of formula Ig. The reaction can be carried out in the presence of an aqueous inorganic base such as sodium hydroxide or potassium hydroxide, in an inert solvent such as 1,4-dioxane or tetrahydrofuran, at room temperature for several hours.

N-methylation of compounds XLVI to produce the derivatives XLVII can be achieved by treating compounds XLVI with methyl iodide (XXXI) in the presence of a weak base such as potassium carbonate, or sodium carbonate in an inert solvent such as acetonitrile, dimethylformamide, or tetrahydrofuran at 65° C. for 5 hours.

Hydrolysis of compounds XLVII gives the compounds of interest of formula Ih. The reaction can be carried out in the presence of an aqueous inorganic base such as sodium hydroxide or potassium hydroxide, in an inert solvent such as 1,4-dioxane, or tetrahydrofuran at room temperature for several hours.

Scheme 9

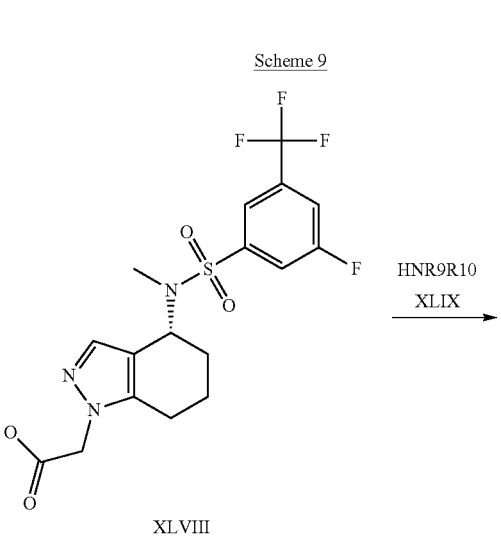

XLVIII

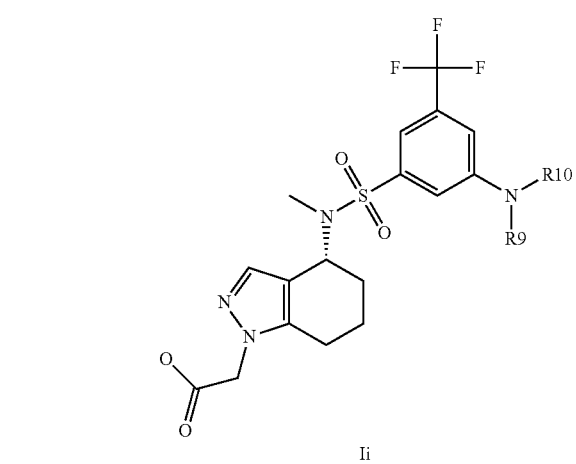

Ii

The compounds of structure Ii, bearing an amino group on the aromatic ring, can be prepared, according to Scheme 9, by nucleophilic substitution of the fluoro-substituted derivative XLVIII with primary or secondary amines XLIX. The reaction can be easily carried out in a polar solvent such as dimethyl sulfoxide or N,N-dimethylformamide, at a high temperature between 150 and 180° C. for 50 to 60 minutes under microwave irradiation.

Scheme 10
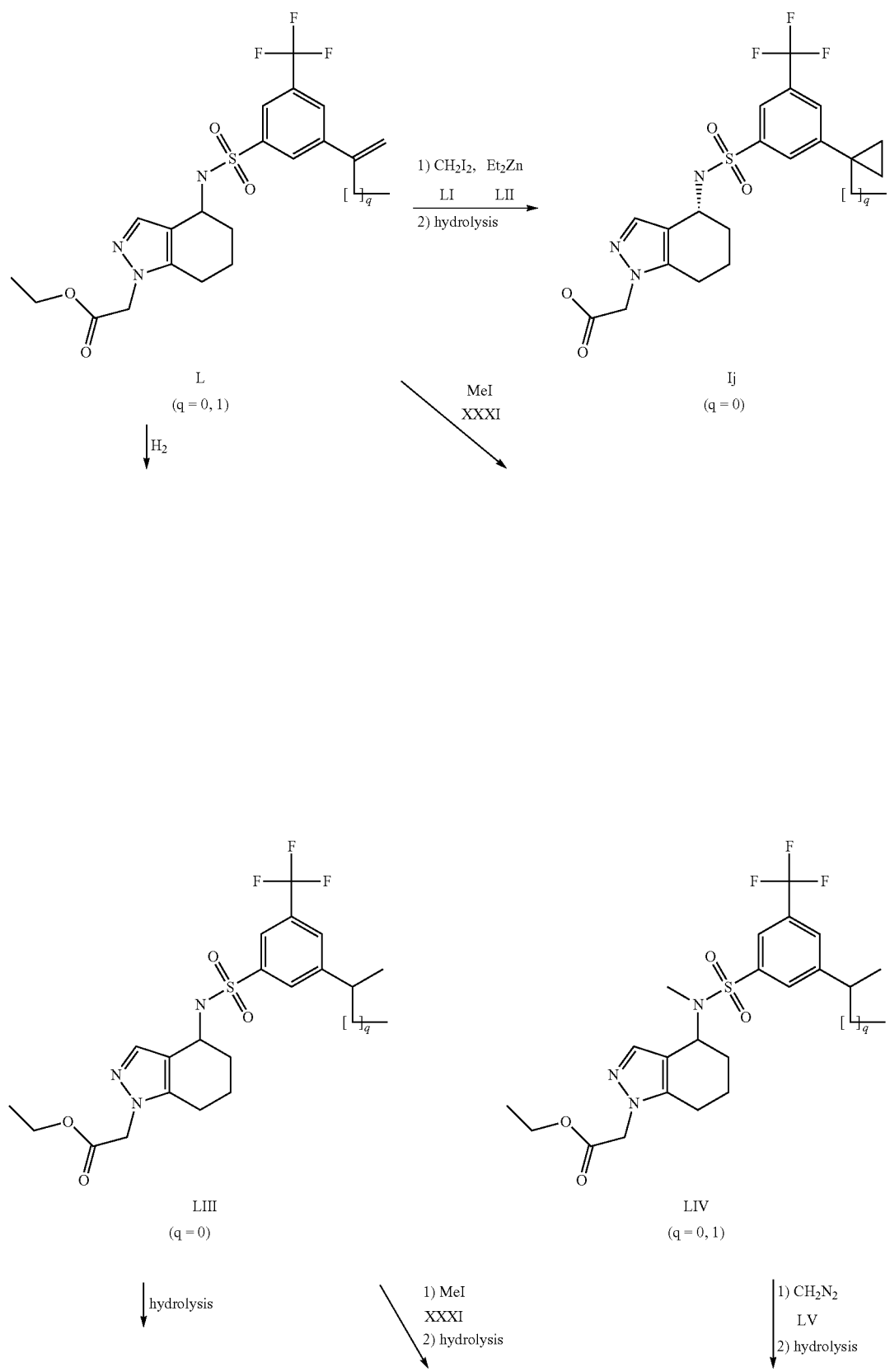

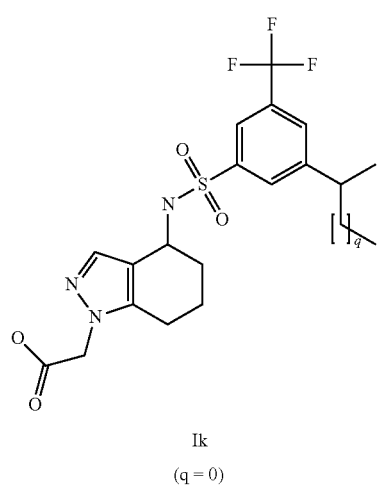
Ik
(q = 0)

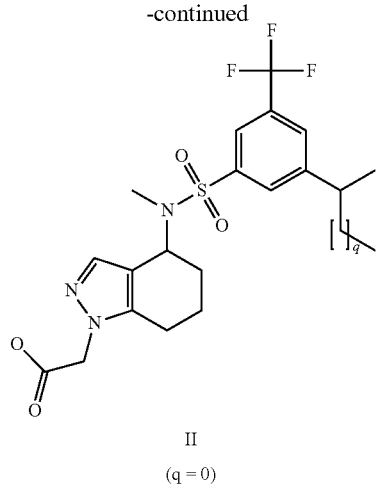
Il
(q = 0)

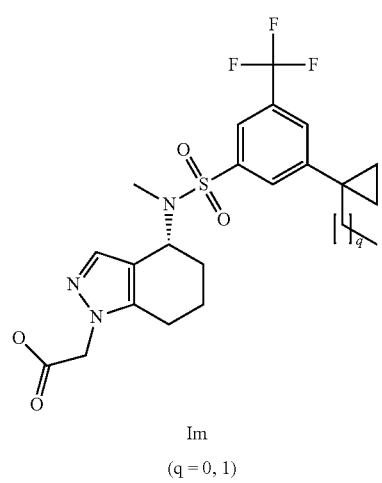
Im
(q = 0, 1)

The preparation of compounds Ij-Im is shown in Scheme 10. Starting with compounds L, which can be obtained as outlined in Scheme 6, the cyclopropyl derivatives Ij can be formed by treating the olefins L with methylene diiodide (LI) and diethylzinc (LII) followed by a hydrolysis reaction. Hydrogenation of compounds L, followed by an ester hydrolysis reaction provides compounds Ik. N-methylation of compounds LIII with methyl iodide XXXI, followed by hydrolysis gives compounds Il. N-methylation of the olefins L generates the intermediates LIV. Cyclopropyl derivatives Im can be obtained by treating the intermediates LIV with diazomethane (LV), followed by an ester hydrolysis reaction.

Cyclopropyl ring formation can be achieved by treating the olefins L with methylene diiodide (LI) and diethylzinc (LII) in an inert solvent such as toluene, tetrahydrofuran, or methylene chloride at a temperature between 0° C. and room temperature for several hours (reference: Lacasse, M. C. et al., J. Am. Chem. Soc. 127 (2005) 12440). The final compounds Ij can be obtained through base-catalyzed hydrolysis in the presence of an aqueous inorganic base such as sodium hydroxide or potassium hydroxide, in an inert solvent such as 1,4-dioxane or tetrahydrofuran, at room temperature for several hours.

Conversion of the olefins L to the corresponding saturated intermediates LIII via hydrogenation can be carried out in the presence of 10% palladium on carbon under 30 psi pressure of hydrogen in a solvent such as ethanol, ethyl acetate, or methanol at room temperature for several hours. The final compounds Ik can be obtained through base-catalyzed hydrolysis in the presence of an aqueous inorganic base such as sodium hydroxide or potassium hydroxide, in an inert solvent such as 1,4-dioxane or tetrahydrofuran, at room temperature for several hours.

N-methylation of compound LIII with methyl iodide (XXXI) can be achieved in the presence of a weak base such as potassium carbonate or sodium carbonate, in an inert solvent such as N,N-dimethylformamide, acetonitrile, or tetrahydrofuran at 65° C. for several hours. The final compounds Il can be obtained through base-catalyzed hydrolysis in the presence of an aqueous inorganic base such as sodium hydroxide or potassium hydroxide, in an inert solvent such as 1,4-dioxane or tetrahydrofuran, at room temperature for several hours.

In the same fashion, the N-methyl compounds LIV can be obtained from compounds L by using methyl iodide (XXXI) in the presence of a weak base such as potassium carbonate, or sodium carbonate in an inert solvent such as N,N-dimethylformamide, acetonitrile, or tetrahydrofuran at 65° C. for 5 hours. Transformation of the double bond compounds LIV to the corresponding cyclopropyl ring derivatives can be done by treating compound LIV with diazomethane (LV) in the presence of a palladium catalyst such as palladium acetate, palladium(II)acetylacetone, or palladium dichloride bis(benzonitrile) in a solvent such as dichloromethane, diethyl ether, tetrahydrofuran, or the mixture of thereof at a temperature between 0° C. and room temperature for several hours (reference: Staas, D. D. et al. Bioorg. Med. Chem. 14 (2006) 6900). Further hydrolysis of the prepared cyclopropyl compound gives the final compounds Im. The reaction can be carried out in the presence of an aqueous inorganic base such as sodium hydroxide or potassium hydroxide, in an inert solvent such as 1,4-dioxane or tetrahydrofuran, at room temperature for several hours.

Scheme 11

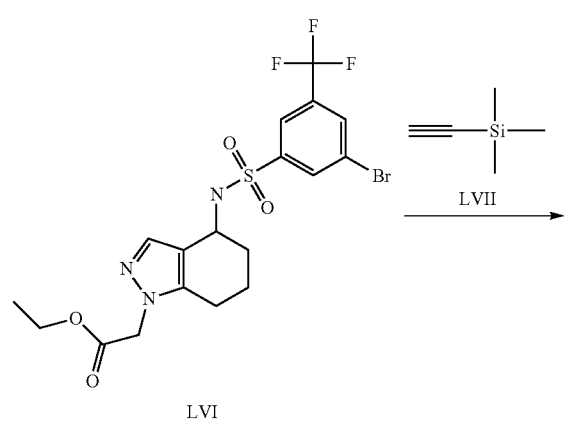

LVI

-continued

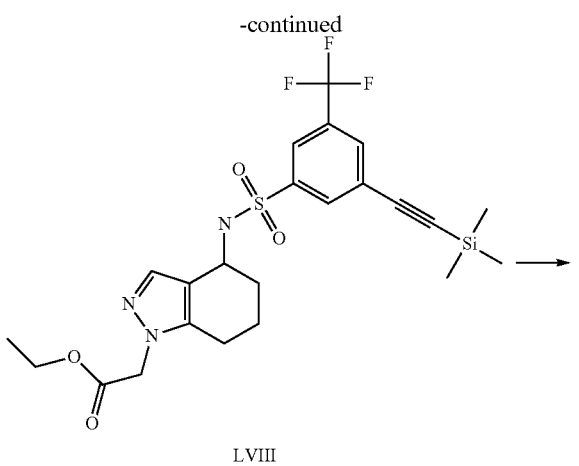

LVIII

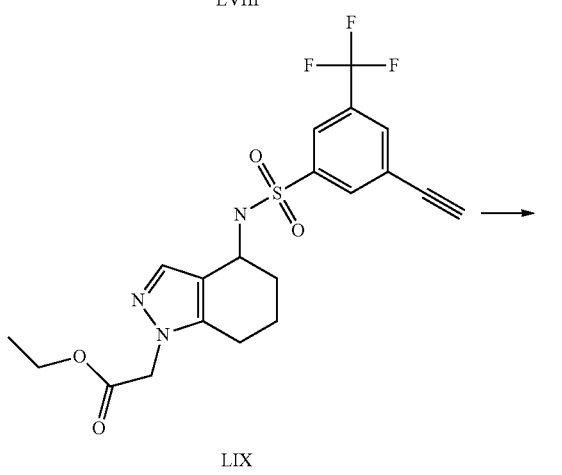

LIX

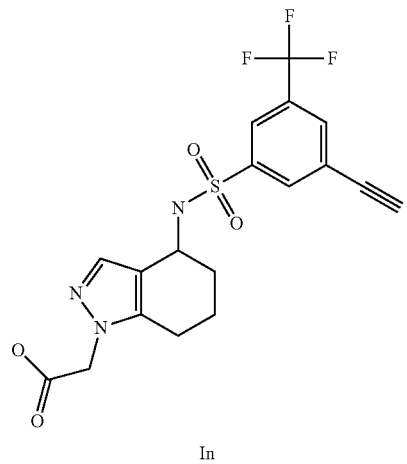

In

Synthesis of the acetylene derivative of structure In is illustrated in Scheme 11. Formation of compound In can be achieved by a Sonogashira coupling reaction between the bromo derivative LVI and trimethylsilylacetylene (LVII), followed by a potassium fluoride mediated trimethylsilanyl removal, and subsequent ester hydrolysis.

In the first step of this sequence, the intermediate LVIII can be generated by a coupling reaction between the aryl bromide compound LVI and trimethylsilanylacetylene (LVII) in the presence of a palladium catalyst such as tetrakis(triphenylphosphine)palladium(0), or bis(triphenylphosphine)palladium(II) chloride, and a copper(I) catalyst such as copper(I) iodide. The reaction can be carried out in the presence of a base such as triethylamine, or diisopropylethylamine in an inert solvent such as tetrahydrofuran, or toluene at 80° C. for about 20 minutes under microwave irradiation (Baldwin, K. P. et al., Synlett 11 (1993) 853).

Removal of trimethylsilanyl group of compound LVIII to give the terminal acetylene LIX can be conveniently achieved using potassium fluoride or tetrabutylammonium fluoride in a suitable solvent such as water, tetrahydrofuran, N,N-dimethylformamide, dimethyl sulfoxide, methanol, or mixtures thereof, at room temperature for several hours. Alternatively, a base such as potassium carbonate or potassium hydroxide can be used for the trimethylsilanyl group removal. The reaction can be carried out in a suitable solvent such as methanol, tetrahydrofuran, water or the mixtures thereof at room temperature for several hours.

Hydrolysis of compound LIX gives the compound of interest of formula In. The reaction can be carried out in the presence of an aqueous inorganic base such as sodium hydroxide or potassium hydroxide, in an inert solvent such as 1,4-dioxane or tetrahydrofuran, at room temperature for several hours.

Scheme 12

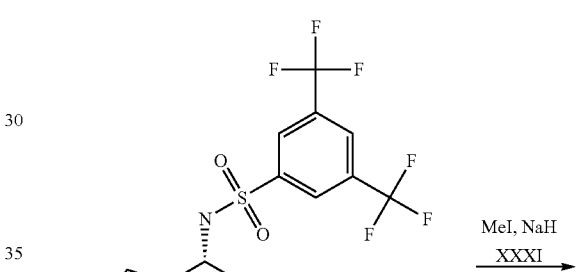

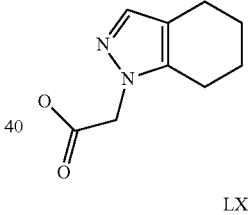

LX

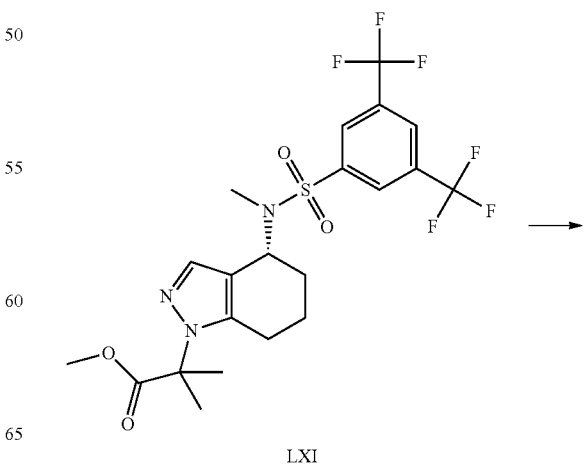

LXI

-continued

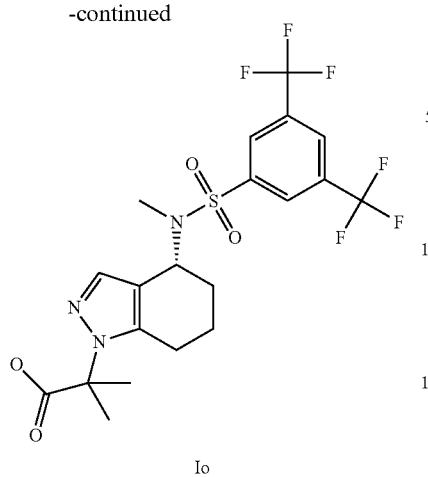

Io

Compound Io can be prepared according to Scheme 12. The intermediate LXI is formed by methylation of compound LX under strongly basic conditions. Further hydrolysis of the ester LXI gives compound Io.

Conversion of compound LX to its peralkylated derivative LXI can be achieved with methyl iodide (XXXI) in the presence of an excess amount of a strong base such as sodium hydride in an inert solvent such as N,N-dimethylformamide, tetrahydrofuran or dichloromethane for several hours.

Hydrolysis of compound LXI gives the compound of interest of formula Io. The reaction can be carried out in the presence of an aqueous inorganic base such as sodium hydroxide or potassium hydroxide, in an inert solvent such as 1,4-dioxane or tetrahydrofuran, at room temperature for several hours.

Scheme 13

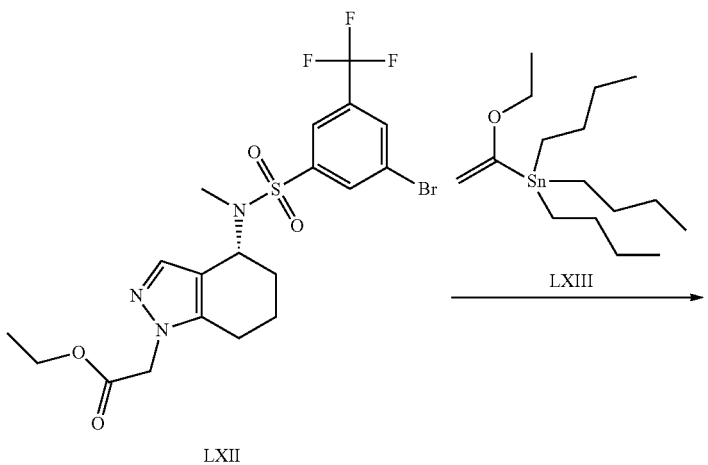

LXII

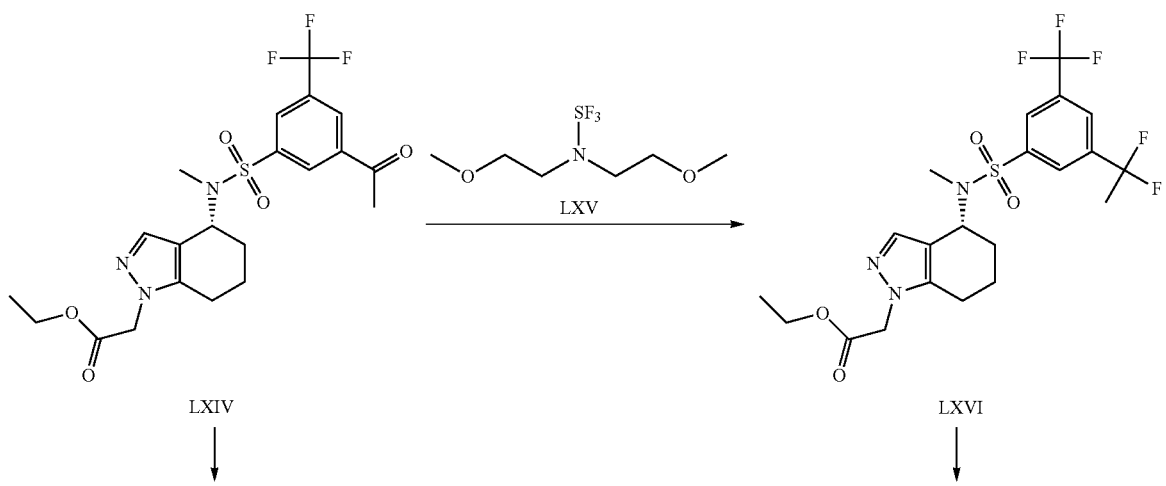

LXIV  LXVI

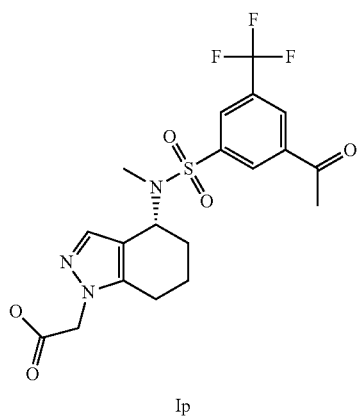

Ip

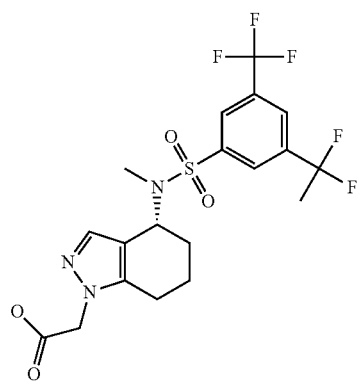

Iq

Compounds Ip and Iq can be achieved according to Scheme 13. The compound of interest Ip can be achieved via a Stille coupling between the bromo derivative LXII and the appropriate vinyl-stannane derivative, followed by an ester hydrolysis reaction. Conversion of the ketone LXIV to the corresponding gem-difluoride LXVI can be accomplished with nucleophilic fluorinating sources. Hydrolysis of the ethyl ester LXVI affords compound Iq.

The ketone LXIV can be achieved by a Stille coupling reaction of the corresponding bromo derivative LXII with the appropriate vinyl-stannane derivative such as tributyl(1-ethoxyalkenyl)tin, and then acidic hydrolysis with hydrochloric acid at room temperature to 70° C. for 30 minutes to 18 hours in water or a mixture of water and tetrahydrofuran. Stille coupling can be done in the presence of a palladium catalyst such as tetrakis(triphenylphosphine) palladium(0) (Pd(PPh$_3$)$_4$), or [1,1'-bis(diphenylphosphino)ferrocene]dichloropalladium(II) (PdCl$_2$(dppf)) in an inert solvent such as dimethylformamide, toluene, dioxane, acetonitrile or mixture of thereof at a temperature between 80 and 150° C. for 1 to 18 hours under an argon atmosphere. Alternatively, the reaction can be carried out in the presence of a palladium catalyst tris(dibenzylideneacetone)dipalladium(0) (Pd$_2$(dba)$_3$), and the ligand triphenylarsine (Ph$_3$As).

Hydrolysis of compound LXIV gives the compound of interest of formula Ip. The reaction can be carried out in the presence of an aqueous inorganic base such as sodium hydroxide, or potassium hydroxide in an inert solvent such as 1,4-dioxane or tetrahydrofuran at room temperature for several hours.

Transformation of the ketone LXIV to the gem-difluoride LXVI can be carried out by nucleophilic fluorinating sources such as diethylaminosulfur trifluoride (DAST), Bis(2-methoxyethyl)aminosulfur trifluoride, (CH$_3$OCH$_2$CH$_2$)$_2$NSF$_3$ (Deoxo-Fluor reagent), α,α-difluoroamines, or N,N-diethyl-α,α-difluoro-(m-methylbenzyl)amine (DFMBA) in a suitable solvent such as tetrahydrofuran, dichloromethane, or mixtures thereof, at a temperature between room temperature and 180° C. for several hours (reference: Lal, G. S. et al., J. Org. Chem. 64 (1999) 7048).

Hydrolysis of compound LXVI gives the compound of interest of formula Iq. The reaction can be carried out in the presence of an aqueous inorganic base such as sodium hydroxide or potassium hydroxide, in an inert solvent such as 1,4-dioxane or tetrahydrofuran, at room temperature for several hours.

Scheme 14

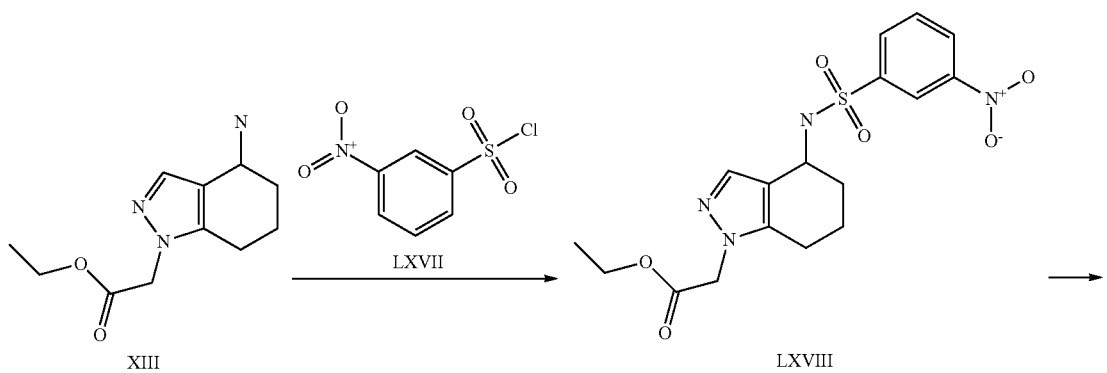

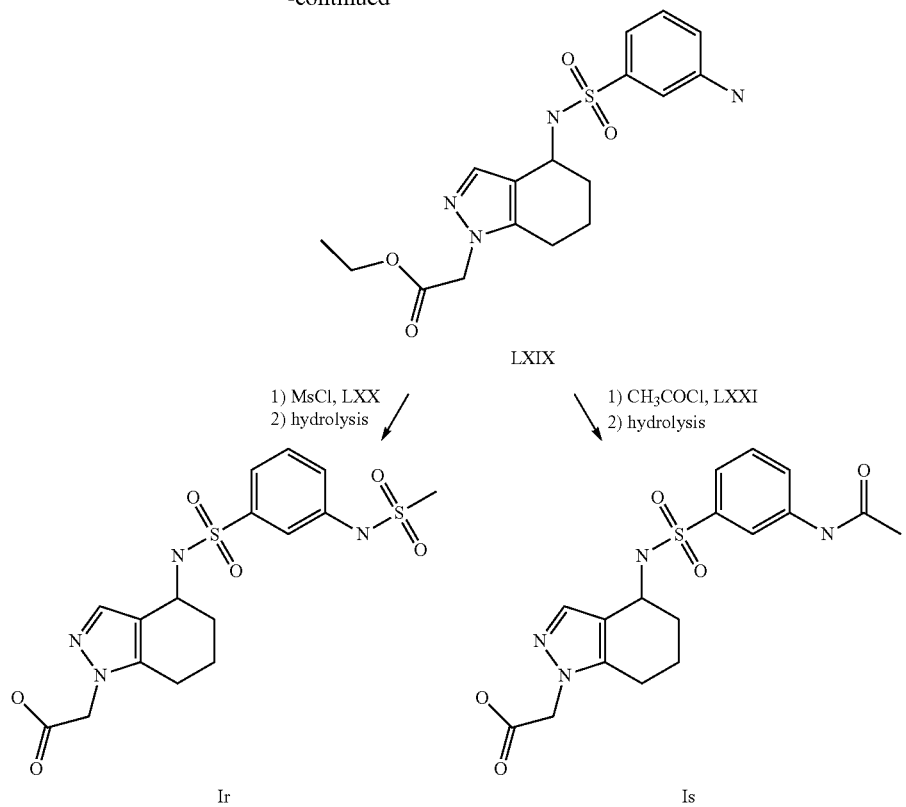

Compounds Ir and Is can be synthesized as illustrated in Scheme 14. The aniline intermediate LXIX can be generated by treating compound XIII with 3-nitrobenzensulfonyl chloride (LXVII), followed by reduction of the nitro group to the corresponding amine group. Sulfonylation of the aniline LXIX, followed by hydrolysis of the ester produces the compound of interest Ir. Alternatively, acetylation of compound LXIX, followed by hydrolysis affords the compound of interest Is.

Sulfonylation of the amine compound XIII with 3-nitrobenzensulfonyl chloride (LXVII) to give the sulfonamide LXVIII can be easily accomplished using methods well known to someone skilled in the art. For example, the reaction can be carried out in the presence of a base such as triethylamine, pyridine, or dimethyl-pyridin-4-yl-amine, in a suitable inert solvent such as dichloromethane, acetonitrile, 1,4-dioxane, or tetrahydrofuran and mixtures thereof, at room temperature for 16 hours.

Reduction of the nitro compound LXVIII to the corresponding amine derivative LXIX can be done using methods well known to someone skilled in the art. For example, zinc reduction can be employed. The reaction typically is carried out under acidic conditions by using acetic acid, hydrochloric acid, or ammonium chloride in a suitable solvent such as methanol, ethanol, tetrahydrofuran, water or mixtures thereof, at a temperature between room temperature and reflux temperature of the solvent used for several hours.

Following the same procedure as the step 1 of this sequence, sulfonylation of the amine compound LXIX with methanesulfonyl chloride (LXX) provides the corresponding methyl sulfonamide. Hydrolysis of this sulfonamide leads to the final compound of interest Ir. The reaction can be carried out in the presence of an aqueous inorganic base such as sodium hydroxide or potassium hydroxide, in an inert solvent such as 1,4-dioxane or tetrahydrofuran, at room temperature for several hours.

In the same fashion, acetylation of the amine compound LXIX with acetyl chloride (LXXI) can be carried out in the presence of a base such as triethylamine, pyridine, or dimethyl-pyridin-4-yl-amine in a suitable inert solvent such as dichloromethane, acetonitrile, 1,4-dioxane, or tetrahydrofuran and mixtures thereof, at room temperature for 16 hours. Further hydrolysis of the above acetylated compound produces the compound of interest Is. The reaction can be carried out in the presence of an aqueous inorganic base such as sodium hydroxide or potassium hydroxide, in an inert solvent such as 1,4-dioxane or tetrahydrofuran, at room temperature for several hours.

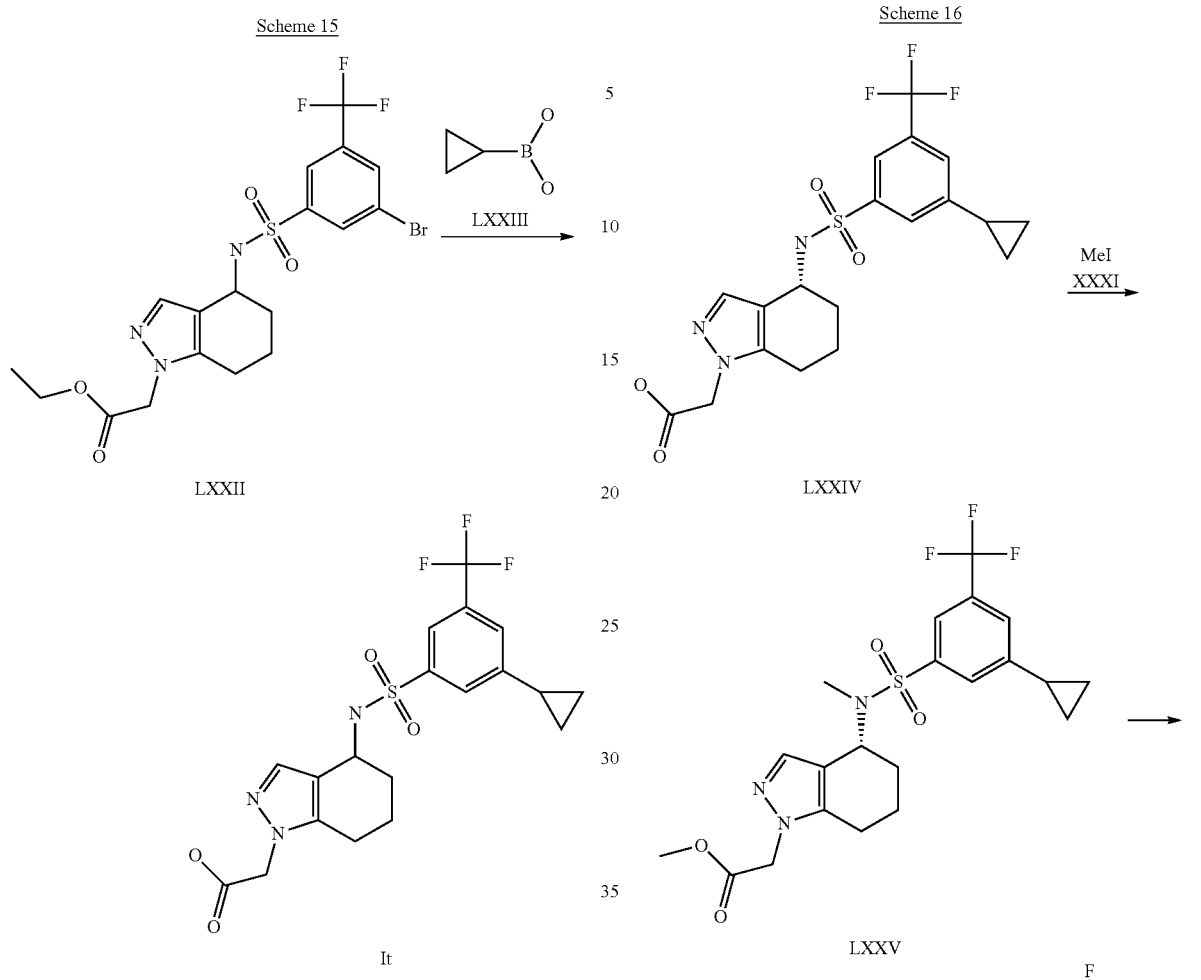

The compound of interest It can be generated directly from compound LXXII as shown in Scheme 15. This process is similar to that outlined in Scheme 6, except in this case the acid as product is directly generated from the Suzuki coupling reaction. The coupling reaction between the bromo compound LXXII and cyclopropylboronic acid (LXXIII) in the presence of water produces compound It.

The reaction of cyclopropylboronic acid (LXXIII) with compound LXXII (which can be prepared according to scheme 4) to give compound It can be easily carried out under Suzuki coupling conditions in the presence of a palladium catalyst such as palladium acetate, [1,1'-bis(diphenylphosphino)ferrocene]dichloropalladium(II) (PdCl$_2$(dppf)) or tetrakis(triphenylphosphine)palladium(0) (Pd(PPh$_3$)$_4$), with a phosphine ligand (such as triphenylphosphine, or tricyclohexylphosphine) and a base such as potassium tert-butoxide, potassium phosphate, sodium carbonate, or sodium hydroxide, in an inert solvent such as N,N-dimethylformamide, dimethyl sulfoxide, toluene, ethanol, tetrahydrofuran, water or mixtures thereof, at a temperature between 130 and 180° C. for 15 to 30 minutes under microwave irradiation. Alternatively, the reaction can be carried out without the use of a microwave at a decreased temperature such as 130° C. for a longer reaction time (reference: Wallace, D. J. et al., Tetrahedron Lett. 43 (2002) 6987).

Compound of interest Iu can be prepared according to Scheme 16. In this sequence, formation of the N-methylation derivative is different from that of Scheme 4 only in that the starting material is an acid instead of an ester. N-Methylation of LXXIV with methyl iodide (XXXI) gives the corresponding N-methylated methyl ester LXXV. Hydrolysis of LXXV produces compound Iu.

N-methylation of the acid compound LXXIV to produce the N-methylated methyl ester LXXV can be achieved by treating LXXIV with methyl iodide (XXXI) in the presence of a weak base such as potassium carbonate or sodium carbonate, in an inert solvent such as N,N-dimethylformamide, acetonitrile or tetrahydrofuran, at 65° C. for several hours.

Hydrolysis of the ester LXXV gives the compound of interest Iu. The reaction can be carried out in the presence of an aqueous inorganic base such as sodium hydroxide or potassium hydroxide, in an inert solvent such as 1,4-dioxane or tetrahydrofuran, at room temperature for several hours.

EXAMPLES

Although certain exemplary embodiments are depicted and described herein, the compounds of the present invention can be prepared using appropriate starting materials according to the methods described generally herein and/or by methods available to one of ordinary skill in the art.

Materials and Instrumentation in General

Intermediates and final compounds were purified by either flash chromatography and/or preparative HPLC (high performance liquid chromatography). Flash chromatography was performed using (1) the Biotage SP1™ system and the Quad 12/25 Cartridge module (from Biotage AB) or (2) the ISCO CombiFlash® chromatography instrument (from Teledyne Isco, Inc.); unless otherwise noted. The silica gel brand and pore size utilized were: (1) KP-SIL™ 60 Å, particle size: 40-60 micron (from Biotage AB); (2) Silica Gel CAS registry No: 63231-67-4, particle size: 47-60 micron; or (3) ZCX from Qingdao Haiyang Chemical Co., Ltd, pore size: 200-300 mesh or 300-400 mesh. Preparative HPLC was performed on a reversed phase column using an Xbridge™ Prep $C_{18}$ (5 m, OBD™ 30×100 mm) column (from Waters Corporation), or a SunFire™ Prep $C_{18}$ (5 m, OBD™ 30×100 mm) column (from Waters Corporation)

Mass spectrometry (MS) was performed using a Waters® Alliance® 2795-ZQ™2000 (from Waters Corporation). Mass spectra data generally only indicates the parent ions unless otherwise stated. MS data is provided for a particular intermediate or compound where indicated.

Nuclear magnetic resonance spectroscopy (NMR) was performed using a Bruker Avance™ 400 MHZ Digital NMR Spectrometer (for the $^1$H NMR spectrum acquired at 400 MHz) (from Bruker BioSpin AG Ltd.). NMR data is provided for a particular intermediate or compound where indicated.

The microwave assisted reactions were carried out in a Biotage Initiator™ Sixty (or its early models) (from Biotage AB).

Chiral separation was performed by Preparative HPLC. Preparative HPLC was performed using an Agilent 1200 HPLC with a Chiral Pak® IA (5 m, 20×250 mm) column and a Chiral Pak® AS-H (5 m, 20×250 mm) column both from Daicel Chiral Technologies (China) co., Ltd.

All reactions involving air-sensitive reagents were performed under an inert atmosphere. Reagents were used as received from commercial suppliers unless otherwise noted.

Part I

Preparation of Preferred Intermediates

Preparation of ((R)-4-amino-4,5,6,7-tetrahydro-indazol-1-yl)-acetic acid ethyl ester (IIa) and ((S)-4-amino-4,5,6,7-tetrahydro-indazol-1-yl)-acetic acid ethyl ester (IIb)

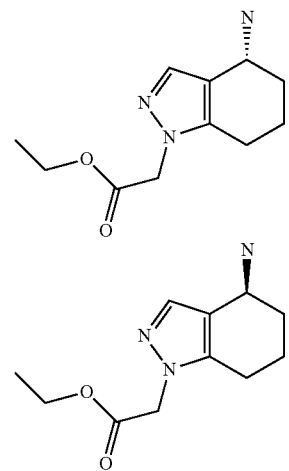

(4-Oxo-4,5,6,7-tetrahydro-indazol-1-yl)-acetic acid ethyl ester (VII)

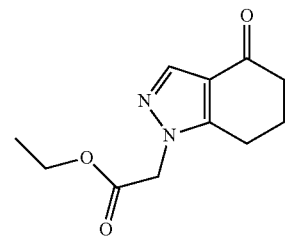

To a solution of cyclohexane-1,3-dione (50.7 g, 452 mmol) in N,N-dimethylformamide (700 mL) was added ethyl hydrazinoacetate hydrochloride (70 g, 452 mmol). The reaction mixture was stirred for 5 minutes before addition of dimethoxymethyl-dimethyl-amine (53.9 g, 452 mmol). The reaction mixture was divided into 50 vials, which were heated in a microwave at 190° C. for 2 minutes. After cooling to room temperature, the combined reaction mixture was concentrated in vacuo to remove most of the N,N-dimethylformamide. Water (200 mL) was added, and the resulting dark brown mixture was extracted with ethyl acetate (200 mL×3). The organic layers were combined, washed with brine (600 mL), dried over sodium sulfate and concentrated in vacuo to afford a brown oil, which was placed in a fridge overnight. The resulting yellow precipitate was filtered and washed with petroleum ether to give (4-oxo-4,5,6,7-tetrahydro-indazol-1-yl)-acetic acid ethyl ester (79 g, 79%) as yellow crystals. $^1$H NMR (400 MHz, CDCl$_3$) δ ppm 7.92 (s, 1H), 4.89 (s, 2H), 4.26 (m, 2H), 2.80 (t, J=6.4 Hz, 2H), 2.51 (t, J=6.4 Hz, 2H), 2.20 (t, J=6.4 Hz, 2H), 1.31 (t, J=7.2 Hz, 3H). MS calcd. for C$_{11}$H$_{14}$N$_2$O$_3$ 222, obsd. (ESI$^+$) (M+H)$^+$223.

(4-Hydroxyimino-4,5,6,7-tetrahydro-indazol-1-yl)-acetic acid ethyl ester (IX)

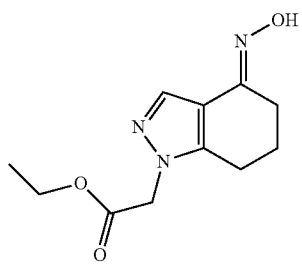

To a stirred solution of 4-oxo-4,5,6,7-tetrahydro-indazol-1-yl)-acetic acid ethyl ester (222 mg, 1.0 mmol) in ethanol (10 mL) was added hydroxylamine hydrochloride salt (74 mg, 1.05 mmol). The reaction mixture was heated at reflux for 1 hour. After cooling to room temperature, a solution of concentrated ammonia and saturated ammonium chloride (10 mL, 1:5, v/v) was added to the reaction mixture. The resulting solution was extracted with ethyl acetate (25 mL×3). The combined organic layers were washed with brine (30 mL), dried over sodium sulfate and concentrated in vacuo to give 4-hydroxyimino-4,5,6,7-tetrahydro-indazol-1-yl)-acetic acid ethyl ester (203 mg, 85%) as a white solid, which was used for the next step without further purification. The above white solid contained a pair of isomers in 10 to 1 ratio as determined by $^1$HNMR. For the major isomer, $^1$H NMR (400 MHz, CDCl$_3$) δ ppm 8.29 (s, 1H), 4.89 (s, 2H), 4.26 (m, 2H), 2.73 (t, J=6.4 Hz, 2H), 2.58 (t, J=6.4 Hz, 2H), 2.10 (t, J=6.4 Hz, 2H), 1.31 (t, J=7.2 Hz, 3H). MS calcd. for C$_{11}$H$_{15}$N$_3$O$_3$ 237, obsd. (ESI$^+$) [(M+H)$^+$]: 238.

(4-Amino-4,5,6,7-tetrahydro-indazol-1-yl)-acetic acid ethyl ester (XIII)

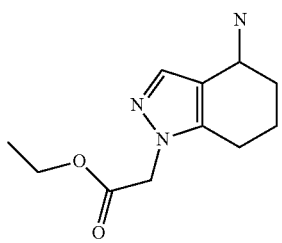

To a solution of (4-hydroxyimino-4,5,6,7-tetrahydro-indazol-1-yl)-acetic acid ethyl ester (132 mg, 0.59 mmol), sodium cyanoborohydride (110 mg, 1.76 mmol), and ammonium acetate (0.5 g, 7.2 mmol) in methanol (10 mL) was added titanium (III) chloride (0.99 mL, 20% wt in water, 1.68 mmol) dropwise. The reaction mixture was stirred at room temperature for 2 hours under an argon atmosphere. To the above mixture were added water (10 mL) and a solution of concentrated ammonia and saturated ammonium chloride (10 mL, 1:5, v/v). The resulting mixture was filtered through a pad of Celite® (a diatomite filter from World Minerals Inc.) and washed with dichloromethane (30 mL). The separated aqueous layer was extracted with dichloromethane (20 mL×3). The combined organic layers were washed with brine (30 mL), dried over sodium sulfate and concentrated in vacuo to afford 4-amino-4,5,6,7-tetrahydro-indazol-1-yl)-acetic acid ethyl ester (131 mg, 99%) as a viscous light brown oil. $^1$H NMR (400 MHz, CD$_3$OD) δ ppm 7.76 (s, 1H), 5.34 (s, 2H), 4.60 (m, 2H), 4.34 (m, 2H), 2.70 (m, 2H), 2.20 (m, 1H), 1.98 (m, 3H), 1.32 (t, J=7.2 Hz, 3H). MS calcd. for C$_{11}$H$_{17}$N$_3$O$_2$ 223, obsd. (ESI$^+$) [(M+H)$^+$] 224.

((R)-4-Benzyloxycarbonylamino-4,5,6,7-tetrahydro-indazol-1-yl)-acetic acid ethyl ester (XVa) and ((S)-4-Benzyloxycarbonylamino-4,5,6,7-tetrahydro-indazol-1-yl)-acetic acid ethyl ester (XVb)

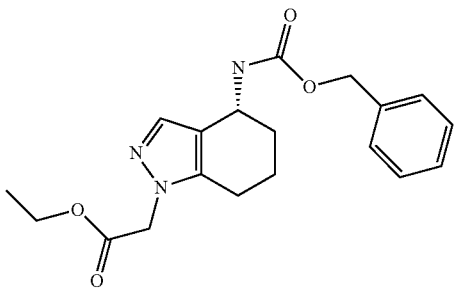

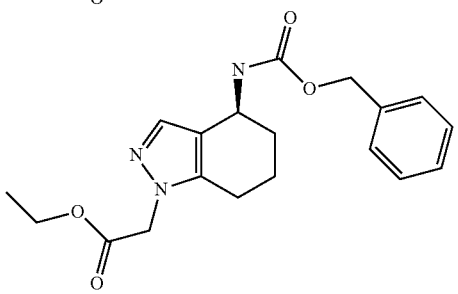

To a solution of (4-amino-4,5,6,7-tetrahydro-indazol-1-yl)-acetic acid ethyl ester (60 mg, 0.27 mmol) in 5% sodium carbonate (0.57 mL) and 1,4-dioxane (1 mL) was added benzyl chloroformate (58 μL, 0.40 mmol) at 0° C. The reaction was allowed to warm to room temperature slowly, and stirred overnight. The reaction mixture was partitioned between water (10 mL) and dichloromethane (20 mL×3). The combined organic layers were collected and dried over sodium sulfate, filtered and concentrated in vacuo. The residue was purified by column chromatography (50% ethyl acetate in hexanes) to afford racemic 4-benzyloxycarbonylamino-4,5,6,7-tetrahydro-indazol-1-yl)-acetic acid ethyl ester (94.2 mg, 98.2%) as a white solid. $^1$H NMR (400 MHz, CDCl$_3$) δ ppm 7.54 (s, 1H), 7.49-7.35 (m, 4H), 5.18 (s, 2H), 5.23 (s, 2H), 4.92-4.80 (m, 3H), 4.23 (dd, J=7.2 Hz, 2H), 2.52 (m, 2H), 2.05-1.88 (m, 4H), 1.30 (t, J=7.2 Hz, 3H). MS calcd. for C$_{19}$H$_{23}$N$_3$O$_4$ 357, obsd. (ESI$^+$) [(M+H)$^+$] 358. Chiral separation (Gilson instrument: column: Daicel CHIRALPAK® AS-H; flow rate: 15 mL/min; gradient: 55% hexane in propan-2-ol) gave ((R)-4-benzyloxycarbonyl-amino-4,5,6,7-tetrahydro-indazol-1-yl)-acetic acid ethyl ester (retention time 7.2 minutes) and ((S)-4-benzyloxycarbonylamino-4,5,6,7-tetrahydro-indazol-1-yl)-acetic acid ethyl ester (retention time 8.7 minutes). The recovery for both isomers together was 70%. It is noted that the absolute stereochemistry of the R-configuration of the intermediates and compounds of the present invention was further confirmed by X-ray crystallography of (R)-[4-(3-Bromo-5-tert-butyl-benzenesulfonylamino)-4,5,6,7-tetrahydro-indazol-1-yl]-acetic acid ethyl ester which was capable of being crystallized.

((R)-4-Amino-4,5,6,7-tetrahydro-indazol-1-yl)-acetic acid ethyl ester (IIa)

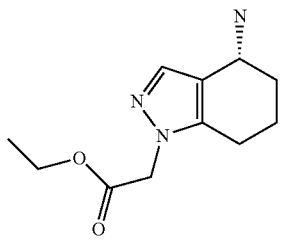

A solution of ((R)-4-benzyloxycarbonylamino-4,5,6,7-tetrahydro-indazol-1-yl)-acetic acid ethyl ester (357 mg, 1.0 mmol) in ethanol was hydrogenolyzed over 10% palladium on carbon (40 mg) under atmospheric pressure at room temperature for 3 hours. The reaction mixture was then filtered through a pad of Celite® (diatomite filter). The filtrate was collected, and concentrated in vacuo to afford ((R)-4-amino-4,5,6,7-tetrahydro-indazol-1-yl)-acetic acid ethyl ester (224 mg, 99%) as a light yellow oil. MS calcd. for $C_{11}H_{17}N_3O_2$ 223, obsd. (ESI$^+$) [(M+H)$^+$] 224.

((S)-4-Amino-4,5,6,7-tetrahydro-indazol-1-yl)-acetic acid ethyl ester (IIb)

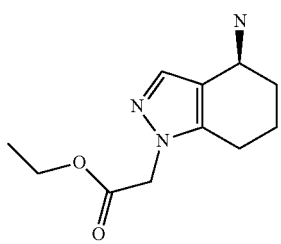

A solution of ((S)-4-amino-4,5,6,7-tetrahydro-indazol-1-yl)-acetic acid ethyl ester (357 mg, 1.0 mmol) in ethanol was hydrogenated over 10% Pd/C (40 mg) under atmospheric pressure at room temperature for 3 hours. The reaction mixture was then filtered through a pad of Celite® (diatomite filter). The filtrate was collected, and concentrated in vacuo to afford ((S)-4-amino-4,5,6,7-tetrahydro-indazol-1-yl)-acetic acid ethyl ester (224 mg, 99%). MS calcd. for $C_{11}H_{17}N_3O_2$ 223, obsd. (ESI$^+$) [(M+H)$^+$] 224.

Alternatively, ((R)-4-amino-4,5,6,7-tetrahydro-indazol-1-yl)-acetic acid ethyl ester (IIa) and ((S)-4-amino-4,5,6,7-tetrahydro-indazol-1-yl)-acetic acid ethyl ester (IIb) can be synthesized according to Scheme 2. The detailed experimental procedures are described below.

((S)-4-Hydroxy-4,5,6,7-tetrahydro-indazol-1-yl)-acetic acid ethyl ester (XVIII)

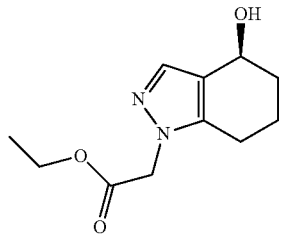

To a stirred solution of (4-oxo-4,5,6,7-tetrahydro-indazol-1-yl)-acetic acid ethyl ester (16.7 g, 75.0 mmol) in formic acid-triethylamine azeotropes (molar fraction of triethylamine: 0.2857, 45 mL) was added chloro-[(1S,2S)—N-(p-toluenesulfonyl)-1,2-diphenylethanediamine] (mesitylene) ruthenium(II) (1.86 g, 3.0 mmol). The reaction mixture was stirred at room temperature for 3 hours and then at 45° C. for 2.5 hours with occasional venting. After cooling to room temperature, 1N hydrochloric acid (50 mL) was added, followed by extraction with ethyl acetate (200 mL×3). The separated organic layers were combined, washed with brine (300 mL), dried over sodium sulfate, filtered and concentrated in vacuo. The residue was purified by column chromatography (gradient elution, 0-4% methanol in dichloromethane) to afford ((S)-4-hydroxy-4,5,6,7-tetrahydro-indazol-1-yl)-acetic acid ethyl ester (14.3 g, 85%) as a white solid with enantiomeric purity 99% as determined by Chiralpak™ IA column (condition: gradient: 50% hexane in ethanol, flow rate: 15 mL/min and retention time: 5.8 min for enantiomer A and 8.1 min for enantiomer B). $^1$H NMR (400 MHz, CD$_3$OD) δ ppm 7.47 (s, 1H), 4.89 (d, 4H), 4.76 (d, 1H), 4.20 (q, J=7.2 Hz, 2H), 2.52 (m, 2H), 2.06-1.84 (m, 4H), 1.29 (t, J=7.2 Hz, 3H). MS calcd. for $C_{11}H_{16}N_2O_3$ 224, obsd. (ESI$^+$) [(M+H)$^+$] 225.

((R)-4-Azido-4,5,6,7-tetrahydro-indazol-1-yl)-acetic acid ethyl ester (XXIa) and ((S)-4-Azido-4,5,6,7-tetrahydro-indazol-1-yl)-acetic acid ethyl ester (XXIb)

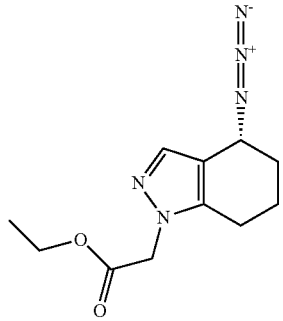

-continued

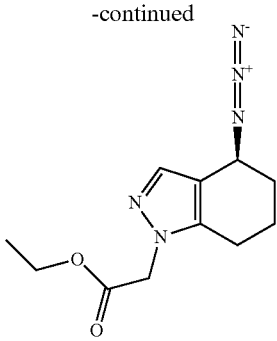

A oven dried flask was charged with ((S)-4-hydroxy-4,5,6,7-tetrahydro-indazol-1-yl)-acetic acid ethyl ester (14.3 g, 63.8 mmol), phosphorazidic acid diphenyl ester (DPPA) (15.1 mL, 70.1 mmol) and anhydrous toluene (100 mL). The mixture was cooled to −6° C. in an ice bath. 1,8-Diazabicyclo[5,4,0]-undec-7-ene (DBU) (9.53 mL, 63.8 mmol) was added dropwise, while maintaining the internal temperature of the reaction below 5° C. The reaction mixture was stirred below 10° C. for 16 hours. After the reaction was complete, a solution of saturated ammonium chloride (50 mL) was added, and the aqueous layer was extracted with dichloromethane (100 mL×3). The combined organic layers were dried over sodium sulfate, filtered and concentrated in vacuo. The residue was purified by column chromatography (gradient elution, 15-30% ethyl acetate in petroleum ether) to afford a mixture of two enantiomers (10.7 g, 67.4%, the ratio of (R)-enantiomer to (S)-enantiomer was 8:2 which was determined by HPLC with Chiralpak™ IA column).

The two enantiomers were further separated by HPLC using a Chiralpak™ IA column (separation condition: gradient: 70% hexane in ethanol; flow rate: 15 mL/min; retention time: 7.4 min for (R)-enantiomer and 8.9 min for (S)-enantiomer) to afford ((R)-4-azido-4,5,6,7-tetrahydro-indazol-1-yl)-acetic acid ethyl ester (7.1 g, e.e. %≧99%) as a viscous oil. $^1$H NMR (400 MHz, CD$_3$OD) δ ppm 7.51 (s, 1H), 4.91 (s, 4H), 4.63 (s, 1H), 4.20 (q, J=7.2 Hz, 2H), 2.52 (m, 2H), 1.97-1.88 (m, 4H), 1.29 (t, J=7.2 Hz, 3H). MS calcd. for C$_{11}$H$_{15}$N$_5$O$_2$ 249, obsd. (ESI$^+$) [(M+H)$^+$] 250.

((R)-4-Amino-4,5,6,7-tetrahydro-indazol-1-yl)-acetic acid ethyl ester (IIa)

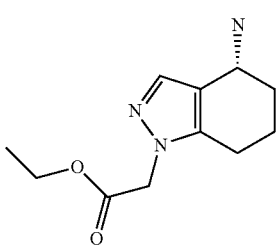

A solution of ((R)-4-azido-4,5,6,7-tetrahydro-indazol-1-yl)-acetic acid ethyl ester (1.25 g, 5.0 mmol) in ethanol (40 mL) was hydrogenated over 10% Pd/C (130 mg) under 30 psi in a 150 mL Parr bottle at room temperature for 1 hour. The reaction mixture was filtered through a pad of Celite® (diatomite filter). The filtrate was collected and concentrated in vacuo to afford ((R)-4-amino-4,5,6,7-tetrahydro-indazol-1-yl)-acetic acid ethyl ester as an oil (1.10 g, 98%), which was used in the next step without further purification. MS calcd. for C$_{11}$H$_{17}$N$_3$O$_2$ 223, obsd. (ESI$^+$) [(M+H)$^+$] 224.

Preparation of (R)-3-(4-amino-4,5,6,7-tetrahydro-indazol-1-yl)-propionic acid methyl ester (III)

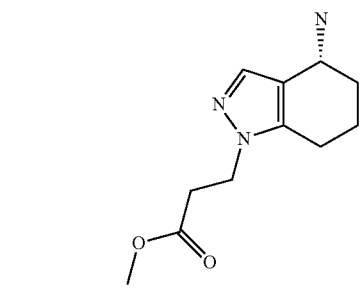

(R)-[1-(2-Hydroxy-ethyl)-4,5,6,7-tetrahydro-1H-indazol-4-yl]-carbamic acid benzyl ester (XXIII)

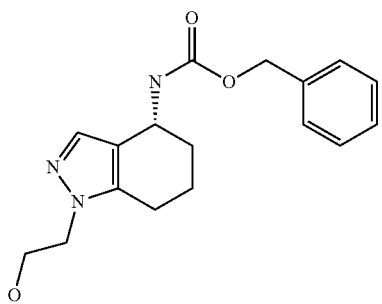

To a solution of ((R)-4-benzyloxycarbonylamino-4,5,6,7-tetrahydro-indazol-1-yl)-acetic acid ethyl ester (2.00 g, 5.60 mmol) in methanol (150 mL) was added sodium borohydride (1.61 g, 39.5 mmol). The mixture was stirred at 70° C. for 2 hours. After being cooled to room temperature, the reaction mixture was acidified to pH 7 with 5N hydrochloric acid, and then concentrated to remove methanol. The resulting mixture was extracted with dichloromethane (20 mL). After filtering out any insoluble materials from the organic layer, the filtrate was concentrated in vacuo to give (R)-[1-(2-hydroxy-ethyl)-4,5,6,7-tetrahydro-1H-indazol-4-yl]-carbamic acid benzyl ester (1.68 g, 95%) as a white solid. MS calcd. for $C_{17}H_{21}N_3O_3$ 315, obsd. (ESI$^+$) [(M+H)$^+$] 316.

Methanesulfonic acid 2((R)-4-benzyloxycarbonylamino-4,5,6,7-tetrahydroindazol-1-yl)-ethyl ester (XXV)

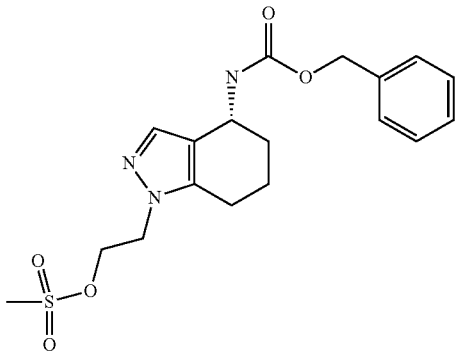

To a solution of (R)-[1-(2-hydroxy-ethyl)-4,5,6,7-tetrahydro-1H-indazol-4-yl]-carbamic acid benzyl ester (755 mg, 2.40 mmol) and pyridine (1.45 mL, 18.0 mmol) in dichloromethane was added methanesulfonyl chloride (1.40 mL, 18 mmol) dropwise at 0° C. The mixture was warmed to room temperature and stirred for 6 hours. The resulting mixture was poured into ice (10 g). The organic layer was then separated and washed with 0.1 N hydrochloric acid and saturated sodium bicarbonate, dried over sodium sulfate, filtered and concentrated in vacuo. The residue was purified by column chromatography (10% methanol in dichloromethane) to afford methanesulfonic acid 2-((R)-4-benzyloxycarbonylamino-4,5,6,7-tetrahydroindazol-1-yl)-ethyl ester (880 mg, 90%) as a white solid. MS calcd. for $C_{18}H_{23}N_3O_5S$ 393, obsd. (ESI$^+$) [(M+H)$^+$] 394.

(R)-[1-(2-Cyano-ethyl)-4,5,6,7-tetrahydro-1H-indazol-4-yl]-carbamic acid benzyl ester (XXVII)

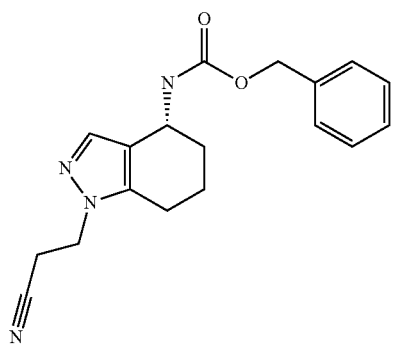

To a solution of methanesulfonic acid 2((R)-4-benzyloxycarbonylamino-4,5,6,7-tetrahydroindazol-1-yl)-ethyl ester (850 mg, 2.16 mmol) in dimethyl sulfoxide (20 mL) was added sodium cyanide (540 mg, 10.8 mmol). The mixture was stirred at 55° C. for 4 hours. After cooling, the mixture was added water, and the aqueous layer was extracted with ethyl acetate (20 mL×4). The combined organic layers were dried over sodium sulfate, filtered and then concentrated in vacuo. The residue was purified by flash column chromatography (10% methanol in dichloromethane) to afford (R)-[1-(2-cyano-ethyl)-4,5,6,7-tetrahydro-1H-indazol-4-yl]-carbamic acid benzyl ester (600 mg, 85%) as a white solid. MS calcd. for $C_{18}H_{20}N_4O_2$ 324, obsd. (ESI$^+$) [(M+H)$^+$] 325.

(R)-3-(4-Benzyloxycarbonylamino-4,5,6,7-tetrahydro-indazol-1-yl)-propionic acid methyl ester (XXVIII)

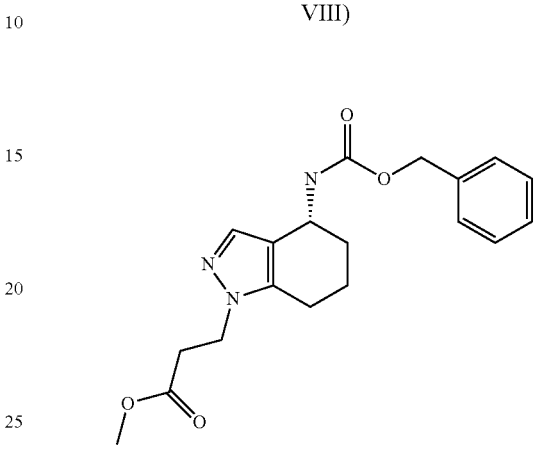

A solution of (R)-[1-(2-cyano-ethyl)-4,5,6,7-tetrahydro-1H-indazol-4-yl]-carbamic acid benzyl ester (700 mg, 1.96 mmol) in 2M solution of hydrogen chloride in methanol (60 mL) was stirred at room temperature for 32 hours. After the reaction was complete, the pH of the reaction mixture was adjusted to 7.5-8 with solid sodium bicarbonate, and then solvent was removed in vacuo. To the residue was added dichloromethane. Filtration and concentration gave (R)-3-(4-benzyloxycarbonyl-amino-4,5,6,7-tetrahydro-indazol-1-yl)-propionic acid methyl ester (770 mg, 99%) as a yellow solid. MS calcd. for $C_{19}H_{23}N_3O_4$ 357, obsd. (ESI$^+$) [(M+H)$^+$] 358.

(R)-3-(4-Amino-4,5,6,7-tetrahydro-indazol-1-yl)-propionic acid methyl ester (III)

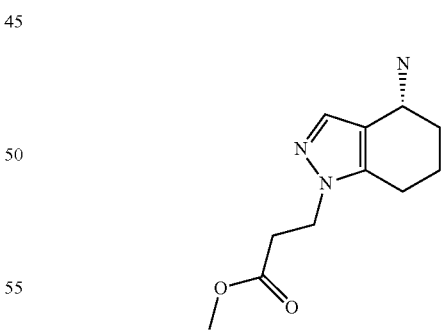

A solution of (R)-3-(4-benzyloxycarbonyl-amino-4,5,6,7-tetrahydro-indazol-1-yl)-propionic acid methyl ester (150 mg, 0.42 mmol) in methanol was hydrogenolyzed over 10% palladium on carbon (30 mg) under atmospheric pressure at room temperature for 3 hours. The reaction mixture was filtered and the filtrate was concentrated in vacuo to give (R)-3-(4-amino-4,5,6,7-tetrahydro-indazol-1-yl)-propionic acid methyl ester (93 mg, 99%) as a yellow oil, MS calcd. for $C_{11}H_{17}N_3O_2$ 223, obsd. (ESI$^+$) [(M+H)$^+$] 224.

Preparation of 3-methoxy-5-trifluoromethyl-benzenesulfonyl chloride

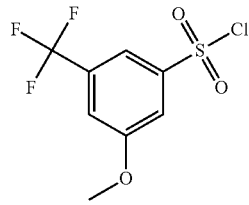

3-Methoxy-5-trifluoromethyl-phenylamine (10 g, 54 mmol) was mixed with trifluoroacetic acid (100 mL) in a 250 mL flask. After being cooled to 0° C., to the mixture was slowly added concentrated hydrochloric acid (10 mL), and then added a solution of sodium nitrite (4.7 g, 68 mmol) in water (5 mL) dropwise over 20 min at 0° C. The mixture was stirred for another 10 minutes after the addition and then poured into a stirred mixture of acetic acid (120 mL), sulfurous acid (0.94 N aqueous sulfur dioxide solution, 120 mL), copper(II) chloride (9.2 g) and copper(I) chloride (100 mg) at 0° C. The reaction mixture was allowed to warm to room temperature and stirred for 15 hours, and then water (200 mL) was added. The aqueous layer was extracted with ethyl acetate (100 mL×3). The combined organic layers were dried over sodium sulfate, filtered through a glass funnel and concentrated in vacuo. The residue was purified by column chromatography (20% ethyl acetate in petroleum ether) to afford 3-methoxy-5-trifluoromethyl-benzenesulfonyl chloride (3.9 g, 26.4%) as a white solid (reference: Cherney, R. J. et al., J. Med. Chem. 46 (2003) 1811). $^1$H NMR (400 MHz, CDCl$_3$) δ ppm 7.89 (s, 1H); 7.70 (s, 1H); 7.50 (s, 1H); 4.00 (s, 3H).

The following examples were prepared in an analogous manner as described for 3-methoxy-5-trifluoromethyl-benzenesulfonyl chloride starting from commercially available substituted phenyl amines.

| Starting amine | Sulfonyl chloride | $^1$H NMR (400 MHz, CDCl$_3$) δ ppm |
|---|---|---|
| 4-Fluoro-3-trifluoromethyl-Phenylamine | 4-Fluoro-3-trifluoromethyl-Benzenesulfonyl chloride | 8.35-8.37 (d, J = 6.0 Hz, 1 H); 8.29-8.33 (m, 1 H); 7.50-7.54 (t, J = 6.0 Hz, 1 H) |
| 3-Fluoro-5-trifluoromethyl-phenylamine | 3-Fluoro-5-trifluoromethyl-benzenesulfonyl chloride | 8.15 (s, 1 H); 7.97-7.99 (d, J = 4.0 Hz, 1 H); 7.74-7.76 (d, J = 4.0 Hz, 1 H) |
| 4-Methoxy-3-trifluoromethyl-phenylamine | 4-Methoxy-3-trifluoromethyl-benzenesulfonyl chloride | 8.26 (s, 1H); 8.22-8.24 (d, J = 8.8 Hz, 1 H); 7.21-7.23 (d, J = 8.8 Hz, 1 H); 4.00 (s, 3 H) |

Preparation of 3,5-di-tert-butyl-benzenesulfonyl chloride

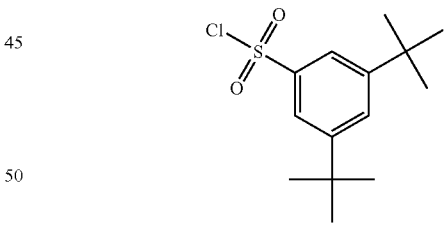

Chlorosulfonic acid (4 mL) was added to 1,3,5-tri-tert-butyl-benzene (1.5 g, 6.1 mmol) which had been cooled to 0° C. After being stirred at 0° C. for 30 minutes, the mixture was warmed to room temperature and stirred for 1 hour. Then the mixture was poured into ice water (50 mL) and extracted with dichloromethane (20 mL×3). The combined organic layers were dried over sodium sulfate and concentrated in vacuo. The residue was purified by column chromatography (gradient elution: 0-20% ethyl acetate in petroleum ether) to afford 3,5-di-tert-butyl-benzenesulfonyl chloride (880 mg, 50%) as a yellow solid (reference: Guthrie, R. D. et al. Aust. J. Chem. 40 (1987) 2133).

Part II

Preparation of Specific Compounds

Example 1-1

[(R)-4-(3-Bromo-5-trifluoromethyl-benzenesulfonylamino)-4,5,6,7-tetrahydro-indazol-1-yl]-acetic acid ethyl ester

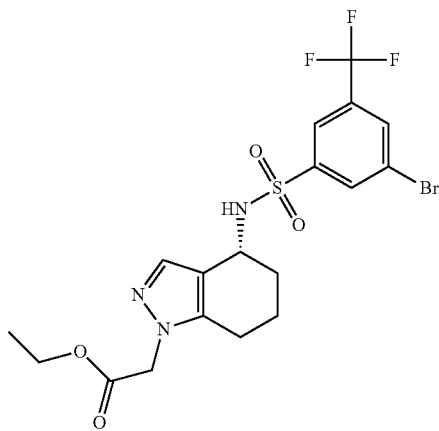

To a solution of ((R)-4-amino-4,5,6,7-tetrahydro-indazol-1-yl)-acetic acid ethyl ester (446 mg, 2.0 mmol) and 3-bromo-5-trifluoromethyl-benzenesulfonyl chloride (970 mg, 3.0 mmol) in tetrahydrofuran (5 mL) was added a solution of dimethyl-pyridin-4-yl-amine (489 mg, 4.0 mmol) in tetrahydrofuran (5 mL) dropwise. After being stirred at room temperature overnight, the mixture was concentrated. The residue was purified by column chromatography (gradient elution, 0-5% methanol in dichloromethane) to afford [(R)-4-(3-bromo-5-trifluoromethyl-benzenesulfonylamino)-4,5,6,7-tetrahydro-indazol-1-yl]-acetic acid ethyl ester (750 mg, 63.6%) as a white solid. MS calcd. for $C_{18}H_{19}BrF_3N_3O_4S$ 509, obsd. (ESI$^+$) [(M+H)$^+$] 510.

Examples 1-2 to 1-21

The following examples 1-2 to 1-18 were prepared in an analogous manner as described for example 1-1 using (4-amino-4,5,6,7-tetrahydro-indazol-1-yl)-acetic acid ethyl ester or its R form, 3-(4-benzyloxycarbonyl-amino-4,5,6,7-tetrahydro-indazol-1-yl)-propionic acid methyl ester or its R form, and the appropriate commercially available benzene sulfonyl chlorides.

| Example No. | Systematic Name | MS (ESI+, M + H) | Structure |
|---|---|---|---|
| 1-2 | [4-(3,5-Dichloro-benzenesulfonylamino)-4,5,6,7-tetrahydro-indazol-1-yl]-acetic acid ethyl ester | 432 | 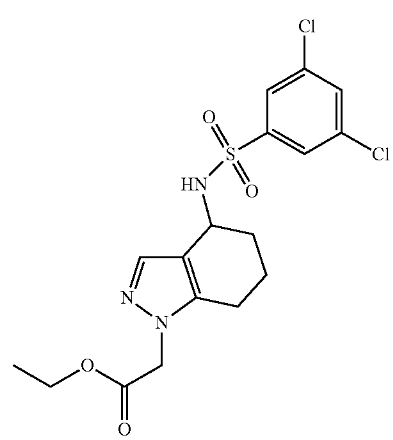 |

-continued
| Example No. | Systematic Name | MS (ESI+, M + H) | Structure |
|---|---|---|---|
| 1-3 | [4-(2,4-Dichloro-benzenesulfonylamino)-4,5,6,7-tetrahydro-indazol-1-yl]-acetic acid ethyl ester | 432 | 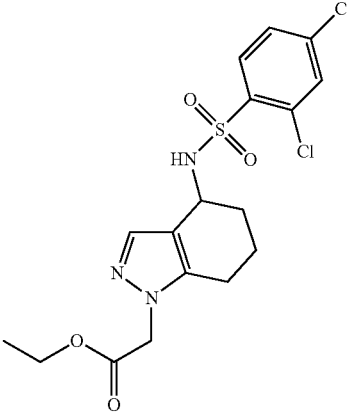 |
| 1-4 | [(R)-4-(3,5-Bis-trifluoromethyl-benzenesulfonylamino)-4,5,6,7-tetrahydro-indazol-1-yl]-acetic acid ethyl ester | 500 | 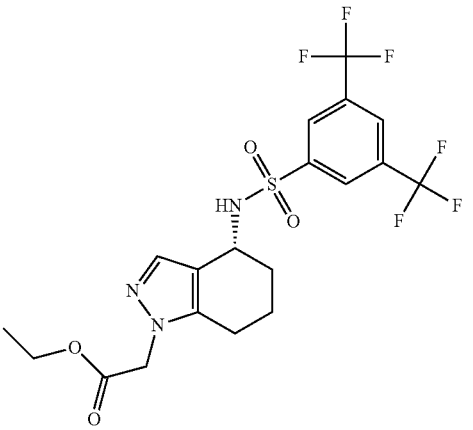 |
| 1-5 | [4-(4-Methyl-3-nitro-benzenesulfonylamino)-4,5,6,7-tetrahydro-indazol-1-yl]-acetic acid ethyl ester | 423 | 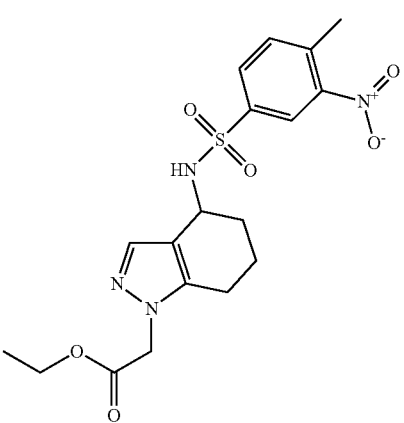 |

-continued
| Example No. | Systematic Name | MS (ESI+, M + H) | Structure |
|---|---|---|---|
| 1-6 | [4-(3,5-Dimethyl-benzenesulfonylamino)-4,5,6,7-tetrahydro-indazol-1-yl]-acetic acid ethyl ester | 392 | 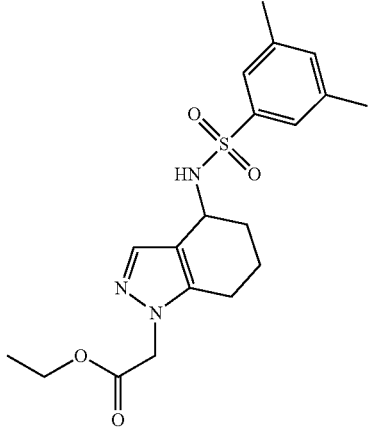 |
| 1-7 | [4-(3-Bromo-5-trifluoromethyl-benzenesulfonylamino)-4,5,6,7-tetrahydro-indazol-1-yl]-acetic acid ethyl ester | 510 | 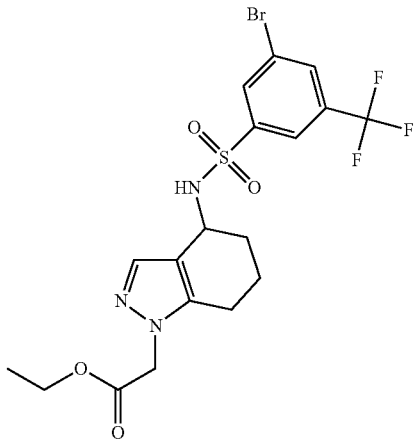 |
| 1-8 | [4-(4-Bromo-3-fluoro-benzenesulfonylamino)-4,5,6,7-tetrahydro-indazol-1-yl]-acetic acid ethyl ester | 432 | 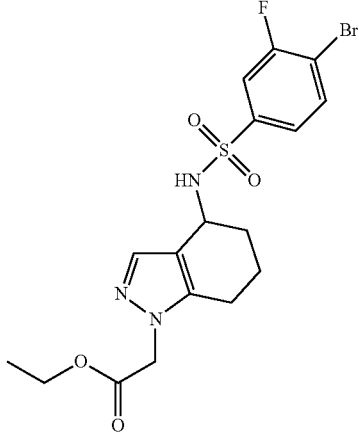 |

-continued
| Example No. | Systematic Name | MS (ESI+, M + H) | Structure |
|---|---|---|---|
| 1-9 | [4-(4-Bromo-3-methyl-benzenesulfonylamino)-4,5,6,7-tetrahydro-indazol-1-yl]-acetic acid ethyl ester | 456 | 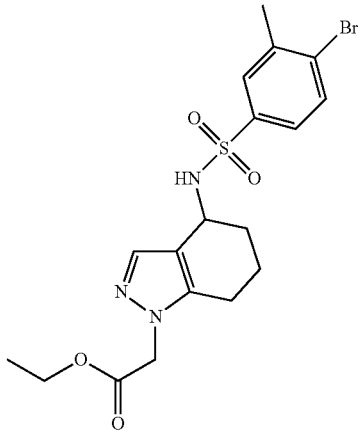 |
| 1-10 | [4-(4-Bromo-3-trifluoromethyl-benzenesulfonylamino)-4,5,6,7-tetrahydro-indazol-1-yl]-acetic acid ethyl ester | 510 | 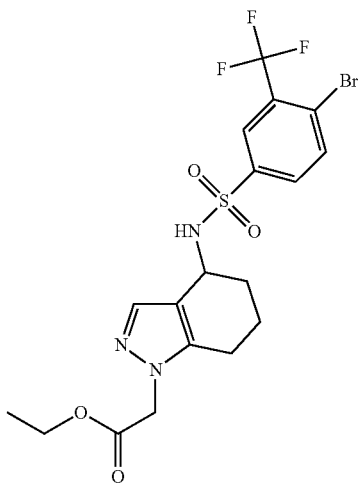 |
| 1-11 | [4-(5-Bromo-6-chloro-pyridine-3-sulfonylamino)-4,5,6,7-tetrahydro-indazol-1-yl]-acetic acid ethyl ester | 477 | 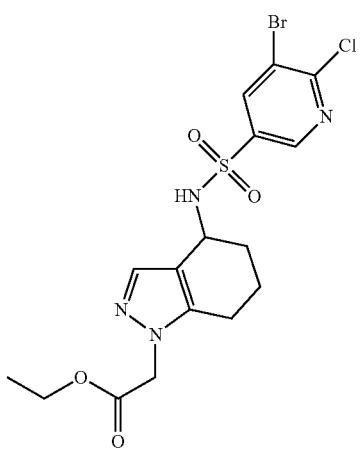 |

| Example No. | Systematic Name | MS (ESI+, M + H) | Structure |
|---|---|---|---|
| 1-12 | [(R)-4-(3-Methoxy-5-trifluoromethyl-benzenesulfonylamino)-4,5,6,7-tetrahydro-indazol-1-yl]-acetic acid ethyl ester | 462 | 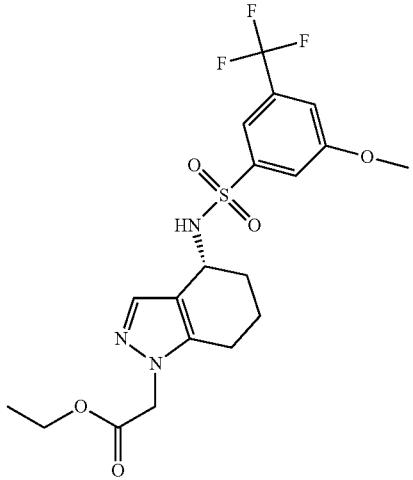 |
| 1-13 | [4-(2,5-Bis-trifluoromethyl-benzenesulfonylamino)-4,5,6,7-tetrahydro-indazol-1-yl]-acetic acid ethyl ester | 500 | 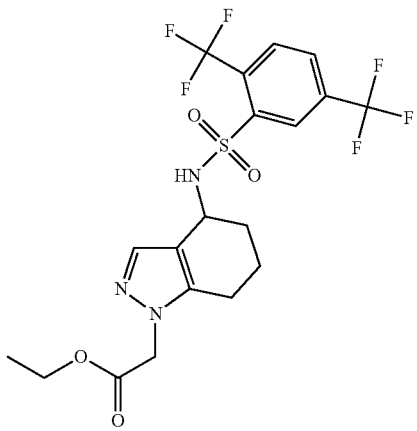 |
| 1-14 | [4-(3-Methanesulfonyl-benzenesulfonylamino)-4,5,6,7-tetrahydro-indazol-1-yl]-acetic acid ethyl ester | 442 | 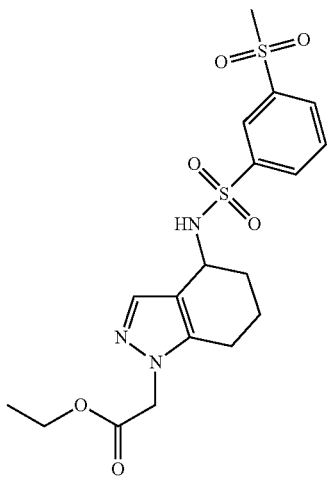 |

-continued
| Example No. | Systematic Name | MS (ESI+, M + H) | Structure |
|---|---|---|---|
| 1-15 | [4-(4-Methoxy-3-trifluoromethyl-benzenesulfonylamino)-4,5,6,7-tetrahydro-indazol-1-yl]-acetic acid ethyl ester | 462 | 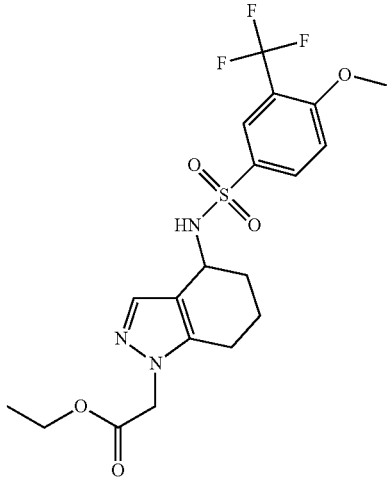 |
| 1-16 | [(R)-4-(3,5-Bis-methanesulfonyl-benzenesulfonylamino)-4,5,6,7-tetrahydro-indazol-1-yl]-acetic acid ethyl ester | 520 | 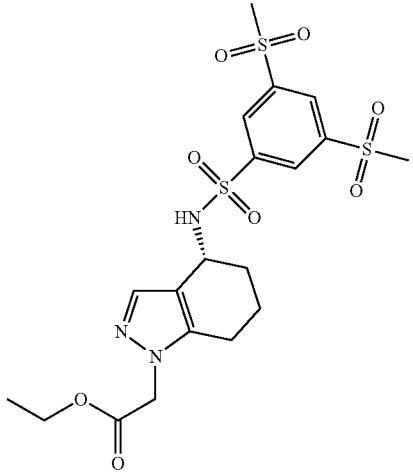 |

-continued

| Example No. | Systematic Name | MS (ESI+, M + H) | Structure |
|---|---|---|---|
| 1-17 | [4-(3-Chloro-4-methyl-benzenesulfonylamino)-4,5,6,7-tetrahydro-indazol-1-yl]-acetic acid ethyl ester | 412 | 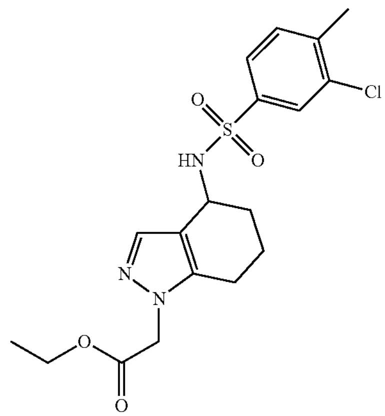 |
| 1-18 | 3-[(R)-4-(3,5-Bis-trifluoromethyl-benzenesulfonylamino)-4,5,6,7-tetrahydro-indazol-1-yl]-propionic acid methyl ester | 500 | 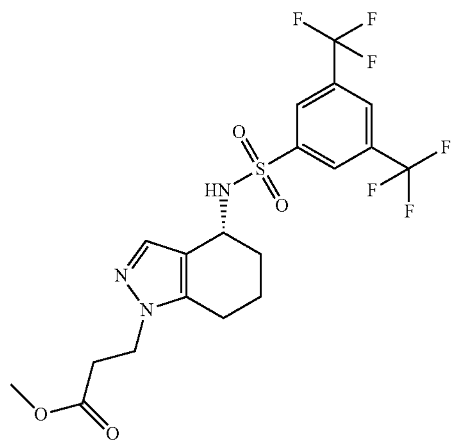 |

Example 1-1a

[(R)-4-(3-Bromo-5-trifluoromethyl-benzenesulfonylamino)-4,5,6,7-tetrahydro-indazol-1-yl]-acetic acid

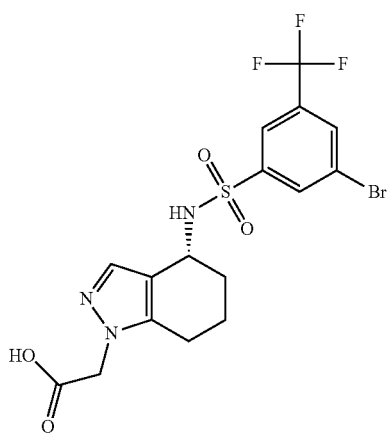

To a solution of [(R)-4-(3-bromo-5-trifluoromethyl-benzenesulfonylamino)-4,5,6,7-tetrahydro-indazol-1-yl]-acetic acid ethyl ester (18.0 mg, 0.035 mmol) in tetrahydrofuran (2 mL) was added an aqueous solution of sodium hydroxide (1 N, 2 mL). The resulting mixture was stirred at room temperature for 2 hours, then extracted with diethyl ether (6 mL). The organic layer was discarded. The aqueous layer was acidified with concentrated hydrochloric acid to pH 4 and then stirred with diethyl ether (2 mL) and petroleum ether (6 mL) at room temperature for 2 hours. The resulting mixture was filtered to afford [(R)-4-(3-bromo-5-trifluoromethyl-benzenesulfonylamino)-4,5,6,7-tetrahydro-indazol-1-yl]-acetic acid (13.3 mg, 78.8%) as a white powder. $^1$H NMR (400 MHz, CD$_3$OD) δ ppm 8.34 (s, 1H), 8.20 (s, 2H), 6.81 (s, 1H), 4.80 (s, 2 H), 4.48 (t, 1H), 2.50 (m, 2H), 2.00-1.72 (m, 4H). MS calcd. for C$_{16}$H$_{15}$BrF$_3$N$_3$O$_4$S 481, obsd. (ESI$^+$) [(M+H)$^+$] 482.

Examples 1-2a to 1-18a

The following examples 1-2a to 1-18a were prepared in an analogous manner as described for example 1-1a using the corresponding esters.

| Example No. | Systematic Name | ¹H NMR (400 MHz, CD₃OD) δ ppm | MS (ESI+, M + H) | Structure |
| --- | --- | --- | --- | --- |
| 1-2a | [4-(3,5-Dichloro-benzenesulfonylamino)-4,5,6,7-tetrahydro-indazol-1-yl]acetic acid | 7.90 (d, 2 H), 7.81 (t, 1 H), 6.81 (s, 1 H), 4.77 (s, 2 H), 4.45 (t, 1 H), 2.50 (m, 2 H), 1.99-1.77 (m, 4 H) | 404 | 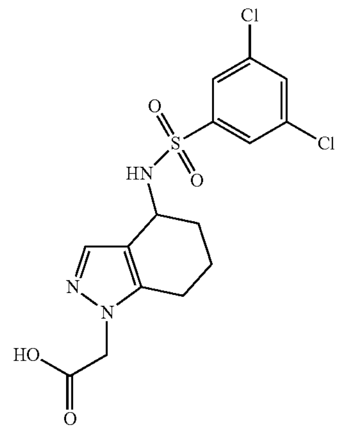 |
| 1-3a* | [4-(2,4-Dichloro-benzenesulfonylamino)-4,5,6,7-tetrahydro-indazol-1-yl]-acetic acid | 8.39 (d, J = 8.59 Hz, 1 H), 8.04 (d, J = 8.59 Hz, 1 H), 7.92 (d, J = 2.02 Hz, 1 H), 7.65 (dd, J = 8.46, 2.15 Hz, 1 H), 6.89 (s, 1 H), 4.77 (s, 1 H), 4.27 (d, J = 1.52 Hz, 1 H), 4.08 (s, 1 H), 2.39 (s., 2 H), 1.90 (s, 1 H), 1.70 (s., 1 H), 1.58 (d, J = 7.33 Hz, 2 H) | 404 | 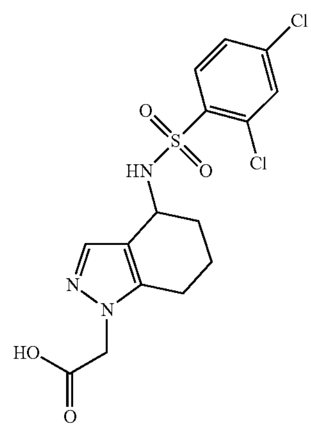 |
| 1-4a | [(R)-4-(3,5-Bis-trifluoromethyl-benzenesulfonylamino)-4,5,6,7-tetrahydro-indazol-1-yl]-acetic acid | 8.49 (s, 2 H), 8.34 (s, 1 H), 6.82 (s, 1 H), 4.81 (s, 2 H), 4.50 (t, 1 H), 2.50 (m, 2 H), 1.95-1.74 (m, 4 H) | 472 | 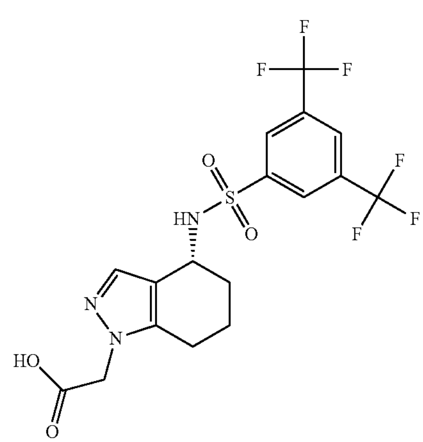 |

-continued

| Example No. | Systematic Name | $^1$H NMR (400 MHz, CD$_3$OD) δ ppm | MS (ESI+, M + H) | Structure |
|---|---|---|---|---|
| 1-5a | [4-(4-Methyl-3-nitro-benzenesulfonylamino)-4,5,6,7-tetrahydro-indazol-1-yl]-acetic acid | 8.47 (s, 1 H), 8.10 (d, 1 H), 7.72 (d, 1 H), 6.86 (s, 1 H), 4.80 (s, 2 H), 4.43 (t, 1 H), 2.69 (s, 3 H), 2.55 (m, 2 H) | 395 | 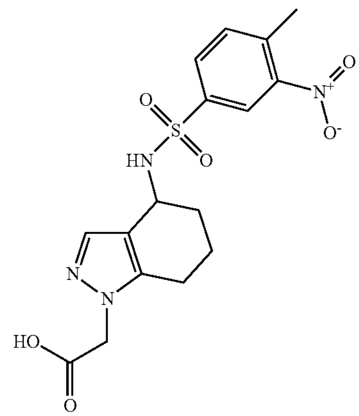 |
| 1-6a | [4-(3,5-Dimethyl-benzenesulfonylamino)-4,5,6,7-tetrahydro-indazol-1-yl]-acetic acid | 7.56 (s, 2 H), 7.34 (s, 1 H), 6.55 (s, 1 H), 4.80 (s, 2 H), 4.35 (t, 1 H), 2.54 (m, 2 H), 2.44 (s., 6 H), 1.95 (m, 1 H), 1.77 (m, 3 H) | 364 | 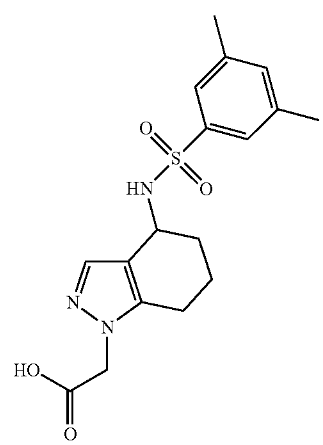 |
| 1-7a | [4-(3-Bromo-5-trifluoromethyl-benzenesulfonylamino)-4,5,6,7-tetrahydro-indazol-1-yl]-acetic acid | 8.37 (s, 1 H), 8.19 (s, 2 H), 6.80 (s, 1 H), 4.79 (s, 2 H), 4.45 (t, 1 H), 2.63-2.46 (m, 2 H), 2.00-1.89-2.00 (m, 1 H), 1.87-1.69 (m, 3 H) | 482 | 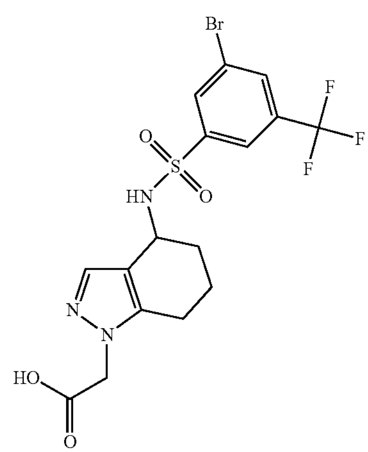 |

| Example No. | Systematic Name | $^1$H NMR (400 MHz, CD$_3$OD) δ ppm | MS (ESI+, M + H) | Structure |
|---|---|---|---|---|
| 1-8a | [4-(4-Bromo-3-fluoro-benzenesulfonylamino)-4,5,6,7-tetrahydro-indazol-1-yl]acetic acid | 7.94 (q, 1 H), 7.79 (q, 1 H), 7.70 (q, 1 H), 6.82 (s, 1 H), 4.78 (d, 2 H), 4.44 (t, H), 2.50 (m, 2 H), 2.01-1.74 (m, 4 H). | 432 | 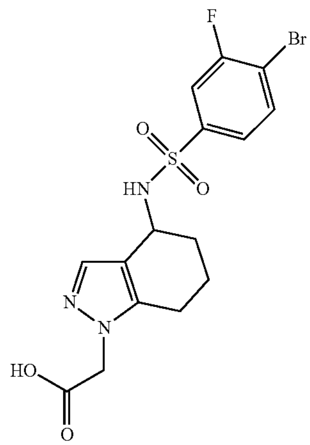 |
| 1-9a | [4-(4-Bromo-3-methyl-benzenesulfonylamino)-4,5,6,7-tetrahydro-indazol-1-yl]-acetic acid | 7.87 (s, 1 H), 7.81 (d, 1 H), 7.66 (d, 1 H), 6.65 (s, 1 H), 4.69 (s, 2 H), 4.38 (t, 1 H), 2.61-2.44 (m, 5 H), 1.99-1.89 (m, 1 H), 1.84-1.69 (m, 3 H) | 428 | 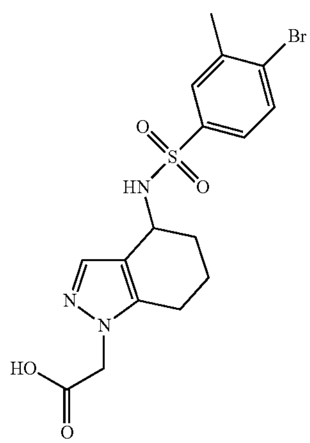 |
| 1-10a | [4-(4-Bromo-3-trifluoromethyl-benzenesulfonylamino)-4,5,6,7-tetrahydro-indazol-1-yl]-acetic acid | 8.27 (s, 1 H), 8.14-8.02 (m, 2 H), 6.88-6.78 (m, 1 H), 4.84-4.75 (m, 2 H), 4.44 (t, 1 H) 2.63-2.45 (m, 2 H), 1.99-1.90 (m, 1 H), 1.87-1.65 (m, 3 H) | 482 | 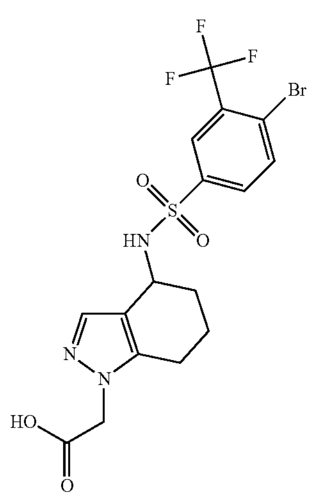 |

| Example No. | Systematic Name | ¹H NMR (400 MHz, CD₃OD) δ ppm | MS (ESI+, M + H) | Structure |
|---|---|---|---|---|
| 1-11a | [4-(5-Bromo-6-chloro-pyridine-3-sulfonylamino)-4,5,6,7-tetrahydro-indazol-1-yl]-acetic acid | 8.86 (d, 1 H), 8.59 (d, 1 H), 6.96 (s, 1 H), 4.82 (s, 2 H), 4.52 (t, 1 H), 2.64-2.47 (m, 2 H), 2.00-1.91 (m, 1 H), 1.89-1.78 (m, 2 H), 1.78-1.69 (m, 1 H) | 449 | 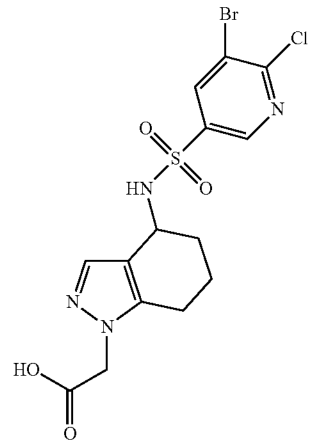 |
| 1-12a | [(R)-4-(3-Methoxy-5-trifluoromethyl-benzenesulfonylamino)-4,5,6,7-tetrahydro-indazol-1-yl]acetic acid | 7.78 (s, 1 H), 7.71 (s, 1 H), 7.49 (s, 1 H), 6.72-6.66 (m, 1 H), 5.52 (s, 1 H), 4.76-4.67 (m, 2 H), 4.42 (t, 1 H), 3.98 (s, 3 H), 2.62-2.44 (m, 2 H), 1.99-1.89 (m, 1 H), 1.79 (m, 3 H) | 434 | 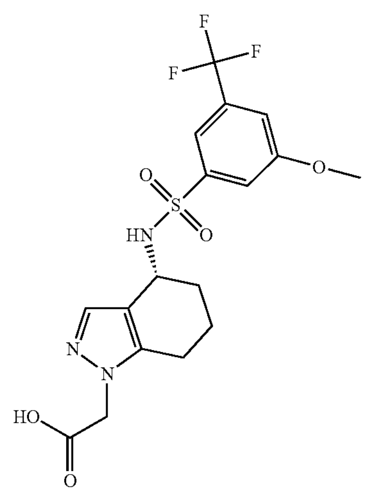 |
| 1-13a | [4-(2,5-Bis-trifluoromethyl-benzenesulfonylamino)-4,5,6,7-tetrahydro-indazol-1-yl]-acetic acid | 8.54 (s, 1 H), 8.21 (q, 2 H), 7.64 (s, 1 H), 5.03 (s, 2 H), 4.59 (t, 1 H), 2.71-2.61 (m, 2 H), 2.10-2.00 (m, 1 H), 1.93-1.71 (m, 3 H) | 472 | 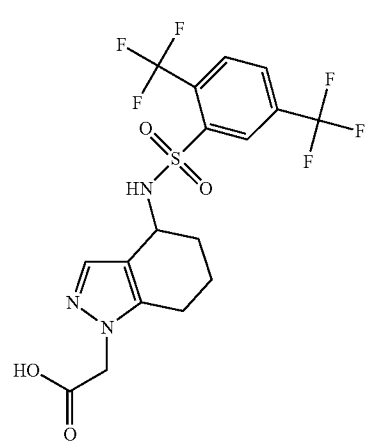 |

-continued

| Example No. | Systematic Name | ¹H NMR (400 MHz, CD₃OD) δ ppm | MS (ESI+, M + H) | Structure |
|---|---|---|---|---|
| 1-14a | [4-(3-Methanesulfonyl-benzenesulfonylamino)-4,5,6,7-tetrahydro-indazol-1-yl]acetic acid | 8.47 (s, 1 H), 8.30 (t, 2 H), 7.93 (t, 1 H), 7.57 (s 1 H), 5.06 (s, 2 H), 4.52 (t, 1 H), 3.23 (s, 3 H), 2.67 (d, 2 H), 2.01-1.70 (m, 4 H) | 414 | 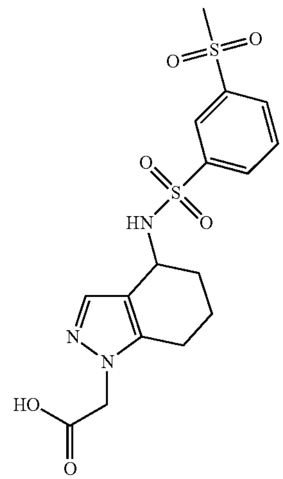 |
| 1-15a | [4-(4-Methoxy-3-trifluoromethyl-benzenesulfonylamino)-4,5,6,7-tetrahydro-indazol-1-yl]-acetic acid | 8.17 (d, 1 H), 8.11 (s, 1 H), 7.74 (d, 1 H), 6.78 (s, 1 H), 4.75 (s, 2 H), 4.36 (t, 1 H), 4.04 (s, 3 H), 2.50 (m, 2 H), 2.00-1.75 (m, 4 H). | 434 | 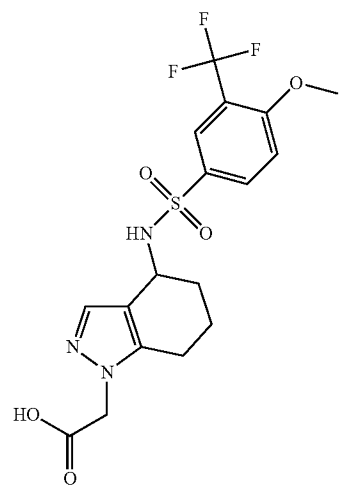 |
| 1-16a | [(R)-4-(3,5-Bis-methanesulfonyl-benzenesulfonylamino)-4,5,6,7-tetrahydro-indazol-1-yl]-acetic acid | 8.71 (s, 3 H), 6.81 (s, 1 H), 4.77 (s, 2 H), 4.51 (t, 1 H), 3.27 (s, 6 H), 2.61-2.42 (m, 2 H), 1.98-1.76 (m, 4 H) | 492 | 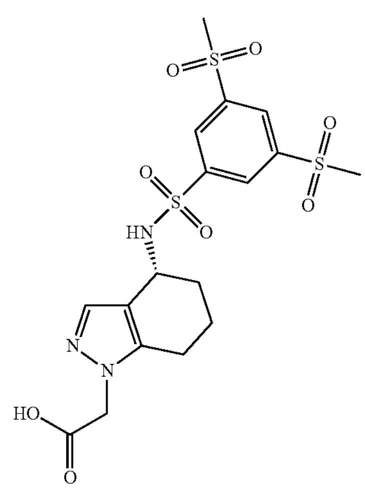 |

| Example No. | Systematic Name | ¹H NMR (400 MHz, CD₃OD) δ ppm | MS (ESI+, M + H) | Structure |
|---|---|---|---|---|
| 1-17a | [4-(3-Chloro-4-methyl-benzenesulfonylamino)-4,5,6,7-tetrahydro-indazol-1-yl]acetic acid | 7.89 (s, 1 H), 7.73 (d, 1 H), 7.51 (d, 1 H), 6.66 (s, 1 H), 4.69 (s, 2 H), 4.34 (s, 1 H), 2.61-2.40 (m, 5 H), 1.96-1.84 (m, 1 H), 1.82-1.65 (m, 3 H) | 384 | 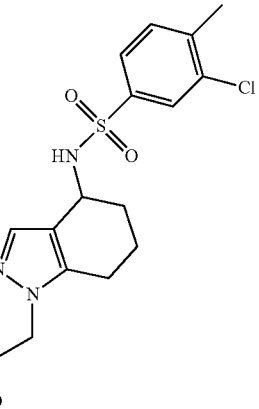 |
| 1-18a | 3-[(R)-4-(3,5-Bis-trifluoromethyl-benzenesulfonylamino)-4,5,6,7-tetrahydro-indazol-1-yl]-propionic acid | 8.43 (s, 2 H), 8.29 (s, 1 H), 6.73 (s, 1 H), 4.20 (t, 1 H), 4.15 (t, 2 H), 2.75 (m, 2 H), 2.71-2.53 (m, 2 H), 1.87-1.67 (m, 4 H) | 486 | 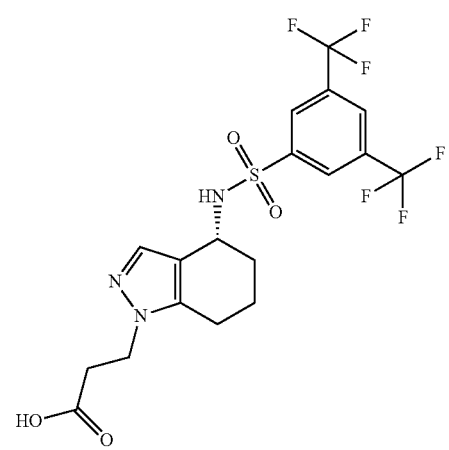 |

*The solvent used for ¹H NMR was DMSO-d6.

{(R)-4-[(3,5-Bis-trifluoromethyl-benzenesulfonyl)-methyl-amino]-4,5,6,7-tetrahydro-indazol-1-yl}-acetic acid ethyl ester

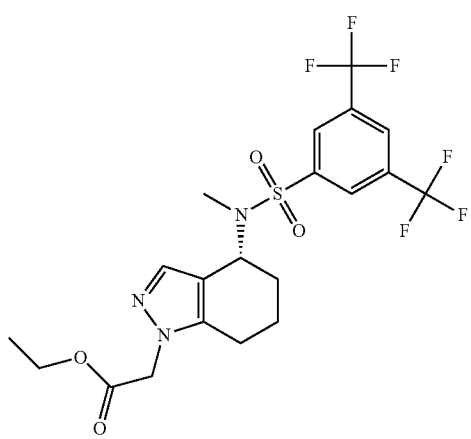

To a solution of (R)-{[4-(3,5-bis-trifluoromethyl-benzenesulfonylamino)-4,5,6,7-tetrahydro-indazol-1-yl]-acetic acid ethyl ester (example 1-5, prepared by the method analogous to the one described for example 1-1, 48.6 mg, 0.100 mmol) in acetonitrile (3 mL) was added potassium carbonate (27.6 mg, 0.200 mmol) and methyl iodide (9.5 μL, 0.150 mmol). After being heated at 70° C. under an argon atmosphere for 6 hours, the reaction mixture was cooled to room temperature, filtered through a glass funnel and concentrated in vacuo. The residue was purified by column chromatography (gradient elution, 0-5% methanol in dichloro-methane) to afford {(R)-4-[(3,5-bis-trifluoromethyl-benzenesulfonyl)-methyl-amino]-4,5,6,7-tetrahydro-indazol-1-yl}-acetic acid ethyl ester (42.6 mg, 83%) as a white solid. MS calcd. (calculated) for $C_{20}H_{21}F_6N_3O_4S$ 513, obsd. (observed) (ESI⁺) [(M+H)⁺] 514.

Examples 2-2 to 2-8

The following examples 2-2 to 2-8 were prepared in an analogous manner as described for example 2-1 using the appropriate ester intermediates.

| Example No. | Systematic Name | MS (ESI+, M + H) | Structure |
|---|---|---|---|
| 2-2 | {(R)-4-[(4-Bromo-2-chloro-benzenesulfonyl)-methyl-amino]-4,5,6,7-tetrahydro-indazol-1-yl}-acetic acid ethyl ester | 490 | 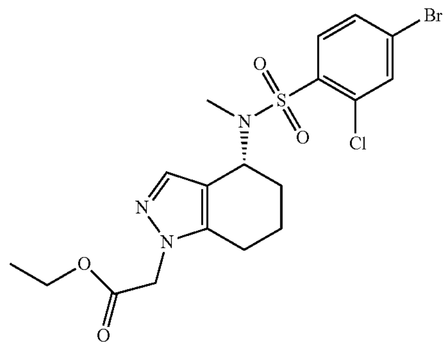 |
| 2-3 | {(R)-4-[(2-Chloro-4-trifluoromethyl-benzenesulfonyl)-methyl-amino]-4,5,6,7-tetrahydro-indazol-1-yl}-acetic acid ethyl ester | 480 | 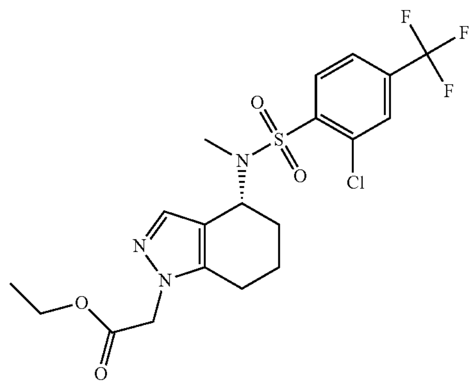 |
| 2-4 | {(R)-4-[(4-Bromo-2-fluoro-benzenesulfonyl)-methyl-amino]-4,5,6,7-tetrahydro-indazol-1-yl}-acetic acid ethyl ester | 474 | 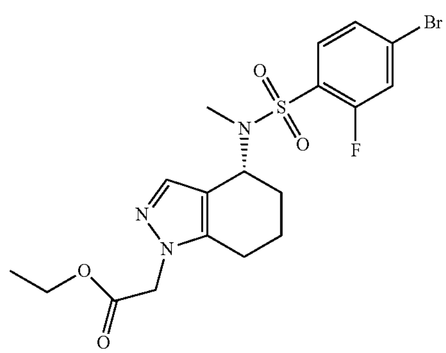 |
| 2-5 | {(R)-4-[(3-Bromo-5-trifluoromethyl-benzenesulfonyl)-methyl-amino]-4,5,6,7-tetrahydro-indazol-1-yl}-acetic acid ethyl ester | 524 | 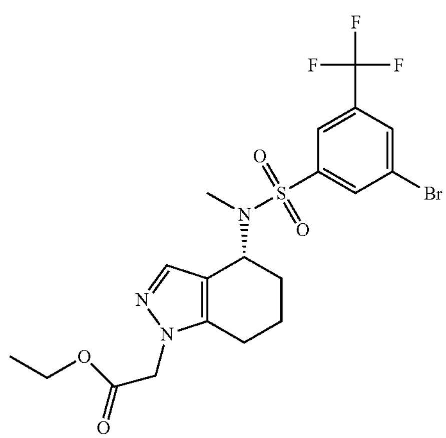 |

| Example No. | Systematic Name | MS (ESI+, M + H) | Structure |
|---|---|---|---|
| 2-6 | {(R)-4-[(3,5-Dibromo-benzenesulfonyl)-methyl-amino]-4,5,6,7-tetrahydro-indazol-1-yl}-acetic acid ethyl ester | 534 | 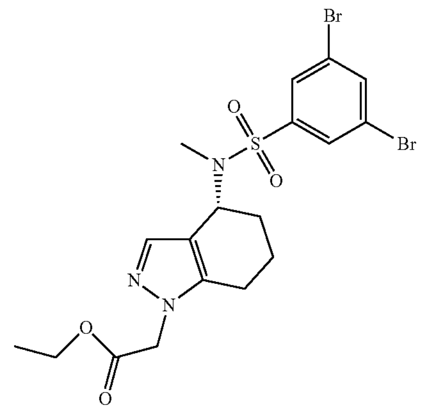 |
| 2-7 | {(R)-4-[(3,5-Di-tert-butyl-benzenesulfonyl)-methyl-amino]-4,5,6,7-tetrahydro-indazol-1-yl}-acetic acid ethyl ester | 490 | 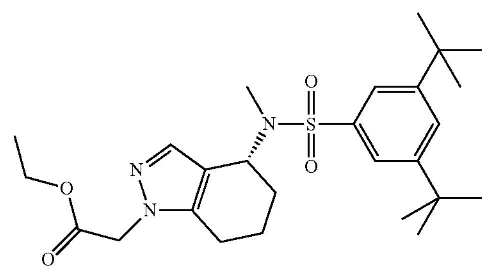 |
| 2-8 | 3-{(R)-4-[(3,5-Bis-trifluoromethyl-benzenesulfonyl)-methyl-amino]-4,5,6,7-tetrahydro-indazol-1-yl}-propionic acid methyl ester | 514 | 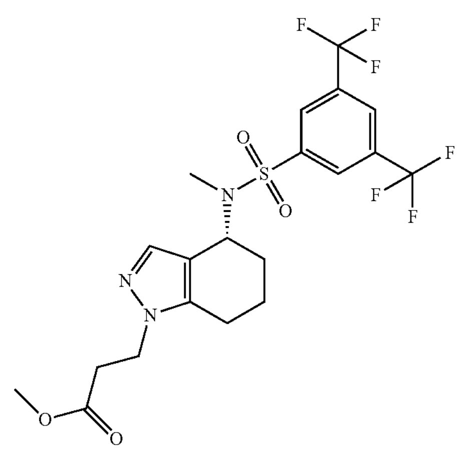 |

Example 2-1a

{(R)-4-[(3,5-Bis-trifluoromethyl-benzenesulfonyl)-methyl-amino]-4,5,6,7-tetrahydro-indazol-1-yl}-acetic acid

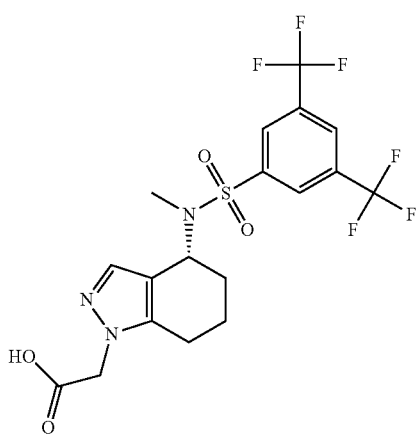

Starting with {(R)-4-[(3,5-bis-trifluoromethyl-benzene-sulfonyl)-methyl-amino]-4,5,6,7-tetrahydro-indazol-1-yl}-acetic acid ethyl ester, using the method analogous to the one described for example 1-1a, {(R)-4-[(3,5-bis-trifluoromethyl-benzene-sulfonyl)-methyl-amino]-4,5,6,7-tetrahydro-indazol-1-yl}-acetic acid (10.2 mg, 68.6%) was obtained as a white solid. $^1$H NMR (400 MHz, CD$_3$OD) δ ppm 8.46 (s, 2H), 8.35 (s, 1H), 6.72 (s, 1H), 5.21 (t, 1H), 4.82 (s, 2H), 2.67 (s, 3H), 2.52 (m, 2H), 2.00-1.64 (m, 4H). MS cald. for C$_{18}$H$_{17}$F$_6$N$_3$O$_4$S 485, obsd. (ESI$^+$) [(M+H)$^+$] 486.

Examples 2-2a to 2-8a

The following examples 2-2a to 2-8a were prepared in an analogous manner as described for example 1-1a using the corresponding esters.

| Example No. | Systematic Name | $^1$H NMR (400 MHz, CD$_3$OD) δ ppm | MS (ESI+, M + H) | Acid structures |
|---|---|---|---|---|
| 2-2a | {(R)-4-[(4-Bromo-2-chloro-benzenesulfonyl)-methyl-amino]-4,5,6,7-tetrahydro-indazol-1-yl}-acetic acid | 8.07 (d, 1 H), 7.94 (s, 1 H), 7.73 (d, 1 H), 7.14 (s, 1 H), 4.99 (t, 1 H), 4.82 (s, 2 H), 2.73 (s, 3 H), 2.56 (s, 2 H), 2.11-2.03 (m, 1 H), 2.01-1.89 (m, 1 H), 1.843-1.73 (m, 2 H) | 462 | |
| 2-3a | {(R)-4-[(2-Chloro-4-trifluoromethyl-benzenesulfonyl)-methyl-amino]-4,5,6,7-tetrahydro-indazol-1-yl}-acetic acid | 8.39 (d, 1 H), 8.06 (s, 1 H), 7.86 (d 1 H), 7.15 (s, 1 H), 5.04 (s, 1 H), 4.81 (s, 2 H), 2.77 (s, 3 H), 2.58 (s, 2 H), 2.08-1.77 (m, 4 H); | 452 | |

-continued

| Example No. | Systematic Name | $^1$H NMR (400 MHz, CD$_3$OD) δ ppm | MS (ESI+, M + H) | Acid structures |
|---|---|---|---|---|
| 2-4a | {(R)-4-[(4-Bromo-2-fluoro-benzenesulfonyl)-methyl-amino]-4,5,6,7-tetrahydro-indazol-1-yl}-acetic acid | 7.89 (t, 1 H), 7.71 (d, 1 H), 7.62 (d, 1 H), 6.89 (s, 1 H), 5.10-5.04 (m, 1 H), 4.74 (s, 2 H), 2.72 (s, 3 H), 2.56 (s, 2 H), 2.11-1.99 (m, 1 H), 1.91-1.69 (m, 3 H) | 446 | 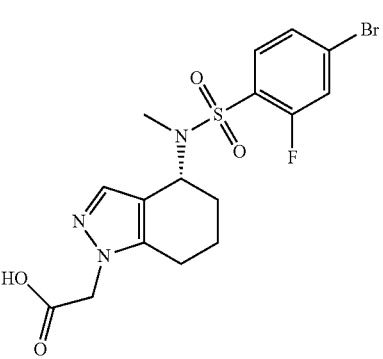 |
| 2-5a | {(R)-4-[(3-Bromo-5-trifluoromethyl-benzenesulfonyl)-methyl-amino]-4,5,6,7-tetrahydro-indazol-1-yl}-acetic acid | 8.38 (s, 1 H), 8.24 (s, 1 H), 8.17 (s, 1 H), 6.65 (s, 1 H), 5.15-5.20 (m, 1 H), 4.85 (s, 2 H), 2.68 (s, 3 H), 2.63-2.48 (m, 2 H), 2.09-1.99 (m, 1 H), 1.89-1.76 (m, 2 H), 1.74-1.62 (m, 1 H) | 496 | 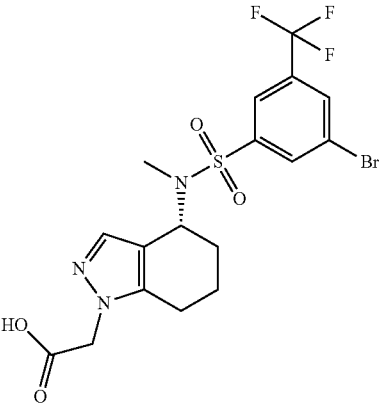 |
| 2-6a | {(R)-4-[(3,5-Dibromo-benzenesulfonyl)-methyl-amino]-4,5,6,7-tetrahydro-indazol-1-yl}-acetic acid | 8.12 (s, 1 H), 8.08 (d, 2 H), 6.61 (s, 1 H), 5.50 (s, 1 H), 5.16-5.07 (m, 1 H), 4.83 (s, 2 H), 2.67 (s, 3 H), 2.63-2.48 (m, 2 H), 2.10-2.00 (m, 2 H), 1.90-1.76 (m, 2 H) | 506 | 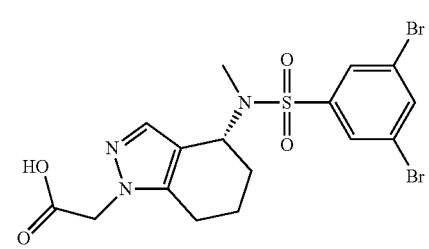 |

| Example No. | Systematic Name | ¹H NMR (400 MHz, CD₃OD) δ ppm | MS (ESI+, M + H) | Acid structures |
|---|---|---|---|---|
| 2-7a | {(R)-4-[(3,5-Di-tert-butyl-benzenesulfonyl)-methyl-amino]-4,5,6,7-tetrahydro-indazol-1-yl}-acetic acid | 7.82 (t, 1 H), 7.75 (d, 2 H), 6.02 (s, 1 H), 5.08-4.99 (m, 1 H), 4.79 (s, 2 H), 2.60 (s, 3 H), 2.57-2.44 (m, 2 H), 2.08-1.95 (m, 1 H), 1.91-1.73 (m, 2 H), 1.71-1.62 (m, 1 H), 1.40-1.37 (s, 18 H) | 462 | |
| 2-8a | 3-{(R)-4-[(3,5-Bis-trifluoromethyl-benzenesulfonyl)-methyl-amino]-4,5,6,7-tetrahydro-indazol-1-yl}-propionic acid | 8.44 (s, 2 H), 8.34 (s, 1 H), 6.57 (s, 1 H), 5.21-5.09 (m, 1 H), 4.18 (t, 2 H) 2.78 (t, 2 H), 2.74-2.51 (m, 5 H), 2.14 (s, 2 H), 2.00 (s, 1 H), 1.83-1.68 (m, 2 H), 1.60 (t, 1 H), | 500 | |

Example 3-1

[4-(3-Ethoxy-5-trifluoromethyl-benzenesulfonylamino)-4,5,6,7-tetrahydro-indazol-1-yl]-acetic acid ethyl ester

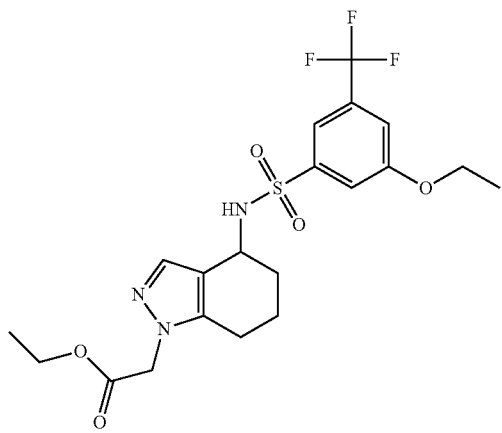

[4-(3-Fluoro-5-trifluoromethyl-benzenesulfonylamino)-4,5,6,7-tetrahydro-indazol-1-yl]-acetic acid ethyl ester (prepared by the method analogous to example 1-1, 200 mg, 0.44 mmol), sodium hydride (60% dispersed in mineral oil, 89 mg, 2.22 mmol) and ethanol (202 mg, 4.4 mmol) were dissolved in N,N-dimethylformamide (2 mL). The mixture was heated in a microwave oven at 150° C. for 40 minutes. The resulting mixture was acidified with 0.1N hydrochloric acid to pH 5 and extracted with ethyl acetate. The organic layers were washed with brine, dried over sodium sulfate and concentrated in vacuo. The residue was purified by flash column (gradient elution, 0-5% methanol in dichloromethane) to afford [4-(3-ethoxy-5-trifluoromethyl-benzenesulfonylamino)-4,5,6,7-tetrahydro-indazol-1-yl]-acetic acid ethyl ester (180 mg, 78%). MS cald. for $C_{20}H_{24}F_3N_3O_5S$ 475, obsd. (ESI⁺) [(M+H)⁺] 476.

Example 3-2 to 3-4

The following examples 3-2 to 3-4 were prepared in an analogous manner as described for example 3-1 using either [4-(5-bromo-6-chloro-pyridine-3-sulfonylamino)-4,5,6,7-tetrahydro-indazol-1-yl]-acetic acid ethyl ester or 4-(3-bromo-5-trifluoromethyl-benzenesulfonylamino)-4,5,6,7-tetrahydro-indazol-1-yl]-acetic acid ethyl ester and the appropriate commercially available alcohols.

| Example No. | Systematic Name | MS (ESI+, M + H) | Structure |
|---|---|---|---|
| 3-2 | [4-(5-Bromo-6-ethoxy-pyridine-3-sulfonylamino)-4,5,6,7-tetrahydro-indazol-1-yl]-acetic acid ethyl ester | 487 | 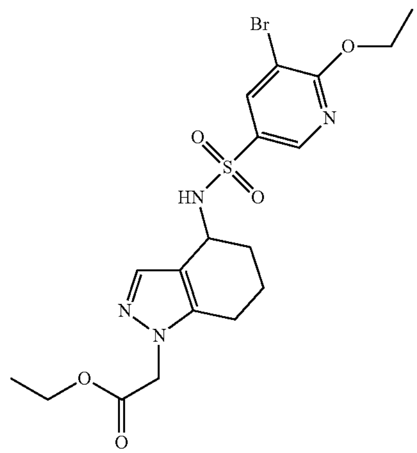 |
| 3-3 | [4-(5-Bromo-6-cyclopentyloxy-pyridine-3-sulfonylamino)-4,5,6,7-tetrahydro-indazol-1-yl]-acetic acid ethyl ester | 527 | 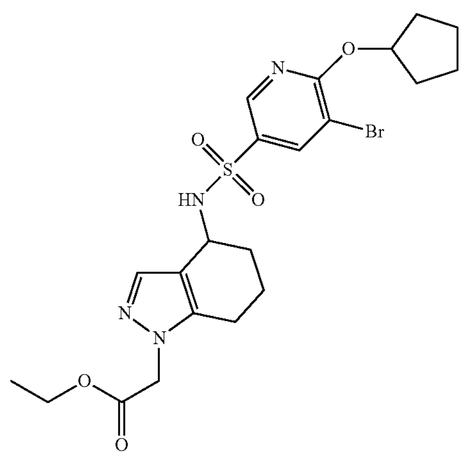 |
| 3-4 | [4-(3-Isopropoxy-5-trifluoromethyl-benzenesulfonylamino)-4,5,6,7-tetrahydro-indazol-1-yl]-acetic acid ethyl ester | 490 | 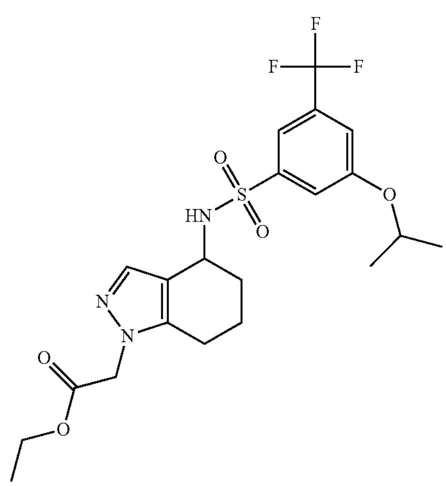 |

Example 3-1a

[4-(3-Ethoxy-5-trifluoromethyl-benzenesulfonylamino)-4,5,6,7-tetrahydro-indazol-1-yl]-acetic acid

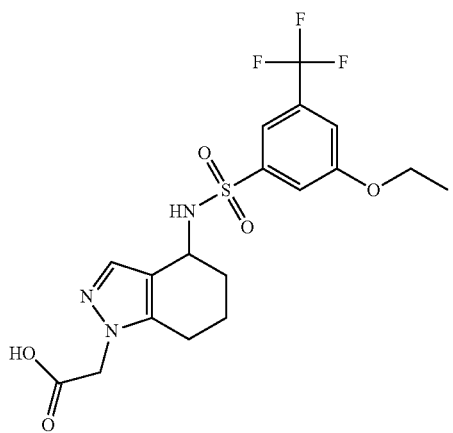

Starting with [4-(3-ethoxy-5-trifluoromethyl-benzenesulfonylamino)-4,5,6,7-tetrahydro-indazol-1-yl]-acetic acid ethyl ester using the method analogous to the one described for example 1-1a, [4-(3-ethoxy-5-trifluoromethyl-benzenesulfonylamino)-4,5,6,7-tetrahydro-indazol-1-yl]-acetic acid (12.0 mg, 50.8%) was obtained as a white solid. $^1$H NMR (400 MHz, CD$_3$OD) δ ppm 7.75 (s, 1H), 7.67 (s, 1H), 7.45 (s, 1H), 6.71 (s, 1H), 4.78 (s, 2H), 4.41 (t, 2H), 4.21 (q, 2H), 2.57 (t, 2H), 1.83-1.78 (m, 4H), 1.47 (s, 3H). MS cald. for C$_{18}$H$_{20}$F$_3$N$_3$O$_5$S 447, obsd. (ESI$^+$) [(M+H)$^+$] 448.

Example 3-2a to 3-4a

The following examples 3-2a to 3-4a were prepared in an analogous manner as described for example 1-1a using the corresponding esters.

| Example No. | Systematic Name | $^1$H NMR (400 MHz, CD$_3$OD) δ ppm | MS (ESI+, M + H) | Structure |
|---|---|---|---|---|
| 3-2a | [4-(5-Bromo-6-ethoxy-pyridine-3-sulfonylamino)-4,5,6,7-tetrahydro-indazol-1-yl]-acetic acid | 8.63 (d, 1 H), 8.36 (s, 1 H), 6.90 (s, 1 H), 4.91 (m, 2 H), 4.56 (q, 2 H), 4.44 (t, 1 H), 2.55 (m, 2 H), 1.95-1.75 (m, 4 H), 1.46 (t, 3 H) | 459 | 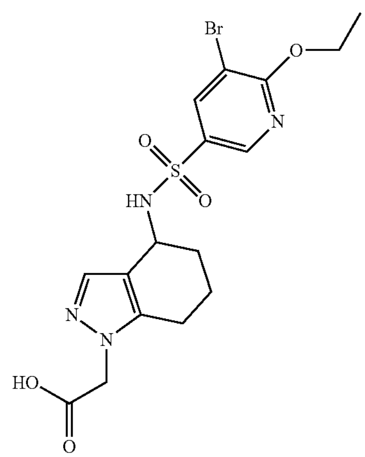 |
| 3-3a | [4-(5-Bromo-6-cyclopentyloxy-pyridine-3-sulfonylamino)-4,5,6,7-tetrahydro-indazol-1-yl]-acetic acid | 8.58 (d, 1 H), 8.31 (d, 1 H), 6.83 (s, 1 H), 5.57 (q, 1 H), 4.76 (s, 2 H), 4.38 (s, 1 H), 2.54 (m, 2 H), 2.01-1.68 (m, 12 H) | 499 | 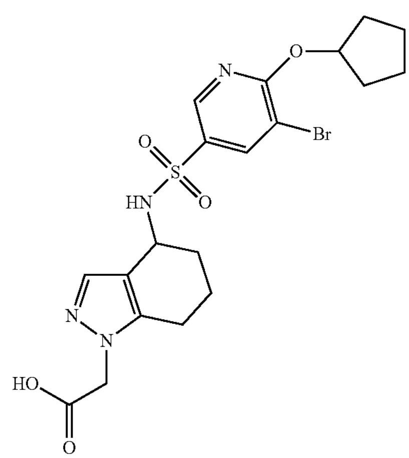 |

-continued

| Example No. | Systematic Name | ¹H NMR (400 MHz, CD$_3$OD) δ ppm | MS (ESI+, M + H) | Structure |
|---|---|---|---|---|
| 3-4a | [4-(3-Isopropoxy-5-trifluoromethyl-benzenesulfonylamino)-4,5,6,7-tetrahydro-indazol-1-yl]-acetic acid | 7.73 (s, 1 H), 7.65 (s, 1 H), 7.43 (s, 1 H), 6.68 (s, 1 H), 4.80 (m, 3 H), 4.41 (t, 1 H), 2.55 (t, 2 H), 2.00-1.72 (m, 4 H), 1.38 (d, 6 H) | 462 | 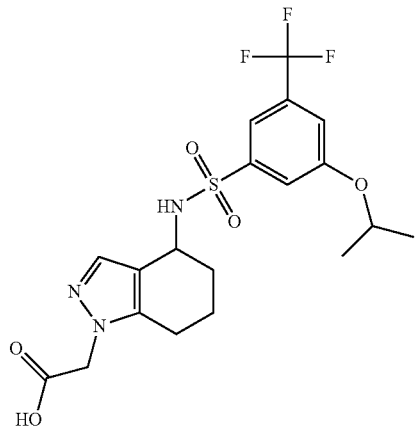 |

Example 4-1

{(R)-4-[(3-Chloro-4-fluoro-benzenesulfonyl)-methyl-amino]-4,5,6,7-tetrahydro-indazol-1-yl}-acetic acid ethyl ester

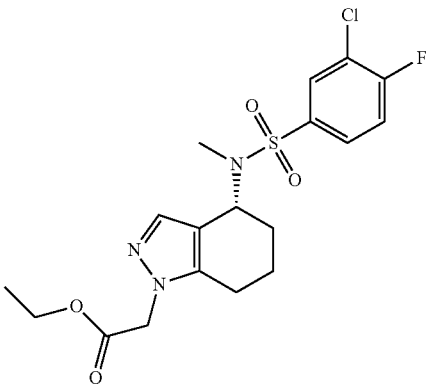

{(R)-4-[(3-Chloro-4-cyclopentyloxy-benzenesulfonyl)-methyl-amino]-4,5,6,7-tetrahydro-indazol-1-yl}-acetic acid ethyl ester

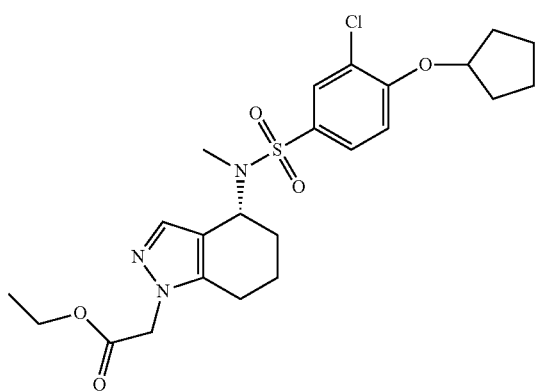

Starting with (R)-[4-(3-chloro-4-fluoro-benzenesulfonylamino)-4,5,6,7-tetrahydro-indazol-1-yl]-acetic acid ethyl ester (prepared by a method analogous to the one described above for example 1-1) and methyl iodide using the method analogous to the one described for example 2-1, {(R)-4-[(3-chloro-4-fluoro-benzenesulfonyl)-methyl-amino]-4,5,6,7-tetrahydro-indazol-1-yl}-acetic acid ethyl ester (56 mg, 83.8%) was prepared as a white solid. MS cald. for $C_{18}H_{21}ClFN_3O_4S$ 429, obsd. (ESI⁺) [(M+H)⁺] 430.

{(R)-4-[(3-Chloro-4-cyclopentyloxy-benzenesulfonyl)-methyl-amino]-4,5,6,7-tetrahydro-indazol-1-yl}-acetic acid ethyl ester

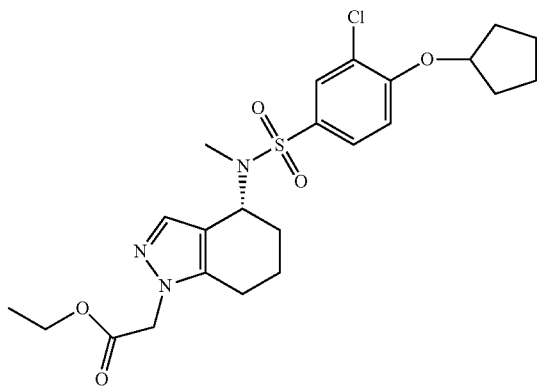

Starting with {(R)-4-[(3-chloro-4-fluoro-benzenesulfonyl)-methyl-amino]-4,5,6,7-tetrahydro-indazol-1-yl}-acetic acid ethyl ester and cyclopentanol using the method analogous to the one described above for example 3-1, {(R)-4-[(3-chloro-4-cyclopentyloxy-benzenesulfonyl)-methyl-amino]-4,5,6,7-tetrahydro-indazol-1-yl}-acetic acid ethyl ester was obtained. MS cald. for $C_{23}H_{30}ClN_3O_5S$ 495, obsd. (ESI$^+$) [(M+H)$^+$] 496.

Example 4-2 to 4-4

The following examples 4-2 to 4-4 were prepared in an analogous manner as described for example 4-1 using [4-(5-bromo-6-chloro-pyridine-3-sulfonylamino)-4,5,6,7-tetrahydro-indazol-1-yl]-acetic acid ethyl ester and the appropriate commercially available alkyl alcohols.

| Example No. | Systematic Name | MS (ESI+, M + H) | Structure |
|---|---|---|---|
| 4-2 | {(R)-4-[(5-Bromo-6-cyclobutoxy-pyridine-3-sulfonyl)-methyl-amino]-4,5,6,7-tetrahydro-indazol-1-yl}-acetic acid ethyl ester | 527 | 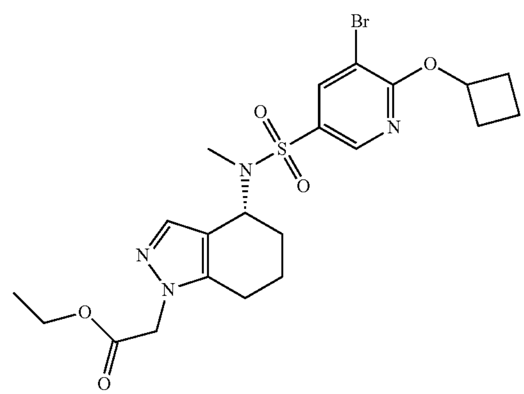 |
| 4-3 | {(R)-4-[(5-Bromo-6-isopropoxy-pyridine-3-sulfonyl)-methyl-amino]-4,5,6,7-tetrahydro-indazol-1-yl}-acetic acid ethyl ester | 515 | 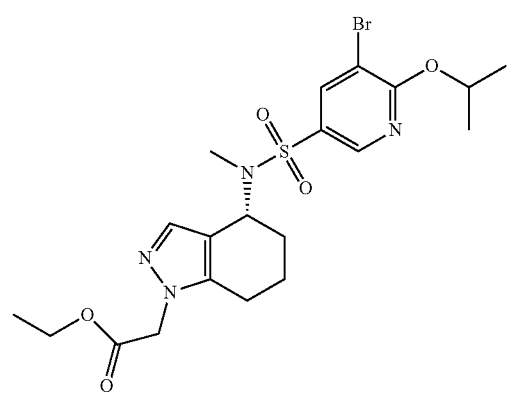 |

| Example No. | Systematic Name | MS (ESI+, M + H) | Structure |
|---|---|---|---|
| 4-4 | ((R)-4-{[5-Bromo-6-(tetrahydro-pyran-4-yloxy)-pyridine-3-sulfonyl]-methyl-amino}-4,5,6,7-tetrahydro-indazol-1-yl)-acetic acid ethyl ester | 557 | 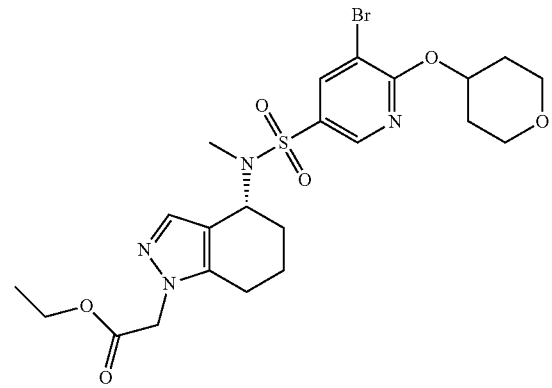 |

Example 4-1a

{(R)-4-[(3-Chloro-4-cyclopentyloxy-benzenesulfonyl)-methyl-amino]-4,5,6,7-tetrahydro-indazol-1-yl}-acetic acid

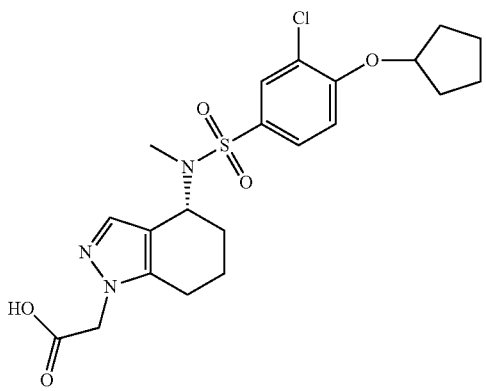

Starting with {(R)-4-[(3-chloro-4-cyclopentyloxy-benzenesulfonyl)-methyl-amino]-4,5,6,7-tetrahydro-indazol-1-yl}-acetic acid ethyl ester using a method analogous to the one described for example 1-1a, {(R)-4-[(3-chloro-4-cyclopentyloxy-benzenesulfonyl)-methyl-amino]-4,5,6,7-tetrahydro-indazol-1-yl}-acetic acid (68.3 mg, 39.8%) was obtained as a white solid. $^1$H NMR (400 MHz, CD$_3$OD) δ ppm 7.90 (d, 1H), 7.83 (dd, 1H), 7.30 (d, 1H), 6.51 (s, 1 H), 5.06 (m, 2H), 4.79 (s, 2H), 2.63 (s, 3H), 2.55 (m, 2H), 2.07-1.68 (m, 12H). MS cald. for C$_{21}$H$_{26}$ClN$_3$O$_5$S 467C$_{22}$H$_{26}$F$_3$N$_3$O$_4$S 485, obsd. (ESI$^+$) [(M+H)$^+$] 468.

Examples 4-2a to 4-4a

The following examples 4-2a to 4-4a were prepared in an analogous manner as described for example 1-1a using the corresponding esters.

| Example No. | Systematic Name | $^1$H NMR (400 MHz, CD$_3$OD) δ ppm | MS (ESI+, M + H) | Structure |
|---|---|---|---|---|
| 4-2a | {(R)-4-[(5-Bromo-6-cyclobutoxy-pyridine-3-sulfonyl)-methyl-amino]-4,5,6,7-tetrahydro-indazol-1-yl}-acetic acid | 8.61 (d, 1 H), 8.38 (d, 1 H), 6.713 (s, 1 H), 5.37 (m, 1 H), 5.12 (q, 1 H), 4.79 (s, 2 H), 2.61 (s, 3 H), 2.54 (m, 4 H), 2.27-1.78 (m, 8 H) | 499 | 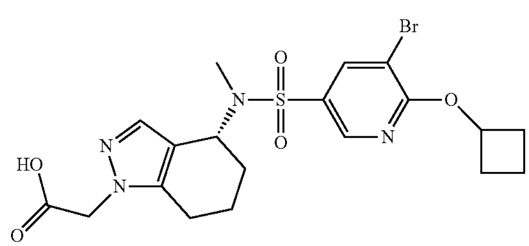 |

-continued

| Example No. | Systematic Name | ¹H NMR (400 MHz, CD₃OD) δ ppm | MS (ESI+, M + H) | Structure |
|---|---|---|---|---|
| 4-3a | {(R)-4-[(5-Bromo-6-isopropoxy-pyridine-3-sulfonyl)-methyl-amino]-4,5,6,7-tetrahydro-indazol-1-yl}-acetic acid | 8.63 (s, 1 H), 8.38 (s, 1 H), 6.73 (s, 1 H), 5.49 (m, 1 H), 5.12 (t, 3 H), 4.78 (s, 2 H), 2.66 (s, 3 H), 2.54 (m, 2 H), 2.07-1.64 (m, 4 H), 1.43 (q, 6 H) | 487 | 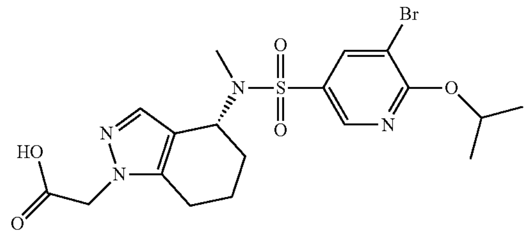 |
| 4-4a* | ((R)-4-{[5-Bromo-6-(tetrahydro-pyran-4-yloxy)-pyridine-3-sulfonyl]-methyl-amino}-4,5,6,7-tetrahydro-indazol-1-yl)-acetic acid | 8.63 (d, 1 H), 8.41 (d, 1 H), 6.73 (s, 1 H), 5.52-5.43 (m, 1 H), 5.16-5.07 (m, 1 H), 4.80 (s, 2 H), 3.99 (t, 2 H), 3.67 (t, 2 H), 2.65 (s, 3 H), 2.60-2.46 (m, 2 H), 2.14-2.06 (m, 2 H), 2.04-1.98 (m, 1 H), 1.89-1.75 (m, 4 H), 1.72-1.60 (m, 1 H) | 529 | 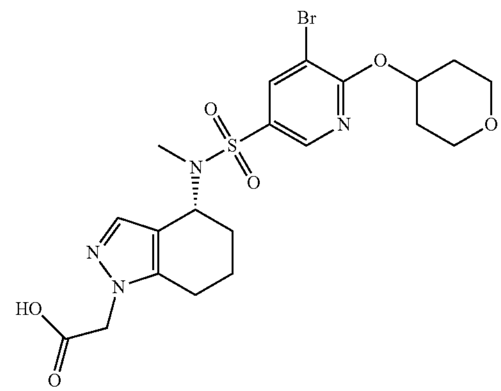 |

*The solvent used for ¹H NMR was CDCl₃.

Example 5-1

[(R)-4-(3-Methanesulfonyl-5-trifluoromethyl-benzenesulfonylamino)-4,5,6,7-tetrahydro-indazol-1-yl]-acetic acid ethyl ester

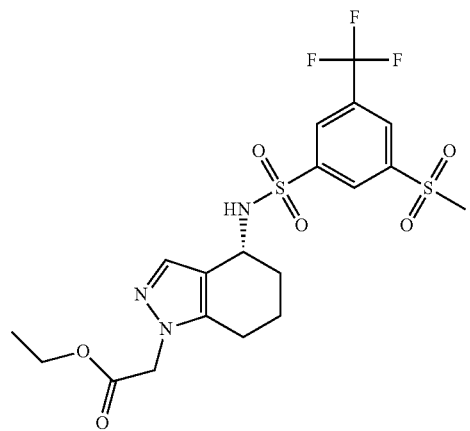

[(R)-4-(3-Bromo-5-trifluoromethyl-benzenesulfonylamino)-4,5,6,7-tetrahydro-indazol-1-yl]acetic acid ethyl ester (118.0 mg, 0.20 mmol), methanesulfinic acid sodium salt (24.5 mg, 0.24 mmol), copper(I) iodide (4.0 mg, 0.02 mmol) and L-proline sodium salt (3.2 mg, 0.04 mmol) were dissolved in dimethyl sulfoxide (1.5 mL) and water (0.3 mL). The mixture was heated in a microwave oven at 150° C. for 30 minutes. The resulting mixture was diluted with water and extracted with ethyl acetate. The organic layer was washed with brine, dried over sodium sulfate, concentrated and purified by column chromatography (gradient elution, 0-5% methanol in dichloromethane) to afford [(R)-4-(3-methanesulfonyl-5-trifluoromethyl-benzenesulfonylamino)-4,5,6,7-tetrahydro-indazol-1-yl]-acetic acid ethyl ester (52.0 mg, 51.1%) as a white solid. MS calcd. for $C_{19}H_{22}F_3N_3O_6S_2$ 509, obsd. (ESI⁺) [(M+H)⁺] 510.

Example 5-1a

[(R)-4-(3-Methanesulfonyl-5-trifluoromethyl-benzenesulfonylamino)-4,5,6,7-tetra-hydro-indazol-1-yl]-acetic acid

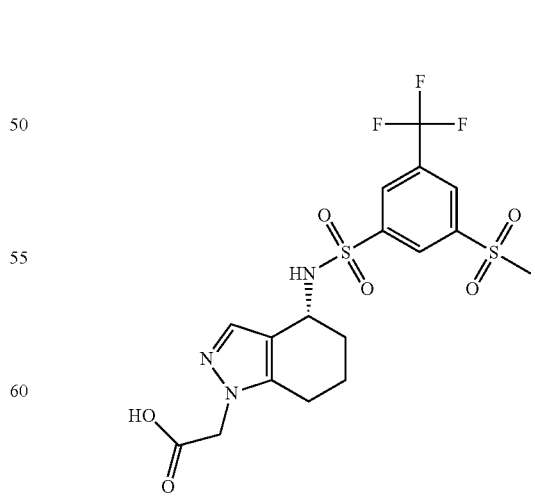

Starting with [(R)-4-(3-methanesulfonyl-5-trifluoromethyl-benzenesulfonylamino)-4,5,6,7-tetrahydro-indazol-1- yl]-acetic acid ethyl ester using the method analogous to the one described for example 1-1a, [(R)-4-(3-methanesulfonyl-5-trifluoromethyl-benzene-sulfonylamino)-4,5,6,7-tetrahydro-indazol-1-yl]-acetic acid (26.8 mg, 54.6%) was obtained as an off-white solid. $^1$H NMR (400 MHz, CD$_3$OD) δ ppm 8.67 (s, 1H), 8.50 (d, 2H), 7.00 (s, 1H), 4.50 (s, 1H), 3.34 (s, 3H), 2.50 (m, 2H), 2.01-1.72 (m, 4H). MS cald. for C$_{17}$H$_{18}$F$_3$N$_3$O$_6$S$_2$ 481, obsd. (ESI$^+$) [(M+H)$^+$] 482.

Example 6-1

{(R)-4-[(3-Methanesulfonyl-5-trifluoromethyl-benzenesulfonyl)-methyl-amino]-4,5,6,7-tetrahydro-indazol-1-yl}-acetic acid ethyl ester

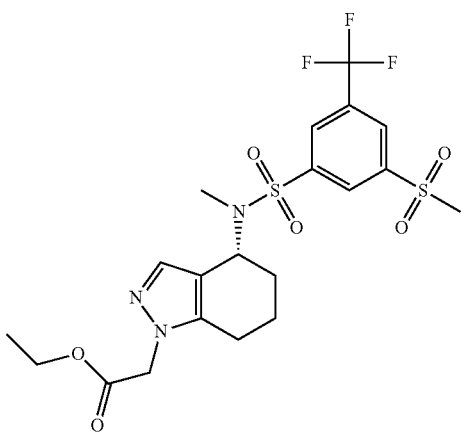

Starting with [(R)-4-(3-methanesulfonyl-5-trifluoromethyl-benzenesulfonylamino)-4,5,6,7-tetrahydro-indazol-1-yl]-acetic acid ethyl ester (example 5-1) and methyl iodide using the method analogous to the one described for example 2-1, {(R)-4-[(3-methanesulfonyl-5-trifluoromethyl-benzene-sulfonyl)-methyl-amino]-4,5,6,7-tetrahydro-indazol-1-yl}-acetic acid ethyl ester was obtained MS cald. for C$_{20}$H$_{24}$F$_3$N$_3$O$_6$S$_2$ 523, obsd. (ESI$^+$) [(M+H)$^+$]: 524.

Example 6-1a

{(R)-4-[(3-Methanesulfonyl-5-trifluoromethyl-benzenesulfonyl)-methyl-amino]-4,5,6,7-tetrahydro-indazol-1-yl}-acetic acid

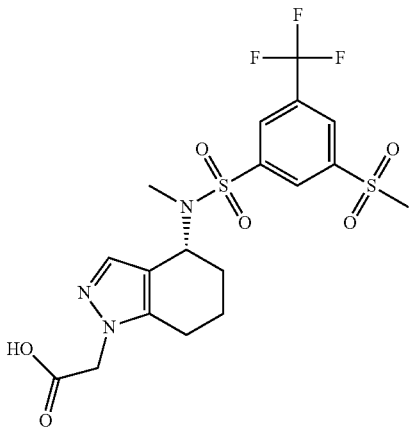

Starting with {(R)-4-[(3-methanesulfonyl-5-trifluoromethyl-benzene-sulfonyl)-methyl-amino]-4,5,6,7-tetrahydro-indazol-1-yl}-acetic acid ethyl ester using the method analogous to the one described for 1-1a, {(R)-4-[(3-methanesulfonyl-5-trifluoromethyl-benzene-sulfonyl)-methyl-amino]-4,5,6,7-tetrahydro-indazol-1-yl}-acetic acid (45 mg, 90%) was prepared as an off-white solid. $^1$H NMR (400 MHz, CD$_3$OD) δ ppm 8.69 (s, 1H), 8.57 (s, 1H), 8.51 (s, 1H), 6.66 (s, 1 H), 5.22 (t, 1H), 4.80 (s, 2H), 3.29 (s, 3H), 2.70 (s, 3H), 2.55 (m, 2H), 2.05-1.66 (m, 4H). MS cald. for C$_{18}$H$_{20}$F$_3$N$_3$O$_6$S$_2$ 495, obsd. (ESI$^+$) [(M+H)$^+$] 496.

Example 7-1

[(R)-4-(3-Ethanesulfonyl-5-trifluoromethyl-benzene-sulfonylamino)-4,5,6,7-tetrahydro-indazol-1-yl]-acetic acid ethyl ester

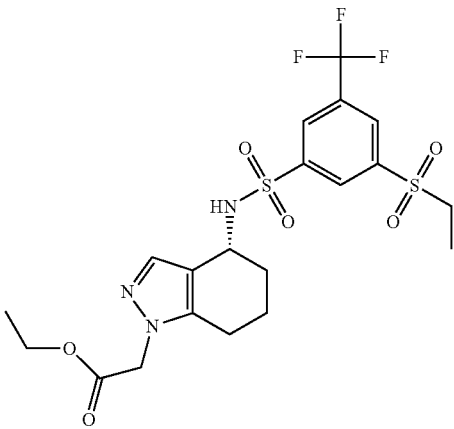

[(R)-4-(3-Ethanesulfanyl-5-trifluoromethyl-benzene-sulfonylamino)-4,5,6,7-tetrahydro-indazol-1-yl-]-acetic acid ethyl ester

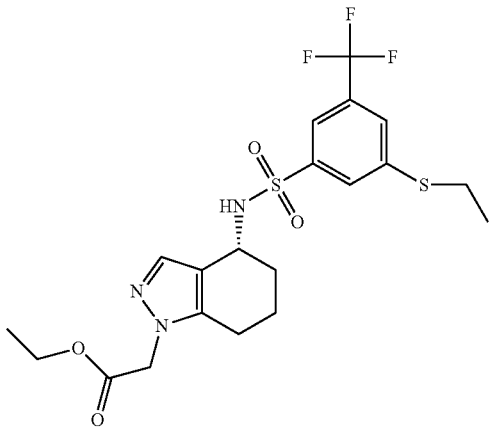

A mixture of [(R)-4-[(3-fluoro-5-trifluoromethyl-benzenesulfonylamino)-4,5,6,7-tetrahydro-indazol-1-yl]-acetic acid ethyl ester (45.0 mg, 0.10 mmol), ethanethiol (50 μL), and potassium carbonate (55.0 mg, 0.40 mmol) in N,N-dimethylformamide (1.0 mL) was heated in a microwave oven at 150° C. for 30 minutes. After cooling to room temperature, the resulting mixture was neutralized with 1N hydrochloric acid and extracted with ethyl acetate (20 mL×3). The combined organic layers were washed with brine (20 mL), dried over sodium sulfate, concentrated to afford [(R)-4-(3-ethanesulfanyl-5-trifluoromethyl-benzenesulfonylamino)-4,5,6,7-tetrahydro-indazol-1-yl]-acetic acid ethyl ester (35.1 mg, 71.2%) as a viscous oil. MS calcd. for $C_{20}H_{24}F_3N_3O_4S_2$ 491, obsd (ESI+) [(M+H)+] 492.

[(R)-4-(3-Ethanesulfonyl-5-trifluoromethyl-benzenesulfonylamino)-4,5,6,7-tetrahydro-indazol-1-yl]-acetic acid ethyl ester

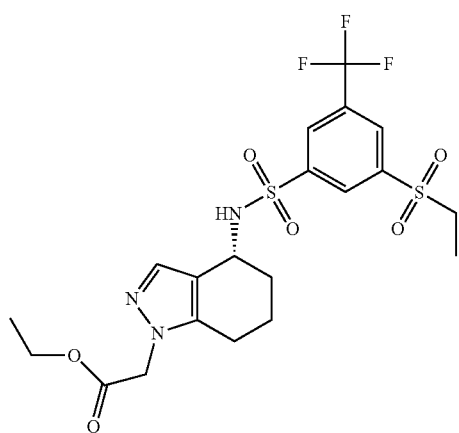

To a solution of {(R)-4-[(3-ethanesulfanyl-5-trifluoromethyl-benzenesulfonyl)-methyl-amino)]-4,5,6,7-tetrahydro-indazol-1-yl}-acetic acid ethyl ester (35.1 mg, 0.07 mmol) in dichloromethane was added m-chloroperoxybenzoic acid (m-CPBA) (34.7 mg, 0.20 mmol) at 0° C. After stirring at room temperature for 3 hours, the resulting mixture was concentrated and purified by column chromatography (5% methanol in dichloromethane) to afford [(R)-4-[(3-ethanesulfonyl-5-trifluoromethyl-benzenesulfonyl)-methyl-amino)]-4,5,6,7-tetrahydro-indazol-1-yl}-acetic acid ethyl ester (20.0 mg, 54.6%) as a semisolid. MS calcd. for $C_{20}H_{24}F_3N_3O_6S_2$ 523, obsd (ESI+) [(M+H)+] 524.

Example 7-2

The following example 7-2 was prepared in an analogous manner as described for example 7-1 using [(R)-4-[(3-fluoro-5-trifluoromethyl-benzenesulfonylamino)-4,5,6,7-tetrahydro-indazol-1-yl]-acetic acid ethyl ester and cyclopentanethiol.

| Example No. | Systematic Name | MS (ESI+, M + H) | Structure |
|---|---|---|---|
| 7-2 | [(R)-4-(3-Cyclopentanesulfonyl-5-trifluoromethyl-benzenesulfonylamino)-4,5,6,7-tetrahydro-indazol-1-yl]-acetic acid ethyl ester | 564 | 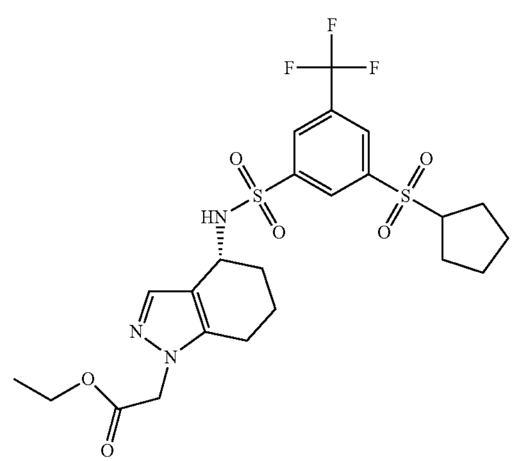 |

Example 7-1a

[(R)-4-(3-Ethanesulfonyl-5-trifluoromethyl-benzene-sulfonylamino)-4,5,6,7-tetrahydro-indazol-1-yl]-acetic acid

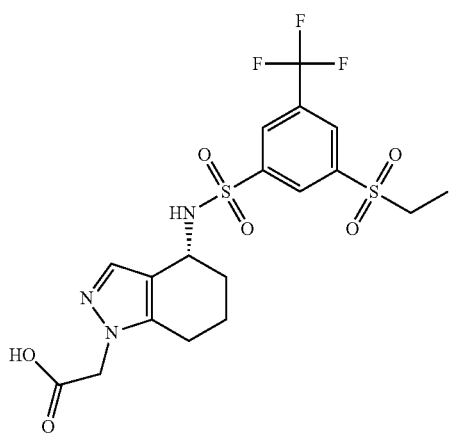

Starting with [(R)-4-(3-ethanesulfonyl-5-trifluoromethyl-benzenesulfonylamino)-4,5,6,7-tetrahydro-indazol-1-yl]-acetic acid ethyl ester using the method analogous to the one described for example 1-1a, [(R)-4-(3-ethanesulfonyl-5-trifluoromethyl-benzenesulfonylamino)-4,5,6,7-tetrahydro-indazol-1-yl]-acetic acid (5.7 mg, 30.2%) was obtained as a white solid. $^1$H NMR (400 MHz, CD$_3$OD) δ ppm 8.66 (s, 1H), 8.54 (s, 1H), 8.49 (s, 1H), 6.80 (s, 1H), 4.80 (s, 2H), 4.52 (s, 1H), 3.50 (q, 2H), 2.60 (m, 2H), 2.01-1.72 (m, 4H), 1.30 (t, 3H). MS cald. for C$_{18}$H$_{20}$F$_3$N$_3$O$_6$S$_2$ 495, obsd. (ESI$^+$) [(M+H)$^+$] 496.

Example 7-2a

The following example 7-2a was prepared in an analogous manner as described for example 1-1a using the corresponding ester.

Example 8-1

{(R)-4-[(3-Ethanesulfinyl-5-trifluoromethyl-benzenesulfonyl)-methyl-amino]-4,5,6,7-tetrahydro-indazol-1-yl}-acetic acid ethyl ester

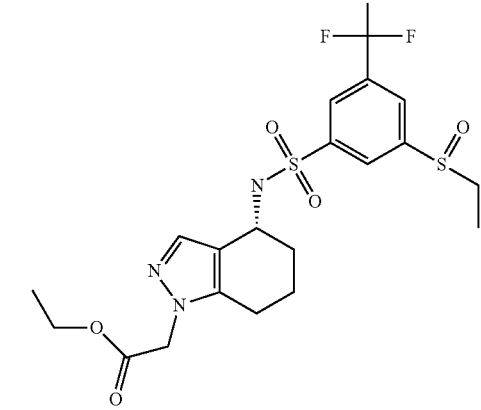

{(R)-4-[(3-Fluoro-5-trifluoromethyl-benzenesulfonyl)-methyl-amino]-4,5,6,7-tetra-hydro-indazol-1-yl}-acetic acid ethyl ester

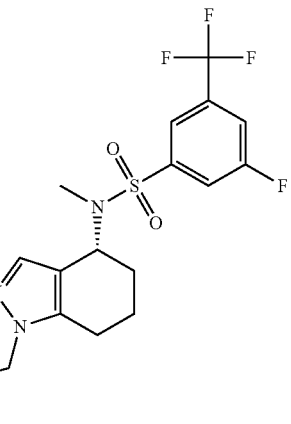

| Example No. | Systematic Name | $^1$H NMR (400 MHz, CD$_3$OD) δ ppm | MS (ESI+, M + H) | Structure |
|---|---|---|---|---|
| 7-2a | [(R)-4-(3-Cyclopentane-sulfonyl-5-trifluoromethyl-benzenesulfonyl-amino)-4,5,6,7-tetrahydro-indazol-1-yl]-acetic acid | 8.62 (s, 1 H), 8.52 (s, 1 H), 8.45 (s, 1 H), 6.78 (s, 1 H), 4.98 (s, 2 H), 4.52 (t, 1 H), 3.82 (m, 1 H), 2.50 (m, 2 H), 2.06-1.82 (m, 4 H) | 536 | 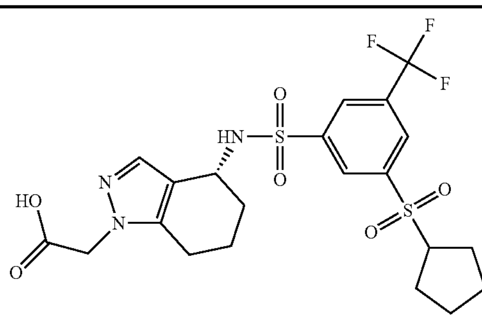 |

Starting with [(R)-4-(3-fluoro-5-trifluoromethyl-benzenesulfonylamino)-4,5,6,7-tetrahydro-indazol-1-yl]-acetic acid ethyl ester (prepared by a method described above for example 1-1) and methyl iodide, using the method analogous to the one described for example 2-1, {(R)-4-[(3-fluoro-5-trifluoro-methyl-benzenesulfonyl)-methyl-amino]-4,5,6,7-tetrahydro-indazol-1-yl}-acetic acid ethyl ester (500 mg, 94%) was prepared as a white solid. LC-MS cald. for $C_{19}H_{21}F_4N_3O_4S$ 463, obsd. (ESI+) [(M+H)+] 464.

{(R)-4-[(3-Ethylsulfanyl-5-trifluoromethyl-benzenesulfonyl)-methyl-amino]-4,5,6,7-tetrahydro-indazol-1-yl}-acetic acid ethyl ester

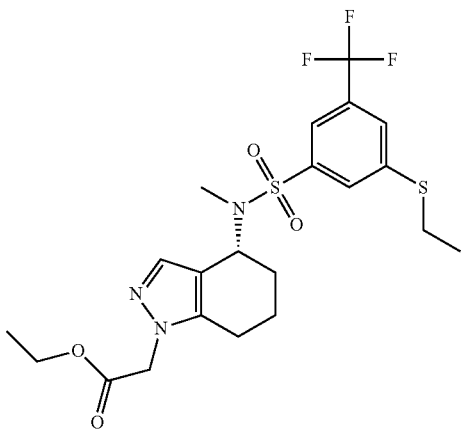

Starting with {(R)-4-[(3-fluoro-5-trifluoromethyl-benzenesulfonyl)-methyl-amino]-4,5,6,7-tetrahydro-indazol-1-yl}-acetic acid ethyl ester and ethanethiol using a method analogous to the one described for the 1st step of example 7-1, {(R)-4-[(3-ethylsulfanyl-5-trifluoromethyl-benzenesulfonyl)-methyl-amino]-4,5,6,7-tetrahydro-indazol-1-yl}-acetic acid ethyl ester (136 mg, 86%) was obtained as a white solid. MS cald. for $C_{21}H_{26}F_3N_3O_4S_2$ 505, obsd. (ESI+) [(M+H)+] 506.

{(R)-4-[(3-Ethanesulfinyl-5-trifluoromethyl-benzenesulfonyl)-methyl-amino]-4,5,6,7-tetrahydro-indazol-1-yl}-acetic acid ethyl ester

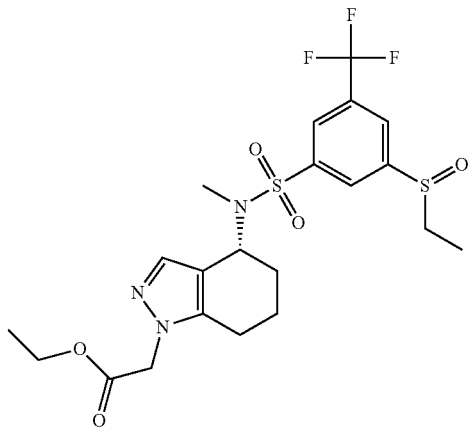

To a solution of {(R)-4-[(3-ethylsulfanyl-5-trifluoromethyl-benzenesulfonyl)-methyl-amino]-4,5,6,7-tetrahydro-indazol-1-yl}-acetic acid ethyl ester (50.6 mg, 0.10 mmol) in dichloromethane was added 3-chloro-benzenecarboperoxoic acid (m-CPBA) (19.1 mg, 0.11 mmol) at 0° C. After stirring at room temperature for 3 hours, the resulting mixture was concentrated in vacuo. The residue was purified by flash column (gradient elution, 5% methanol in dichloromethane) to afford {(R)-4-[(3-ethanesulfinyl-5-trifluoromethyl-benzenesulfonyl)-methyl-amino]-4,5,6,7-tetrahydro-indazol-1-yl}-acetic acid ethyl ester (39.6 mg, 76.2%) as a semisolid. MS cald. for $C_{21}H_{26}F_3N_3O_5S_2$ 521, obsd. (ESI+) [(M+H)+] 522.

Example 8-1a

{(R)-4-[(3-Ethanesulfinyl-5-trifluoromethyl-benzenesulfonyl)-methyl-amino]-4,5,6,7-tetrahydro-indazol-1-yl}-acetic acid

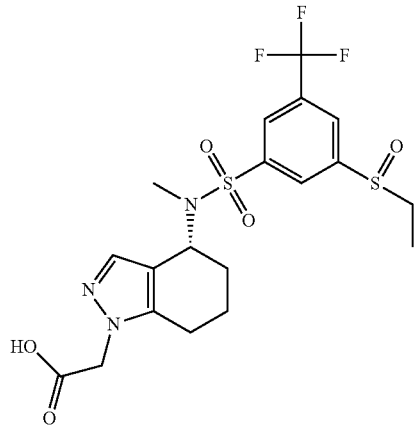

Starting with {(R)-4-[(3-ethylsulfanyl-5-trifluoromethyl-benzenesulfonyl)-methyl-amino]-4,5,6,7-tetrahydro-indazol-1-yl}-acetic acid ethyl ester using the method analogous to the one described for example 1-1a, {(R)-4-[(3-ethanesulfinyl-5-trifluoromethyl-benzenesulfonyl)-methyl-amino]-4,5,6,7-tetrahydro-indazol-1-yl}-acetic acid (13 mg, 34.6%) was obtained as a white solid. 1H NMR (400 MHz, CD3OD) δ ppm 8.50 (s, 1H), 8.35 (d, 2H), 6.57 (d, 1H), 5.20 (t, 1H), 4.82 (s, 2H), 3.27-3.16 (m, 1H), 2.99-2.88 (m, 1H), 2.71 (s, 3H), 2.62-2.48 (m, 2 H), 2.09-1.99 (m, 1H), 1.88-1.76 (m, 2H), 1.73-1.63 (m, 1H), 1.17 (t, 3H). MS cald. for $C_{19}H_{22}F_3N_3O_5S_2$ 493, obsd. (ESI+) [(M+H)+] 494.

Example 9-1

{(R)-4-[(3-Cyclopentylsulfanyl-5-trifluoromethyl-benzenesulfonyl)-methyl-amino]-4,5,6,7-tetrahydro-indazol-1-yl}-acetic acid ethyl ester

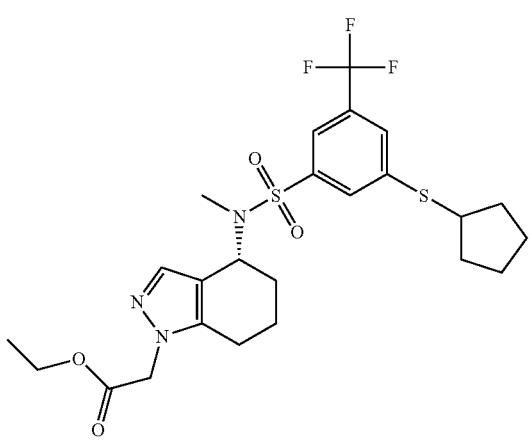

Starting with {(R)-4-[(3-fluoro-5-trifluoromethyl-benzenesulfonyl)-methyl-amino]-4,5,6,7-tetrahydro-indazol-1-yl}-acetic acid ethyl ester (1st step intermediate of example 8-1) and cyclopentanethiol using the method analogous to the method analogous to the one described for the 1st step of example 7-1, {(R)-4-[(3-Cyclopentylsulfanyl-5-trifluoromethyl-benzenesulfonyl)-methyl-amino]-4,5,6,7-tetrahydro-indazol-1-yl}-acetic acid ethyl ester (20.2 mg, 83%) was obtained. MS cald. for $C_{24}H_{30}F_3N_3O_4S_2$ 545, obsd. (ESI$^+$) [(M+H)$^+$] 546.

Example 9-1a

{(R)-4-[(3-Cyclopentylsulfanyl-5-trifluoromethyl-benzenesulfonyl)-methyl-amino]-4,5,6,7-tetrahydro-indazol-1-yl}-acetic acid

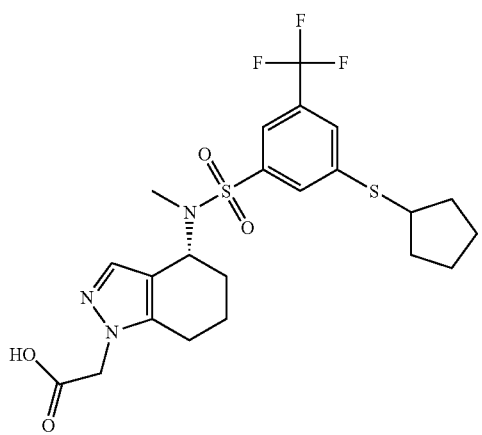

Starting with {(R)-4-[(3-cyclopentyl-sulfanyl-5-trifluoromethyl-benzenesulfonyl)-methyl-amino]-4,5,6,7-tetra-hydro-indazol-1-yl}-acetic acid ethyl ester using the method analogous to the one described for example 1-1a, {(R)-4-[(3-cyclopentylsulfanyl-5-trifluoromethyl-benzenesulfonyl)-methyl-amino]-4,5,6,7-tetrahydro-indazol-1-yl}-acetic acid (13.2 mg, 68.7%) was obtained as a light yellow solid. $^1$H NMR (400 MHz, CD$_3$OD) δ ppm 8.04 (s, 1H), 7.91 (d, 2H), 6.51 (s, 1H), 5.13 (s, 1H), 4.81 (s, 2H), 3.90 (m, 1H), 2.67 (q, 2H), 2.56 (m, 2H), 2.23-2.04 (m, 4H), 1.83-1.63 (m, 8H). MS cald. for $C_{22}H_{26}F_3N_3O_4S_2$ 517, obsd. (ESI$^+$) [(M+H)$^+$] 518.

Example 10-1

{(R)-4-[(3-Ethanesulfonyl-5-trifluoromethyl-benzenesulfonyl)-methyl-amino]-4,5,6,7-tetrahydro-indazol-1-yl}-acetic acid ethyl ester

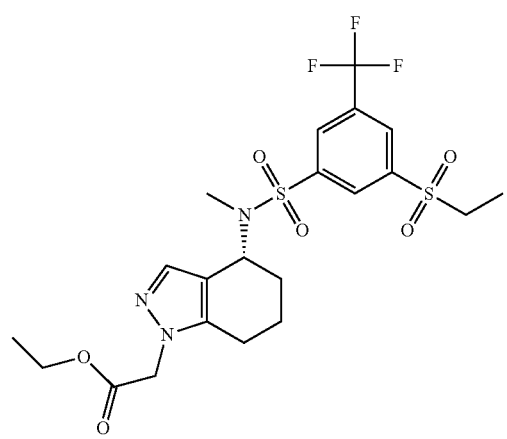

Starting with {(R)-4-[(3-ethylsulfanyl-5-trifluoromethyl-benzenesulfonyl)-methyl-amino]-4,5,6,7-tetrahydro-indazol-1-yl}-acetic acid ethyl ester (1st step intermediate of example 8-1) using the method analogous to the one described for example 7-1, {(R)-4-[(3-ethanesulfonyl-5-trifluoromethyl-benzenesulfonyl)-methyl-amino]-4,5,6,7-tetrahydro-indazol-1-yl}-acetic acid ethyl ester was obtained as a white solid. MS cald. for $C_{21}H_{26}F_3N_3O_6S_2$ 537, obsd. (ESI$^+$) [(M+H)$^+$] 538.

Example 10-2 to 10-7

The following examples 10-2 to 10-7 were prepared in an analogous manner as described for example 10-1 using [(R)-4-[(3-fluoro-5-trifluoromethyl-benzenesulfonylamino)-4,5,6,7-tetrahydro-indazol-1-yl]-acetic acid ethyl ester or (R)-3-[4-(3-fluoro-5-trifluoromethyl-benzenesulfonylamino)-4,5,6,7-tetrahydro-indazol-1-yl]-propionic acid methyl ester, methyl iodide, and the commercially available alkyl thiols.

| Example No. | Systematic Name | MS (ESI+, M + H) | Structure |
|---|---|---|---|
| 10-2 | {(R)-4-[(3-Cyclopentanesulfonyl-5-trifluoromethyl-benzenesulfonyl)-methyl-amino]-4,5,6,7-tetrahydro-indazol-1-yl}-acetic acid ethyl ester | 578 | 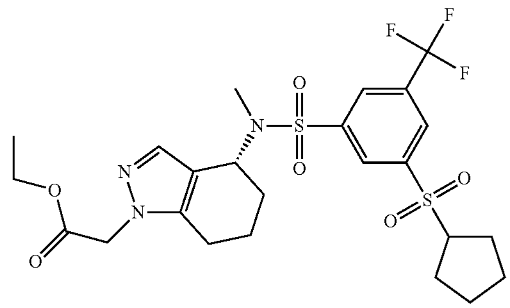 |
| 10-3 | ((R)-4-{Methyl-[3-(propane-2-sulfonyl)-5-trifluoromethyl-benzenesulfonyl]-amino}-4,5,6,7-tetrahydro-indazol-1-yl)-acetic acid ethyl ester | 552 | 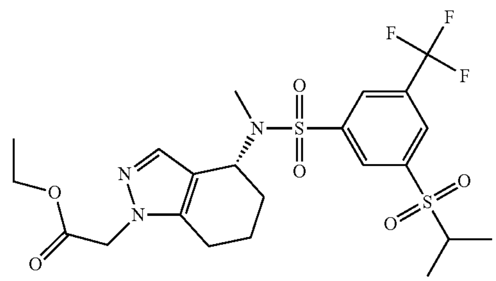 |
| 10-4 | ((R)-4-{Methyl-[3-(2-methyl-propane-2-sulfonyl)-5-trifluoromethyl-benzenesulfonyl]-amino}-4,5,6,7-tetrahydro-indazol-1-yl)-acetic acid ethyl ester | 566 | 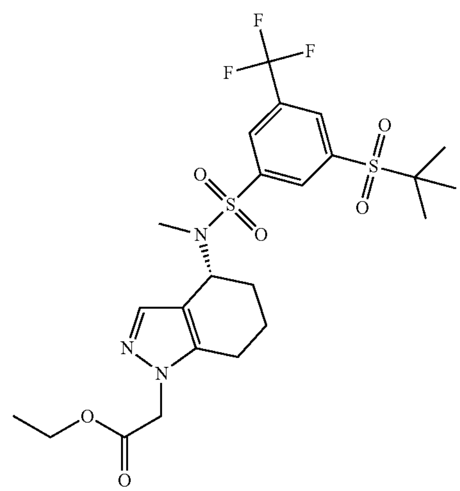 |
| 10-5 | 3-((R)-4-{Methyl-[3-(propane-2-sulfonyl)-5-trifluoromethyl-benzenesulfonyl]-amino}-4,5,6,7-tetrahydro-indazol-1-yl)-propionic acid methyl ester | 552 | 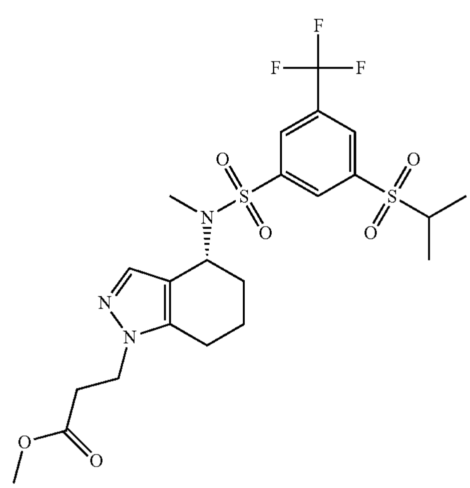 |

| Example No. | Systematic Name | MS (ESI+, M + H) | Structure |
|---|---|---|---|
| 10-6 | 3-{(R)-4-[(3-Cyclopentanesulfonyl-5-trifluoromethyl-benzenesulfonyl)-methyl-amino]-4,5,6,7-tetrahydro-indazol-1-yl}-propionic acid ethyl ester | 578 | 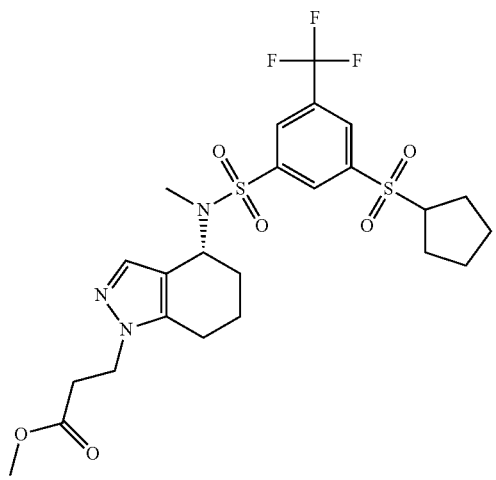 |
| 10-7 | 3-((R)-4-{Methyl-[3-(2-methyl-propane-2-sulfonyl)-5-trifluoromethyl-benzenesulfonyl]-amino}-4,5,6,7-tetrahydro-indazol-1-yl)-propionic acid methyl ester | 566 | 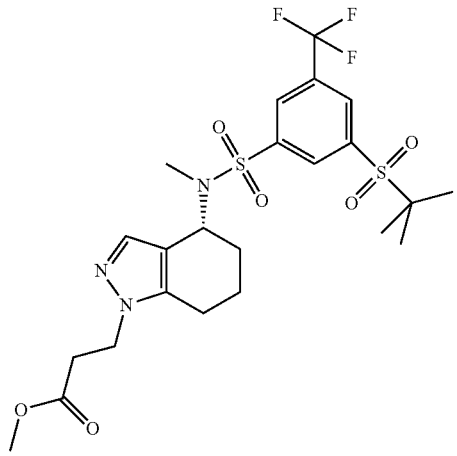 |

Example 10-1a

{(R)-4-[(3-Ethanesulfonyl-5-trifluoromethyl-benzenesulfonyl)-methyl-amino]-4,5,6,7-tetrahydro-indazol-1-yl}-acetic acid

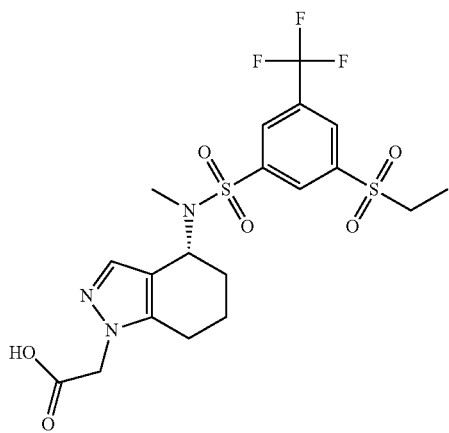

Starting with {(R)-4-[(3-ethylsulfonyl-5-trifluoromethyl-benzenesulfonyl)-methyl-amino]-4,5,6,7-tetrahydro-indazol-1-yl}-acetic acid ethyl ester using the method analogous to the one described for example 1-1a, {(R)-4-[(3-ethanesulfonyl-5-trifluoromethyl-benzenesulfonyl)-methyl-amino]-4,5,6,7-tetrahydro-indazol-1-yl}-acetic acid (10.9 mg, 36.6%) was obtained as a white solid. $^1$H NMR (400 MHz, CD$_3$OD) δ ppm 8.62 (s, 1H), 8.52 (d, 2H), 6.64 (s, 1H), 5.21 (q, 1H), 4.82 (s, 2H), 3.37 (q, 2H), 2.68 (s, 3H), 2.50 (m, 2H), 2.06-1.82 (m, 4H), 1.27 (t, 3 H). MS cald. for C$_{19}$H$_{22}$F$_3$N$_3$O$_6$S$_2$ 509, obsd. (ESI$^+$) [(M+H)$^+$] 510.

Example 10-2a to 10-7a

The following examples 10-2a to 10-7a were prepared in an analogous manner as described for example 1-1a using the corresponding ester.

| Example No. | Systematic Name | $^1$H NMR (400 MHz, CD$_3$OD) δ ppm | MS (ESI+, M + H) | Systematic Name |
|---|---|---|---|---|
| 10-2a | {(R)-4-[(3-Cyclopentanesulfonyl-5-trifluoromethyl-benzenesulfonyl)-methyl-amino]-4,5,6,7-tetrahydro-indazol-1-yl}-acetic acid | 8.60 (s, 1 H), 8.51 (s, 1 H), 8.48 (s, 1 H), 6.45 (s, 1 H), 5.20 (q, 1 H), 4.53 (s, 2 H), 3.87 (m, 1 H), 2.71 (s, 3 H), 2.50 (m, 2 H), 2.02-1.65 (m, 12 H) | 550 | |
| 10-3a | ((R)-4-{Methyl-[3-(propane-2-sulfonyl)-5-trifluoromethyl-benzenesulfonyl]-amino}-4,5,6,7-tetrahydro-indazol-1-yl)-acetic acid | 8.57 (s, 1 H), 8.53 (s, 1 H), 8.46 (s, 1 H), 6.67 (s, 1 H), 5.20 (m, 1 H), 4.82 (s, 2 H), 3.56 (m, 1 H), 2.68 (s, 3 H), 2.54 (m, 2 H), 2.04-1.64 (m, 4 H), 1.28 (d, 6 H) | 524 | |

-continued

| Example No. | Systematic Name | ¹H NMR (400 MHz, CD₃OD) δ ppm | MS (ESI+, M + H) | Systematic Name |
|---|---|---|---|---|
| 10-4a | ((R)-4-{Methyl-[3-(2-methyl-propane-2-sulfonyl)-5-trifluoromethyl-benzenesulfonyl]-amino}-4,5,6,7-tetrahydro-indazol-1-yl)-acetic acid | 8.54 (d, 2 H), 8.39 (s, 1 H), 6.59 (s, 1 H), 5.15 (t, 1 H), 4.74 (s, 2 H), 2.69 (s, 3 H), 2.59-2.44 (m, 2 H), 2.06-1.96 (m, 1 H), 1.89-1.74 (m, 3 H), 1.32 (s, 9 H) | 538 | 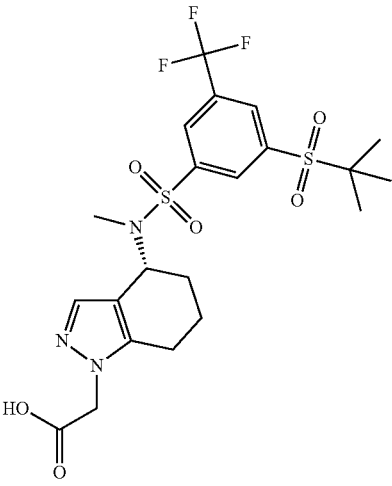 |
| 10-5a | 3-((R)-4-{Methyl-[3-(propane-2-sulfonyl)-5-trifluoromethyl-benzenesulfonyl]-amino}-4,5,6,7-tetrahydro-indazol-1-yl)-propionic acid | 8.59 (s, 1 H), 8.55 (s, 1 H), 8.48 (s, 1 H), 6.59 (s, 1 H), 5.21-5.151 (m, 1 H), 4.23 (t, 2 H), 3.60-3.52 (m, 1 H), 2.79 (t, 2 H), 2.74-2.56 (m, 5 H), 2.09-2.00 (m, 1 H), 1.86-1.76 (m, 2 H), 1.72-1.64 (m, 1 H), 1.33-1.29 (m, 6 H) | 538 | 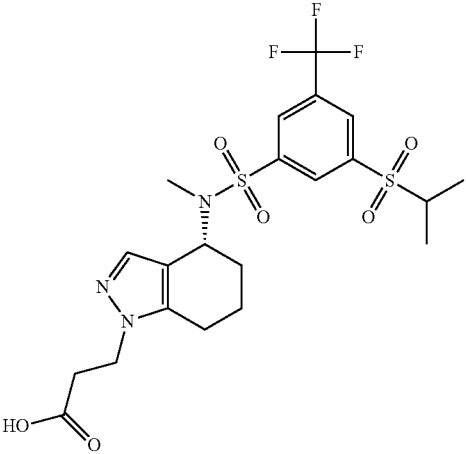 |

-continued

| Example No. | Systematic Name | ¹H NMR (400 MHz, CD₃OD) δ ppm | MS (ESI+, M + H) | Systematic Name |
|---|---|---|---|---|
| 10-6a | 3-{(R)-4-[(3-Cyclopentanesulfonyl-5-trifluoromethyl-benzenesulfonyl)-methyl-amino]-4,5,6,7-tetrahydro-indazol-1-yl}-propionic acid | 8.61 (s, 1 H), 8.52 (s, 2 H), 6.58 (s, 1 H), 5.20 (t, 1 H), 4.23 (s, 2 H), 3.92 (m, 3 H), 2.80-2.60 (m, 7 H), 2.06-1.66 (m, 10 H). | 564 | |
| 10-7a | 3-((R)-4-{Methyl-[3-(2-methyl-propane-2-sulfonyl)-5-trifluoromethyl-benzenesulfonyl]-amino}-4,5,6,7-tetrahydro-indazol-1-yl)-propionic acid | 8.57 (d, 2 H), 8.42 (s, 1 H), 6.58 (s, 1 H), 5.17 (t, 1 H), 4.23 (t, 2 H), 3.92 (m, 3 H), 2.83-2.60 (m, 5 H), 2.05-1.66 (m, 4 H), 1.38 (s, 9 H) | 552 | |

Example 11-1

{(R)-4-[3-(1-Methyl-cyclopropyl)-5-trifluoromethyl-benzenesulfonylamino]-4,5,6,7-tetrahydro-indazol-1-yl}-acetic acid ethyl ester

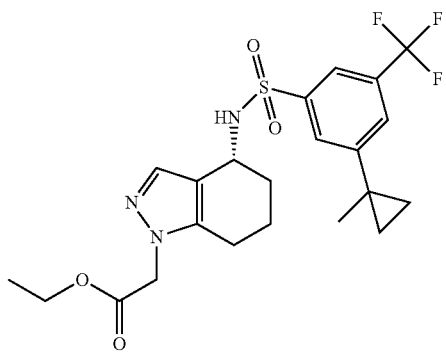

[(R)-4-(3-Isopropenyl-5-trifluoromethyl-benzenesulfonylamino)-4,5,6,7-tetrahydro-indazol-1-yl]-acetic acid ethyl ester

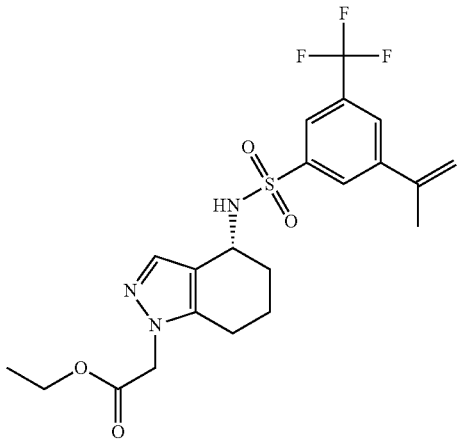

To a solution of [(R)-4-(3-bromo-5-trifluoromethyl-benzenesulfonylamino)-4,5,6,7-tetrahydro-indazol-1-yl]-acetic acid ethyl ester (Example 1-1, 100 mg, 0.196 mmol) in N,N-dimethylformamide (2 mL) in a microwave vial (5 mL), tetrakis(triphenylphosphine)palladium(0) (22 mg, 0.19 mmol), potassium tert-butoxide (45 mg, 0.4 mmol) and isopropenyl boronic acid pinacol ester (55 µl, 0.294 mmol) were added. After being heated in a microwave oven (130° C., 15 min.), the mixture was poured into aq. ammonium chloride (10 mL) and extracted with dichloromethane (20 mL×3). The combined organic layers were washed with water (10 mL×3) and brine (20 mL), dried over sodium sulfate and concentrated in vacuo. The residue was purified by column chromatography (gradient elution, 0-5% methanol in dichloromethane) to afford [(R)-4-(3-isopropenyl-5-trifluoromethyl-benzene-sulfonylamino)-4,5,6,7-tetrahydro-indazol-1-yl]-acetic acid ethyl ester (34 mg, 36.8%) as a white solid, MS calcd. for $C_{21}H_{24}F_3N_3O_4S$ 471, obsd. (ESI$^+$) [(M+H)$^+$] 472.

{(R)-4-[3-(1-Methyl-cyclopropyl)-5-trifluoromethyl-benzenesulfonylamino]-4,5,6,7-tetrahydro-indazol-1-yl}-acetic acid ethyl ester

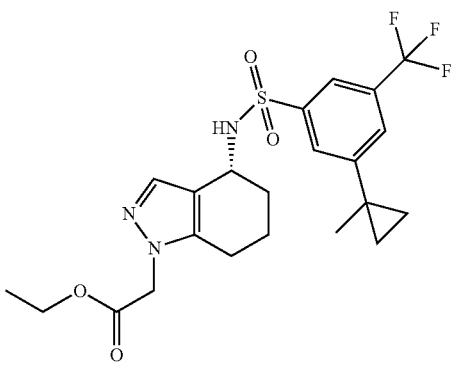

To a solution of diiodomethane (1.0 mL, 16 mmol) in toluene (10 mL) was added diethylzinc (15% in hexane, 10 mL, 8.8 mmol) under an argon atmosphere at 0° C. and the mixture was stirred for 15 minutes. To the mixture was added [(R)-4-(3-isopropenyl-5-trifluoromethyl-benzenesulfonylamino)-4,5,6,7-tetrahydro-indazol-1-yl]-acetic acid ethyl ester (0.2 g, 0.46 mmol) in toluene (4 ml) and the mixture was stirred at 0° C. and then room temperature for 4 hours. The mixture was poured into aqueous ammonium chloride (20 mL) and extracted with dichloromethane (30 mL×3). The combined organic layers were washed with water (20 mL×3), then brine (30 mL), dried over sodium sulfate, concentrated and purified by preparative HPLC to afford {(R)-4-[3-(1-methyl-cyclopropyl)-5-trifluoromethyl-benzenesulfonylamino]-4,5,6,7-tetrahydro-indazol-1-yl}-acetic acid ethyl ester (40 mg, 18%) as a white solid. MS calcd. for $C_{22}H_{26}F_3N_3O_4S$ 485, obsd. (ESI$^+$) [(M+H)$^+$] 486.

Example 11-1a

{(R)-4-[3-(1-Methyl-cyclopropyl)-5-trifluoromethyl-benzenesulfonylamino]-4,5,6,7-tetrahydro-indazol-1-yl}-acetic acid

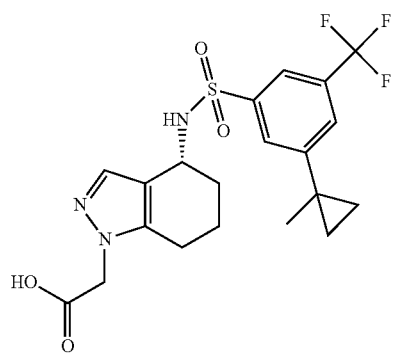

Starting with {(R)-4-[3-(1-methyl-cyclopropyl)-5-trifluoromethyl-benzenesulfonylamino]-4,5,6,7-tetrahydro-indazol-1-yl}-acetic acid ethyl ester using the method analogous to the one described for example 1-1a, {(R)-4-[3-(1-methyl-cyclopropyl)-5-trifluoromethyl-benzenesulfonyl-amino]-4,5,6,7-tetrahydro-indazol-1-yl}-acetic acid (10 mg, 53%) was obtained as a white solid. $^1$H NMR (400 MHz, CD$_3$OD) δ ppm 8.04 (s, 1H), 8.00 (s, 1 H), 7.81 (s, 1H), 6.59 (s, 1H), 4.79 (s, 2H), 4.40 (t, 1H), 2.60-2.45 (m, 2H), 1.93-1.74 (m, 4 H), 1.50 (s, 3H), 0.94 (m, 4H). MS cald. for $C_{20}H_{22}F_3N_3O_4S$ 457, obsd. (ESI$^+$) [(M+H)$^+$] 458.

Example 12-1

(R)-[4-(3-Isopropyl-5-trifluoromethyl-benzenesulfonylamino)-4,5,6,7-tetrahydro-indazol-1-yl]-acetic acid ethyl ester

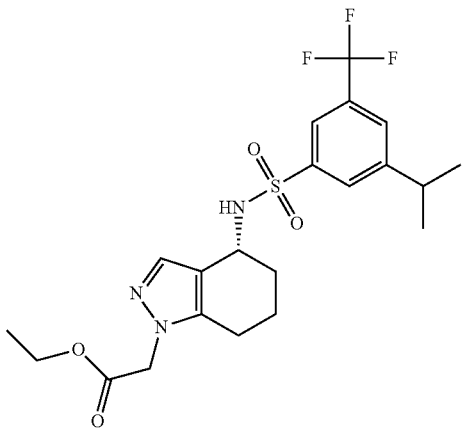

A solution of (R)-[4-(3-isopropenyl-5-trifluoromethyl-benzenesulfonylamino)-4,5,6,7-tetrahydro-indazol-1-yl]-acetic acid ethyl ester (using a method analogous to the one described for 1$^{st}$ step intermediate of example 11-1) (34 mg, 0.072 mmol) in methanol was hydrogenated over 10% Pd/C (6 mg) under 30 psi for 3 hours at room temperature. The reaction mixture was filtered through a glass funnel and concentrated to afford (R)-[4-(3-isopropyl-5-trifluoromethyl-benzenesulfonylamino)-4,5,6,7-tetrahydro-indazol-1-yl]-acetic acid ethyl ester (33 mg, 96.8%) as a white solid. MS cald for $C_{21}H_{26}F_3N_3O_4S$ 473, obsd. (ESI$^+$) [(M+H)$^+$] 474.

Example 12-1a (R)-[4-(3-Isopropyl-5-trifluoromethyl-benzenesulfonylamino)-4,5,6,7-tetrahydro-indazol-1-yl]-acetic acid

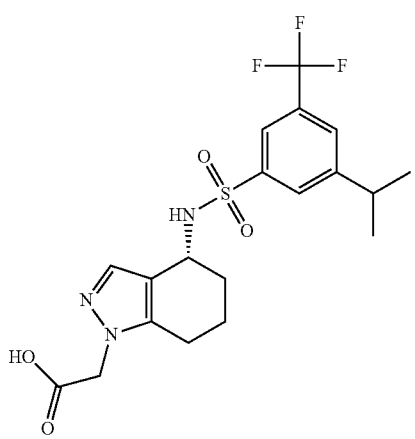

Starting with (R)-[4-(3-isopropyl-5-trifluoromethyl-benzenesulfonylamino)-4,5,6,7-tetrahydro-indazol-1-yl]-acetic acid ethyl ester Prepared by a method analogous to the one described for example 1-1a, (R)-[4-(3-isopropyl-5-trifluoromethyl-benzenesulfonyl-amino)-4,5,6,7-tetrahydro-indazol-1-yl]-acetic acid (28.1 mg, 89.8%) was obtained as a white solid. $^1$H NMR (400 MHz, CD$_3$OD) δ ppm 8.00 (s, 1H), 7.91 (s, 1H), 6.38 (s, 1H), 5.16 (q, 1H), 4.80 (s, 2H), 3.18 (m, 1H), 2.60-2.51 (m, 2H), 2.02-1.65 (m, 4H). MS cald. for $C_{19}H_{22}F_3N_3O_4S$ 445, obsd. (ESI$^+$) [(M+H)$^+$] 446.

Example 13-1

{(R)-4-[(3-Isopropyl-5-trifluoromethyl-benzenesulfonyl)-methyl-amino]-4,5,6,7-tetrahydro-indazol-1-yl}-acetic acid ethyl ester

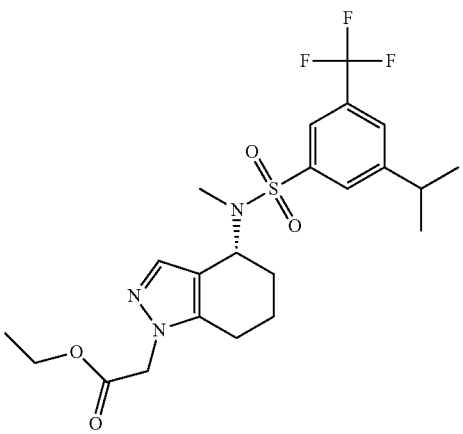

Starting with [(R)-4-(3-isopropyl-5-trifluoromethyl-benzenesulfonylamino)-4,5,6,7-tetrahydro-indazol-1-yl]-acetic acid ethyl ester (Example 12-1) and methyl iodide, using the method analogous to the one described for example 2-1, {(R)-4-[(3-isopropyl-5-trifluoromethyl-benzenesulfonyl)-methyl-amino]-4,5,6,7-tetrahydro-indazol-1-yl}-acetic acid ethyl ester (30 mg, 82.9%) was obtained as an off-white semisolid. MS cald. for $C_{22}H_{28}F_3N_3O_4S$ 487, obsd. (ESI$^+$) [(M+H)$^+$] 488

Example 13-1a

{(R)-4-[(3-Isopropyl-5-trifluoromethyl-benzenesulfonyl)-methyl-amino]-4,5,6,7-tetrahydro-indazol-1-yl}-acetic acid

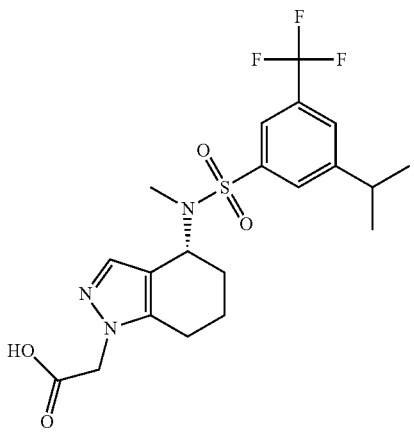

Starting with [(R)-4-(3-isopropyl-5-trifluoromethyl-benzenesulfonylamino)-4,5,6,7-tetrahydro-indazol-1-yl]-acetic acid ethyl ester using the method analogous to the one described for example 1-1a, {(R)-4-[(3-isopropyl-5-trifluoromethyl-benzenesulfonyl)-methyl-amino]-4,5,6,7-tetrahydro-indazol-1-yl}-acetic acid (23.0 mg, 81.6%) was obtained as an off-white semisolid. $^1$H NMR (400 MHz, CD$_3$OD) δ ppm 8.06 (s, 1H), 8.00 (s, 1H), 7.91 (s, 1H), 6.38 (s, 1H), 5.16 (q, 1H), 4.81 (s, 2H), 3.18 (m, 1H), 2.60-2.50 (m, 2H), 2.66 (s, 3H), 2.05-1.63 (m, 4 H), 1.34 (d, 6H). MS calcd. for C$_{19}$H$_{22}$F$_3$N$_3$O$_4$S 459, obsd. (ESI$^+$) [(M+H)$^+$] 460.

Example 14-1

(R)-4-{Methyl-[3-(1-methyl-cyclopropyl)-5-trifluoromethyl-benzenesulfonyl]-amino}-4,5,6,7-tetrahydro-indazol-1-yl)-acetic acid ethyl ester

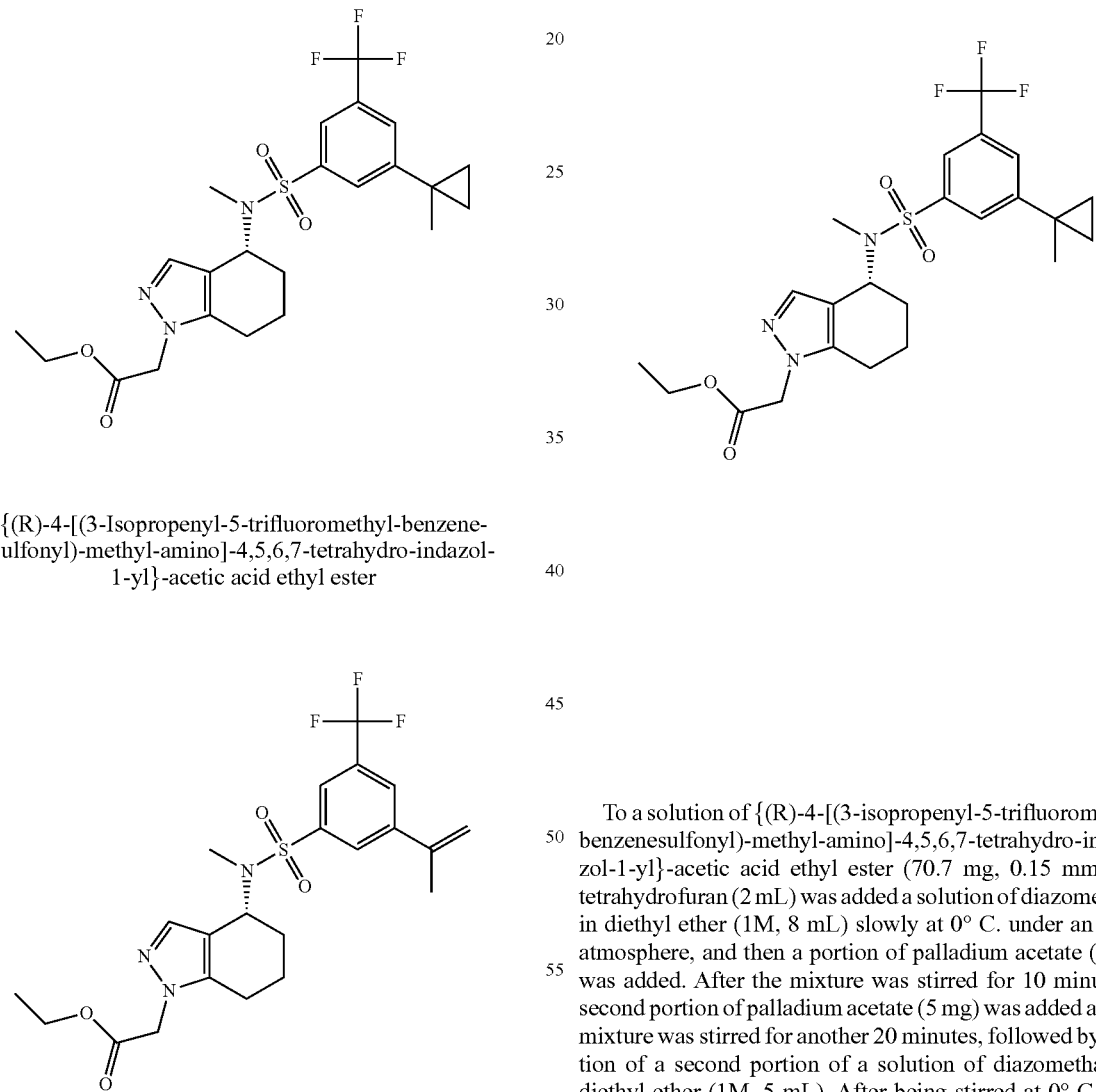

{(R)-4-[(3-Isopropenyl-5-trifluoromethyl-benzenesulfonyl)-methyl-amino]-4,5,6,7-tetrahydro-indazol-1-yl}-acetic acid ethyl ester Starting with [(R)-4-(3-isopropenyl-5-trifluoromethyl-benzene-sulfonyl-amino)-4,5,6,7-tetrahydro-indazol-1-yl]-acetic acid ethyl ester and methyl iodide, using the method analogous to the one described above for example 2-1, {(R)-4-[(3-isopropenyl-5-trifluoromethyl-benzenesulfonyl)-methyl-amino]-4,5,6,7-tetrahydro-indazol-1-yl}-acetic acid ethyl ester (70.7 mg, 89%) was prepared. MS calcd. for C$_{22}$H$_{26}$F$_3$N$_3$O$_4$S 485, obsd. (ESI$^+$) [(M+H)$^+$] 486.

((R)-4-{Methyl-[3-(1-methyl-cyclopropyl)-5-trifluoromethyl-benzenesulfonyl]-amino}-4,5,6,7-tetrahydro-indazol-1-yl)-acetic acid ethyl ester To a solution of {(R)-4-[(3-isopropenyl-5-trifluoromethyl-benzenesulfonyl)-methyl-amino]-4,5,6,7-tetrahydro-indazol-1-yl}-acetic acid ethyl ester (70.7 mg, 0.15 mmol) in tetrahydrofuran (2 mL) was added a solution of diazomethane in diethyl ether (1M, 8 mL) slowly at 0° C. under an argon atmosphere, and then a portion of palladium acetate (5 mg) was added. After the mixture was stirred for 10 minutes, a second portion of palladium acetate (5 mg) was added and the mixture was stirred for another 20 minutes, followed by addition of a second portion of a solution of diazomethane in diethyl ether (1M, 5 mL). After being stirred at 0° C. for 2 hours under an argon atmosphere, the reaction mixture was then quenched by the addition of a few drops of acetic acid, and then filtered through a glass funnel and concentrated in vacuo. The residue was purified by flash column (gradient elution, 0-10% methanol in dichloromethane) to afford ((R)-4-{methyl-[3-(1-methyl-cyclopropyl)-5-trifluoromethyl-benzenesulfonyl]-amino}-4,5,6,7-tetrahydro-indazol-1-yl)- acetic acid ethyl ester (74.5 mg, 99%) as a colorless semisolid. MS cald. for $C_{23}H_{28}F_3N_3O_4S$ 499, obsd. (ESI⁺) [(M+H)⁺] 500.

Example 14-1a ((R)-4-{Methyl-[3-(1-methyl-cyclopropyl)-5-trifluoromethyl-benzenesulfonyl]-amino}-4,5,6,7-tetrahydro-indazol-1-yl)-acetic acid

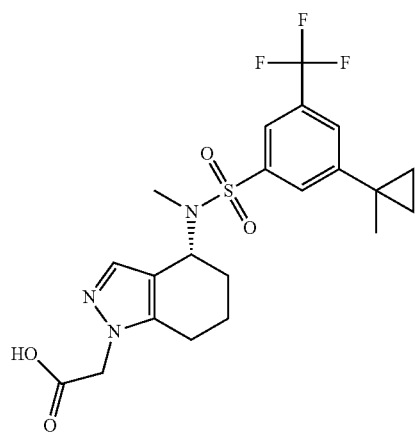

Starting with ((R)-4-{methyl-[3-(1-methyl-cyclopropyl)-5-trifluoromethyl-benzenesulfonyl]-amino}-4,5,6,7-tetrahydro-indazol-1-yl)-acetic acid ethyl ester using the method analogous to the one described for example 1-1a, ((R)-4-{methyl-[3-(1-methyl-cyclopropyl)-5-trifluoromethyl-benzenesulfonyl]-amino}-4,5,6,7-tetrahydro-indazol-1-yl)-acetic acid (35 mg, 61.9%) was obtained as a white solid. ¹H NMR (400 MHz, CD₃OD) δ ppm 8.00 (s, 1H), 7.95 (s, 1H), 7.85 (s, 1H), 6.38 (s, 1H), 5.11 (q, 1H), 4.78 (s, 2H), 2.63 (s, 3H), 2.60-2.45 (m, 2H), 2.03-1.63 (m, 4H), 1.48 (s, 3H), 0.94 (m, 4H). MS cald. for $C_{21}H_{24}F_3N_3O_4S$ 471, obsd. (ESI⁺) [(M+H)⁺] 472.

Example 15-1

((R)-4-{[3-(1-Ethyl-cyclopropyl)-5-trifluoromethyl-benzenesulfonyl]-methyl-amino}-4,5,6,7-tetrahydro-indazol-1-yl)-acetic acid ethyl ester

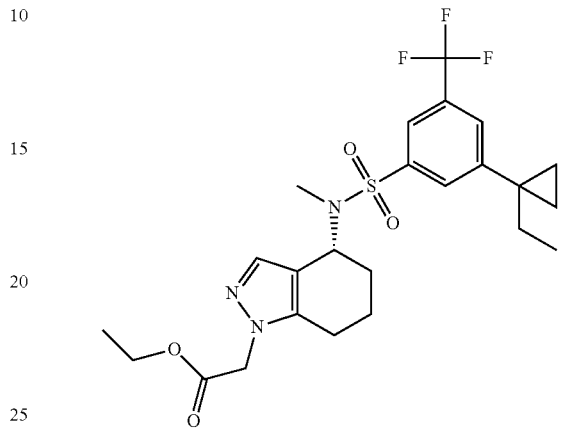

((R)-4-{Methyl-[3-(1-methylene-propyl)-5-trifluoromethyl-benzenesulfonyl]-amino}-4,5,6,7-tetrahydro-indazol-1-yl)-acetic acid ethyl ester

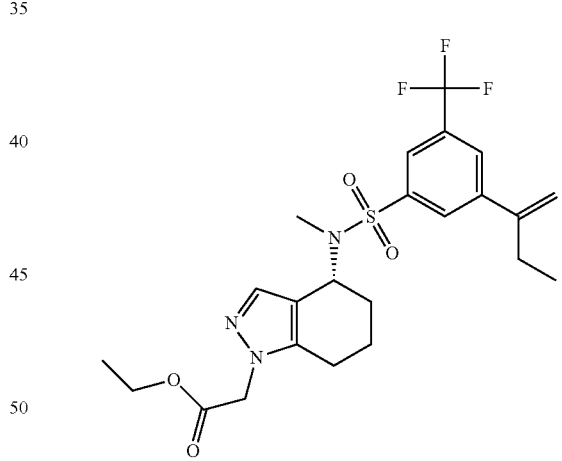

To a solution of {(R)-4-[(3-bromo-5-trifluoromethyl-benzenesulfonyl)-methyl-amino]-4,5,6,7-tetrahydro-indazol-1-yl}-acetic acid ethyl ester (example 2-5) (prepared by the method analogous to the one described for example 2-1) (130 mg, 0.25 mmol) and bis-(1-methylene-propyl)-zinc (174.6 mg, 1.0 mmol) in tetrahydrofuran (5 mL), bis(dibenzylideneacetone)palladium (7.2 mg, 0.013 mmol) and tris(tert-butyl) phosphine (80 μL, 0.025 mmol) were added under an argon atmosphere. After being stirred at 50° C. for 18 hours, the mixture was cooled to room temperature, and then poured into saturated ammonium chloride and extracted with ethyl acetate (20 mL×3). The organic layers were combined, washed with saturated brine, dried over sodium sulfate and concentrated in vacuo. The residue was purified by flash column (gradient elution: 0-20% methanol in dichloromethane) to afford ((R)-4-{methyl-[3-(1-methylene-propyl)-5-trifluoromethyl-benzenesulfonyl]-amino}-4,5,6,7-tetrahydro-indazol-1-yl)-acetic acid ethyl ester as a yellow solid (100 mg, 80.1%). MS cald. for $C_{23}H_{28}F_3N_3O_4S$ 499, obsd. (ESI$^+$) [(M+H)$^+$] 500.

((R)-4-{[3-(1-Ethyl-cyclopropyl)-5-trifluoromethyl-benzenesulfonyl]-methyl-amino}-4,5,6,7-tetrahydro-indazol-1-yl)-acetic acid ethyl ester

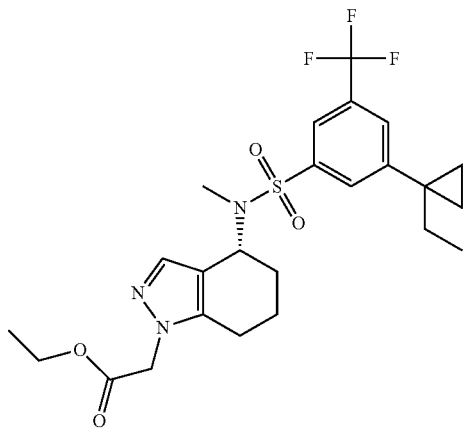

Starting with ((R)-4-{methyl-[3-(1-methylene-propyl)-5-trifluoromethyl-benzenesulfonyl]-amino}-4,5,6,7-tetra-hydro-indazol-1-yl)-acetic acid ethyl ester and a solution of diazomethane in diethyl ether using the method analogous to the one described above for 2$^{nd}$ step of example 14-1, ((R)-4-{[3-(1-ethyl-cyclopropyl)-5-trifluoromethyl-benzenesulfonyl]-methyl-amino}-4,5,6,7-tetrahydro-indazol-1-yl)-acetic acid ethyl ester (82 mg, 83%) was obtained as a white solid. MS cald. for $C_{24}H_{30}F_3N_3O_4S$ 513, obsd. (ESI$^+$) [(M+H)$^+$] 514.

Example 15-1a ((R)-4-{[3-(1-Ethyl-cyclopropyl)-5-trifluoromethyl-benzenesulfonyl]-methyl-amino}-4,5,6,7-tetrahydro-indazol-1-yl)-acetic acid

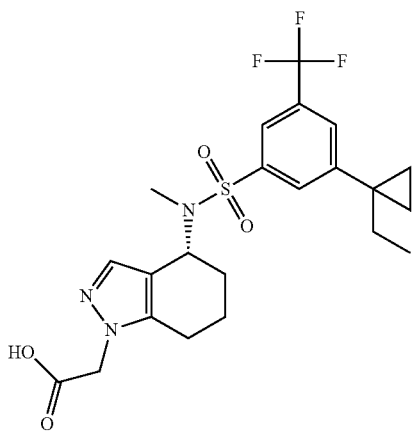

Starting with ((R)-4-{[3-(1-Ethyl-cyclopropyl)-5-trifluoromethyl-benzenesulfonyl]-methyl-amino}-4,5,6,7-tetrahydro-indazol-1-yl)-acetic acid ethyl ester using the method analogous to the one described for example 1-1a, ((R)-4-{[3-(1-ethyl-cyclopropyl)-5-trifluoromethyl-benzenesulfonyl]-methyl-amino}-4,5,6,7-tetrahydro-indazol-1-yl)-acetic acid (41 mg, 70.2%) was obtained as a white solid. $^1$H NMR (400 MHz, CD$_3$OD) δ ppm 8.07 (s, 1H), 8.00 (s, 1H), 7.91 (s, 1H), 6.39 (s, 1H), 5.51 (q, 1H), 4.82 (s, 2H), 2.65 (s, 3H), 2.60-2.51 (m, 2H), 2.05-1.67 (m, 6H), 1.48 (s, 3H), 0.94 (m, 4H), 0.90 (m, 7H). MS cald for $C_{22}H_{26}F_3N_3O_4S$ 485, obsd. (ESI$^+$) [(M+H)$^+$] 486.

Example 16-1

[4-(3-Ethynyl-5-trifluoromethyl-benzenesulfonylamino)-4,5,6,7-tetrahydro-indazol-1-yl]-acetic acid ethyl ester

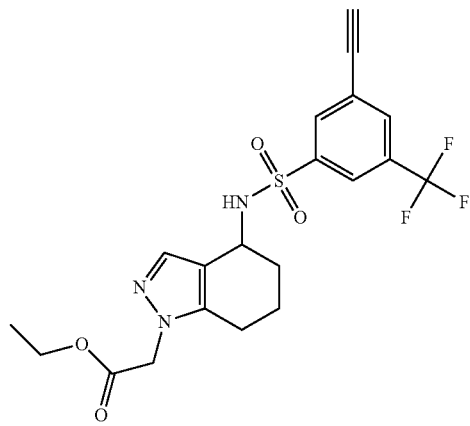

[4-(3-Trifluoromethyl-5-trimethylsilanylethynyl-benzenesulfonylamino)-4,5,6,7-tetrahydro-indazol-1-yl]-acetic acid ethyl ester

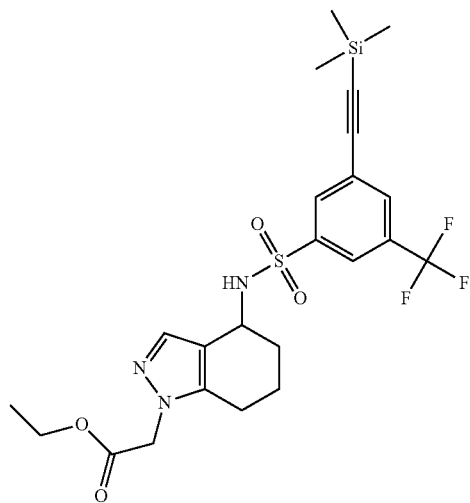

To a mixture of [4-(3-bromo-5-trifluoromethyl-benzenesulfonylamino)-4,5,6,7-tetrahydro-indazol-1-yl]-acetic acid ethyl ester (example 1-7) (51 mg, 0.10 mmol) and ethynyl-trimethyl-silane (20 mg, 0.20 mmol) in triethylamine (0.5 mL) and toluene (0.5 mL), was added copper(I) iodide (0.6 mg, 0.003 mmol) and bis(triphenylphosphine)palladium(II) chloride (2.4 mg, 0.003 mmol). The mixture was heated in a microwave oven at 80° C., for 20 minutes. The resulting mixture was diluted with water and extracted with ethyl acetate. The organic layer was washed with brine, dried over sodium sulfate, concentrated and purified by column chromatography (gradient elution, 0-5% methanol in dichloromethane) to afford [4-(3-trifluoromethyl-5-trimethylsilanylethynyl-benzenesulfonylamino)-4,5,6,7-tetrahydro-indazol-1-yl]-acetic acid ethyl ester (50 mg, 94.8%) as a brown oil. MS calcd. for $C_{23}H_{28}F_3N_3O_4SSi$ 527, obsd (ESI$^+$) [(M+H)$^+$] 528.

[4-(3-Ethynyl-5-trifluoromethyl-benzenesulfonylamino)-4,5,6,7-tetrahydro-indazol-1-yl]-acetic acid ethyl ester

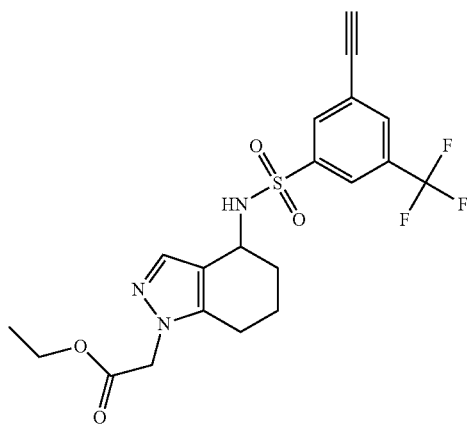

To a solution of [4-(3-trifluoromethyl-5-trimethylsilanylethynyl-benzenesulfonylamino)-4,5,6,7-tetrahydro-indazol-1-yl]-acetic acid ethyl ester (40.0 mg, 0.076 mmol) in N,N-dimethylformamide and water (3 mL, 150:1) was added potassium fluoride (23.0 mg, 0.30 mmol). The mixture was stirred at room temperature for 4 hours. The resulting mixture was poured into ice and extracted with dichloromethane. The organic layer was washed with brine, dried over sodium sulfate, concentrated and purified by column chromatography (gradient elution, 0-5% methanol in dichloromethane) to afford [4-(3-ethynyl-5-trifluoromethyl-benzenesulfonylamino)-4,5,6,7-tetrahydro-indazol-1-yl]-acetic acid ethyl ester (34.0 mg, 98.2%) as a white solid. MS calcd. for $C_{20}H_{20}F_3N_3O_4S$ 455, obsd. (ESI$^+$) [(M+H)$^+$] 456.

Example 16-1a

[4-(3-Ethynyl-5-trifluoromethyl-benzenesulfonylamino)-4,5,6,7-tetrahydro-indazol-1-yl]-acetic acid

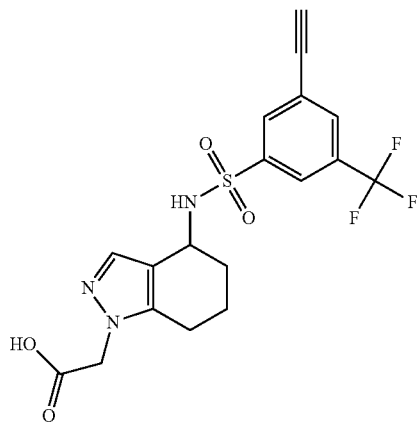

Starting with [4-(3-ethynyl-5-trifluoromethyl-benzenesulfonylamino)-4,5,6,7-tetrahydro-indazol-1-yl]-acetic acid ethyl ester using the method analogous to the one described for example 1-1a, [4-(3-ethynyl-5-trifluoromethyl-benzenesulfonylamino)-4,5,6,7-tetrahydro-indazol-1-yl]-acetic acid (7.6 mg, 23.7%) was obtained as a white solid. $^1$H NMR (400 MHz, CD$_3$OD) δ ppm 8.22 (s, 1H), 8.16 (s, 1H), 8.03 (s, 1H), 7.13 (s, 1H), 4.46 (t, 1H), 3.93 (s, 1H), 2.50 (m, 2H), 2.00-1.62 (m, 4H). MS cald. for $C_{18}H_{16}F_3N_3O_4S$ 427, obsd. (ESI$^+$) [(M+H)$^+$] 428.

Example 17-1

{(R)-4-[Methyl-(3-trifluoromethyl-5-trimethylsilanyl-benzenesulfonyl)-amino]-4,5,6,7-tetrahydro-indazol-1-yl}-acetic acid ethyl ester

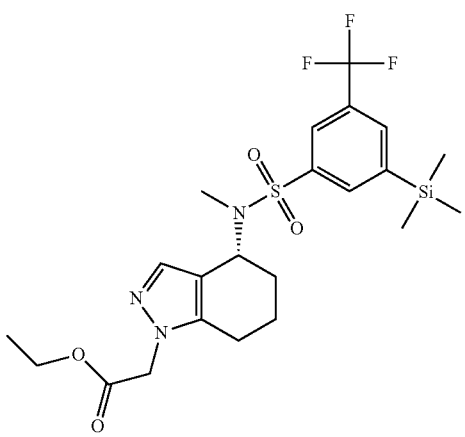

A 10 mL round bottom flask equipped with a reflux condenser and a magnetic stirring bar was charged with tris(dibenzylideneactone)dipalladium (14 mg, 0.01 mmol), {(R)-4-[(3-bromo-5-trifluoromethyl-benzenesulfonyl)-methyl-amino]-4,5,6,7-tetrahydro-indazol-1-yl}-acetic acid ethyl ester (example 2-5) (prepared by the method analogous to the one described for example 2-1) (52.4 mg, 0.10 mmol), 2-(di-tert-butylphosphino)-biphenyl (3.0 mg, 0.01 mmol) and potassium fluoride (58 mg, 0.50 mmol, 50 wt % on Celite) and purged with argon. Degassed 1,3-dimethyl-3,4,5,6-tetrahydro-2(1H)-pyrimidinone (DMPU) (3 mL) was then added by syringe. After the mixture was stirred at room temperature for 5 minutes, 1,1,1,2,2,2-hexamethyldisilane (58.1 mg, 0.41 mmol) was added by syringe. After being stirred at 100° C. for 4 hours, the mixture was poured into saturated sodium chloride and extracted with ethyl acetate. The organic layer was washed with brine, dried over sodium sulfate and concentrated in vacuo. The residue was purified by flash column (gradient elution: 0-5% methanol in dichloromethane) to afford {(R)-4-[methyl-(3-trifluoromethyl-5-trimethylsilanyl-benzenesulfonyl)-amino]-4,5,6,7-tetrahydro-indazol-1-yl}-acetic acid ethyl ester (30 mg, 58%) as a white solid. MS cald. for $C_{22}H_{30}F_3N_3O_4SSi$ 517, obsd. (ESI$^+$) [(M+H)$^+$] 518.

Example 17-1a

{(R)-4-[Methyl-(3-trifluoromethyl-5-trimethylsilanyl-benzenesulfonyl-1)-amino]-4,5,6,7-tetrahydro-indazol-1-yl}-acetic acid

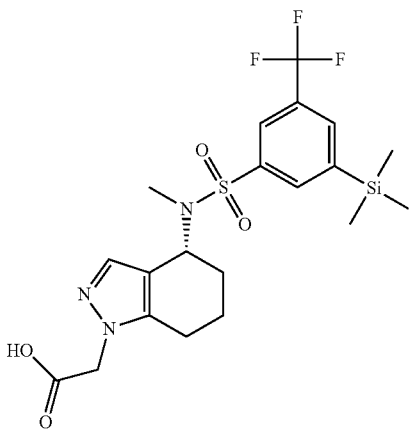

Starting with {(R)-4-[Methyl-(3-trifluoromethyl-5-trimethylsilanyl-benzenesulfonyl)-amino]-4,5,6,7-tetrahydro-indazol-1-yl}-acetic acid ethyl ester using the method analogous to the one described example 1-1a, {(R)-4-[Methyl-(3-trifluoromethyl-5-trimethylsilanyl-benzenesulfonyl)-amino]-4,5,6,7-tetrahydro-indazol-1-yl}-acetic acid (8.2 mg, 56%) as a white solid. $^1$H NMR (400 MHz, CD$_3$OD) δ ppm 8.27 (s, 1H), 8.15 (s, 1H), 8.11 (s, 1H), 6.42 (s, 1 H), 5.16 (q, 1H), 4.83 (s, 2H), 2.65 (s, 3H), 2.53 (m, 2H), 2.05-1.66 (m, 4H), 0.39 (s, 9H). MS cald. for $C_{20}H_{26}F_3N_3O_4SSi$ 489, obsd. (ESI$^+$) [(M+H)$^+$] 490.

Example 18-1

{(R)-4-[(3-Cyclopentyl-5-trifluoromethyl-benzenesulfonyl)-methyl-amino]-4,5,6,7-tetrahydro-indazol-1-yl}-acetic acid ethyl ester

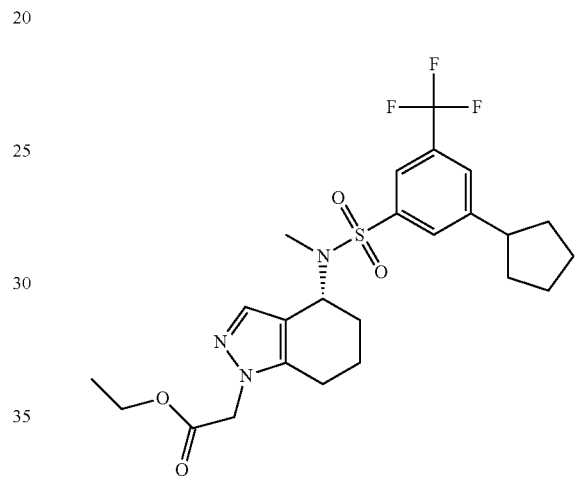

To a mixture of {(R)-4-[(3-bromo-5-trifluoromethyl-benzenesulfonyl)-methyl-amino]-4,5,6,7-tetrahydro-indazol-1-yl}-acetic acid ethyl ester (example 2-5) (prepared by the method analogous to the one described for example 2-1) (290 mg, 0.556 mmol) and a solution of cyclopentylzinc bromide in tetrahydrofuran (0.5 M, 10.0 mL, 5.0 mmol), bis(dibenzylideneacetone)palladium(0) (16.7 mg, 0.028 mmol) and tris(tert-butyl)phosphine (178 µL, 0.056 mmol) were added under an argon atmosphere. After being stirred at 50° C. for 1 hour, the mixture was concentrated in vacuo. Saturated ammonium chloride was added and the mixture was extracted with ethyl acetate (20 mL×3). The organic layers were combined, washed with saturated ammonium chloride, dried over sodium sulfate and concentrated in vacuo to afford {(R)-4-[(3-cyclopentyl-5-trifluoromethyl-benzene-sulfonyl)-methyl-amino]-4,5,6,7-tetrahydro-indazol-1-yl}-acetic acid ethyl ester (220 mg, 77%) as a viscous oil which was used for the next step without any purification. MS cald. for $C_{24}H_{30}F_3N_3O_4S$ 513, obsd. (ESI$^+$) [(M+H)$^+$] 514.

Example 18-1a

{(R)-4-[(3-Cyclopentyl-5-trifluoromethyl-benzene-sulfonyl)-methyl-amino]-4,5,6,7-tetrahydro-indazol-1-yl}-acetic acid

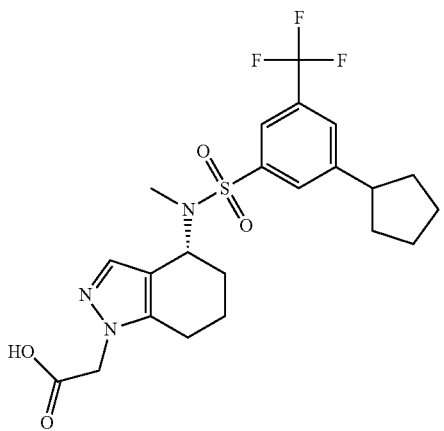

Starting with {(R)-4-[(3-cyclopentyl-5-trifluoromethyl-benzenesulfonyl)-methyl-amino]-4,5,6,7-tetrahydro-indazol-1-yl}-acetic acid ethyl ester using the method analogous to the one described for example 1-1a, {(R)-4-[(3-cyclopentyl-5-trifluoromethyl-benzenesulfonyl)-methyl-amino]-4,5,6,7-tetrahydro-indazol-1-yl}-acetic acid (68.2 mg, 25.3%) was obtained as a white solid. $^1$H NMR (400 MHz, CD$_3$OD) δ ppm 8.05 (s, 1H), 7.98 (s, 1H), 7.90 (s, 1H), 6.40 (s, 1H), 5.15 (t, 1S), 4.79 (t, 1H), 2.60 (s, 1H), 2.50 (m, 2H), 2.20-1.60 (m, 13H). MS cald. for $C_{22}H_{26}F_3N_3O_4S$ 485, obsd. (ESI$^+$) [(M+H)$^+$] 486.

Example 19-1

{(R)-4-[(3-Acetyl-5-trifluoromethyl-benzenesulfonyl)-methyl-amino]-4,5,6,7-tetrahydro-indazol-1-yl}-acetic acid ethyl ester

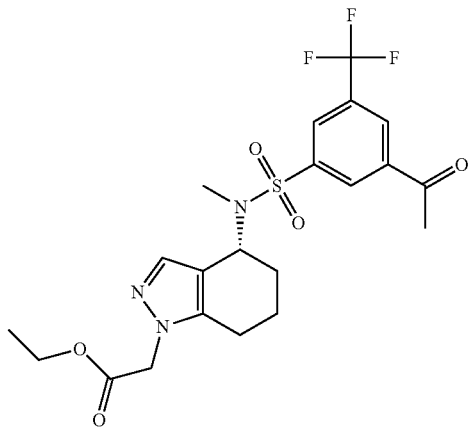

To a solution of {(R)-4-[(3-bromo-5-trifluoromethyl-benzenesulfonyl)-methyl-amino]-4,5,6,7-tetrahydro-indazol-1-yl}-acetic acid ethyl ester (example 2-5) (prepared by the method analogous to the one described for example 2-1) (1.0 g, 1.9 mmol) in N,N-dimethylformamide (8 mL) was added tris(dibenzylideneacetone)dipalladium(0) (Pd$_2$(dba)$_3$) (175 mg, 0.19 mmol), triphenylarsine (Ph$_3$As) (175 mg, 5.72 mmol) and 1-ethoxy-vinyltributyltin (1 mL, 2.86 mmol). After being stirred at 80° C. for 2 hours under an argon atmosphere, the reaction mixture was cooled to room temperature, 4N hydrochloric acid (1 mL) was added, and the mixture was stirred at room temperature for 20 minutes. The resulting mixture was poured into water (40 mL) and extracted with ethyl acetate (3×20 mL). The combined organic layers were washed with water (20 mL) and brine (20 mL), and then concentrated in vacuo. The residue was purified by flash column (gradient elution: 15-30% ethyl acetate in petroleum ether) to afford {(R)-4-[(3-acetyl-5-trifluoromethyl-benzenesulfonyl)-methyl-amino]-4,5,6,7-tetrahydro-indazol-1-yl}-acetic acid ethyl ester as a yellow oil (800 mg, 86.4%). MS cald. for $C_{21}H_{24}F_3N_3O_5S$ 487, obsd. (ESI$^+$) [(M+H)$^+$] 488.

Example 19-1a

{(R)-4-[(3-Acetyl-5-trifluoromethyl-benzenesulfonyl)-methyl-amino]-4,5,6,7-tetrahydro-indazol-1-yl}-acetic acid Starting with {(R)-4-[(3-acetyl-5-trifluoromethyl-benzenesulfonyl)-methyl-amino]-4,5,6,7-tetrahydro-indazol-1-yl}-acetic acid ethyl ester using the method analogous to the one described for example 1-1a, {(R)-4-[(3-acetyl-5-trifluoromethyl-benzene-sulfonyl)-methyl-amino]-4,5,6,7-tetrahydro-indazol-1-yl}-acetic acid (17 mg, 76%) was prepared as a colorless viscous oil. $^1$H NMR (400 MHz, CD$_3$OD) δ ppm8.66 (s, 1H), 8.55 (s, 1H), 8.41 (s, 1H), 6.68 (s, 1H), 5.20

(q, 1H), 4.84 (s, 2H), 2.74 (s, 3H), 2.69 (s, 3H), 2.55 (m, 2H), 2.05-1.62 (m, 4H). MS cald. for $C_{19}H_{20}F_3N_3O_5S$ 459, obsd. (ESI$^+$) [(M+H)$^+$] 460.

Example 20-1

((R)-4-{[3-(1,1-Difluoro-ethyl)-5-trifluoromethyl-benzenesulfonyl]-methyl-amino}-4,5,6,7-tetrahydro-indazol-1-yl)-acetic acid ethyl ester

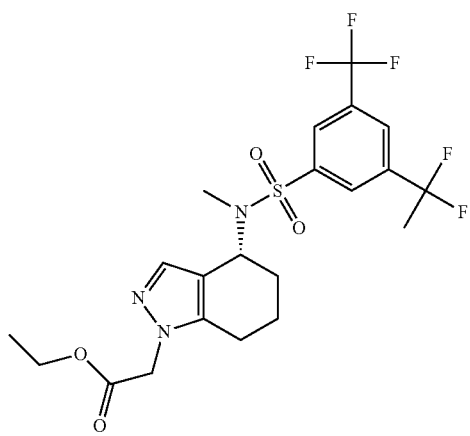

Example 20-1a ((R)-4-{[3-(1,1-Difluoro-ethyl)-5-trifluoromethyl-benzenesulfonyl]-methyl-amino}-4,5,6,7-tetrahydro-indazol-1-yl)-acetic acid

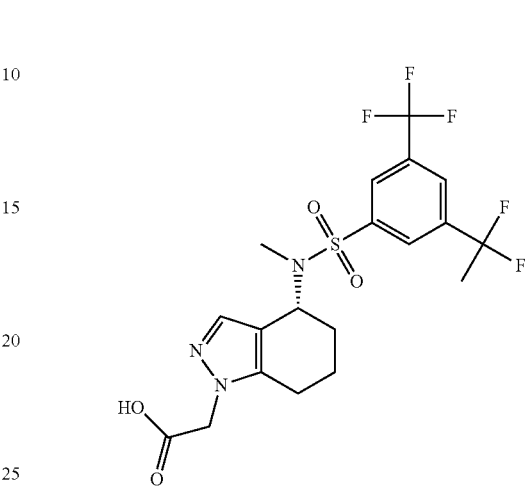

Starting with ((R)-4-{[3-(1,1-difluoro-ethyl)-5-trifluoromethyl-benzenesulfonyl]-methyl-amino}-4,5,6,7-tetrahydro-indazol-1-yl)-acetic acid ethyl ester using a method analogous to the one described for example 1-1a, ((R)-4-{[3-(1,1-difluoro-ethyl)-5-trifluoro-methyl-benzenesulfonyl]-methyl-amino}-4,5,6,7-tetrahydro-indazol-1-yl)-acetic acid (80 mg, 42.6%) was obtained as a white solid. $^1$H NMR (400 MHz, CD$_3$OD) δ ppm 8.32 (d, 2H), 8.19 (s, 1H), 6.58 (s, 1H), 5.20 (q, 1H), 4.80 (s, 2H), 2.68 (s, 3H), 2.55 (m, 2H), 2.09 (m, 4H), 1.85-1.66 (m, 3H). MS cald. for $C_{19}H_{20}F_5N_3O_4S$ 481, obsd. (ESI$^+$) [(M+H)$^+$] 482.

Example 21-1

2-{(R)-4-[(3,5-Bis-trifluoromethyl-benzenesulfonyl)-methyl-amino]-4,5,6,7-tetrahydro-indazol-1-yl}-2-methyl-propionic acid methyl ester

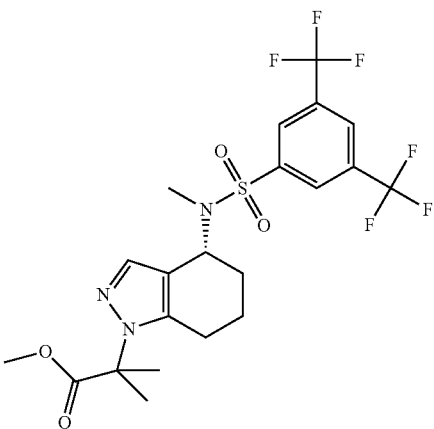

To a solution of {(R)-4-[(3-acetyl-5-trifluoromethyl-benzenesulfonyl)-methyl-amino]-4,5,6,7-tetrahydro-indazol-1-yl}-acetic acid ethyl ester (example 19-1) (300 mg, 0.616 mmol) in anhydrous dichloromethane (3 mL) in a bomb bottle (5 mL) was added bis(2-methoxy-ethyl)aminosulfur trifluoride (400 μL, 2.17 mmol) under an argon atmosphere. After being stirred at 70° C. for 4 hours, the mixture was cooled to room temperature, poured into saturated sodium bicarbonate and extracted with dichloromethane (20 mL×3). The combined organic layers were washed with water (20 mL) and brine (20 mL) and then concentrated in vacuo. The residue was purified by flash column (gradient elution: 15-30% ethyl acetate in petroleum ether) to afford ((R)-4-{[3-(1,1-difluoro-ethyl)-5-trifluoromethyl-benzenesulfonyl]-methyl-amino}-4,5,6,7-tetrahydro-indazol-1-yl)-acetic acid ethyl ester (250 mg, 79.7%) as a yellow oil. MS cald for $C_{21}H_{24}F_5N_3O_4S$ 509, obsd. (ESI$^+$) [(M+H)$^+$] 510.

To a solution of {(R)-4-[(3,5-bis-trifluoromethyl-benzene-sulfonyl)-methyl-amino]-4,5,6,7-tetrahydro-indazol-1-yl}-acetic acid (50 mg, 0.10 mmol) in N,N-dimethylformamide (2 ml), sodium hydride (17 mg, 0.48 mmol) was added. The mixture was stirred at room temperature for 30 minutes. To the reaction mixture was added methyl iodide (80 mg, 0.56 mmol) and the mixture was stirred at room temperature for 3 hours. After filtration, the filtrate was purified by preparative HPLC to afford 2-{(R)-4-[(3,5-bis-trifluoromethyl-benzene-sulfonyl)-methyl-amino]-4,5,6,7-tetrahydro-indazol-1-yl}-2-methyl-propionic acid methyl ester (50 mg, 89%) as a white solid. MS calcd. for $C_{21}H_{23}F_6N_3O_4S$ 527, obsd. (ESI$^+$) [(M+H)$^+$] 528.

Example 21-1a

2-{(R)-4-[(3,5-Bis-trifluoromethyl-benzenesulfo-nyl)-methyl-amino]-4,5,6,7-tetrahydro-indazol-1-yl}-2-methyl-propionic acid

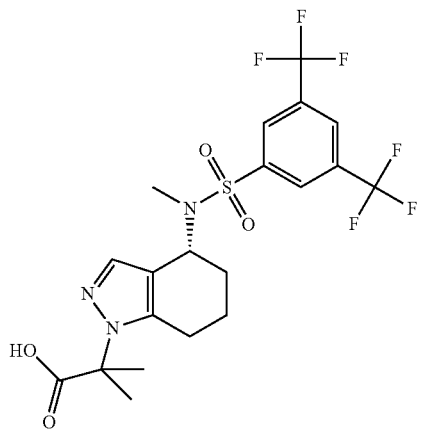

Starting with 2-{(R)-4-[(3,5-bis-trifluoromethyl-benzene-sulfonyl)-methyl-amino]-4,5,6,7-tetrahydro-indazol-1-yl}-2-methyl-propionic acid methyl ester using the method analogous to the one described for example 1-1a, 2-{(R)-4-[(3,5-bis-trifluoromethyl-benzene-sulfonyl)-methyl-amino]-4,5,6,7-tetrahydro-indazol-1-yl}-2-methyl-propionic acid (15 mg, 77%) was obtained as a white solid. $^1$H NMR (400 MHz, CD$_3$OD) δ ppm 8.48 (s, 2H), 8.35 (s, 1H), 6.60 (s, 1H), 5.21 (s, 1H), 2.65 (s, 3H), 2.50 (m, 2H), 1.85 (m, 4H), 1.75 (d, 6H). MS cald. for $C_{20}H_{21}F_6N_3O_4S$ 513, obsd. (ESI$^+$) [(M+H)$^+$] 514.

Example 22-1

[4-(3-Acetylamino-benzenesulfonylamino)-4,5,6,7-tetrahydro-indazol-1-yl]-acetic acid ethyl ester

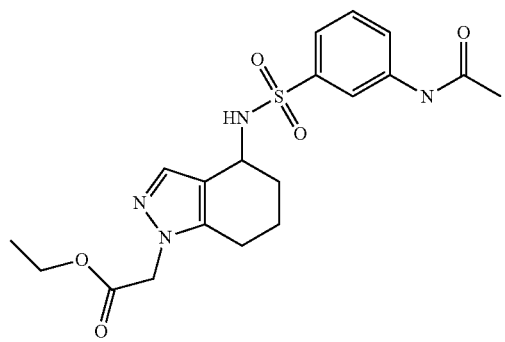

[4-(3-Nitro-benzenesulfonylamino)-4,5,6,7-tetrahydro-indazol-1-yl]-acetic acid ethyl ester

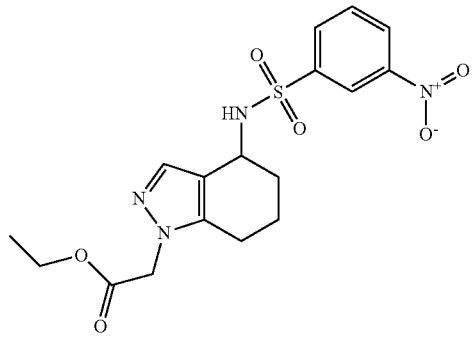

Starting with (4-amino-4,5,6,7-tetrahydro-indazol-1-yl)-acetic acid ethyl ester and 3-nitro-benzenesulfonyl chloride using the method analogous to the one described above for example 1-1, [4-(3-nitro-benzenesulfonylamino)-4,5,6,7-tetrahydro-indazol-1-yl]-acetic acid ethyl ester (519 mg, 63.6%) was obtained as a white solid. MS cald. for $C_{17}H_{20}N_4O_6S$ 408, obsd. (ESI$^+$) [(M+H)$^+$] 409.

[4-(3-Amino-benzenesulfonylamino)-4,5,6,7-tetrahydro-indazol-1-yl]-acetic acid ethyl ester

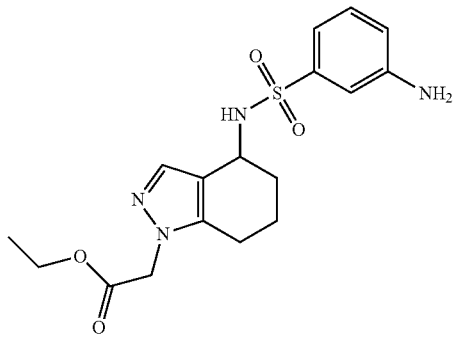

To a solution of [4-(3-nitro-benzenesulfonylamino)-4,5,6,7-tetrahydro-indazol-1-yl]-acetic acid ethyl ester (390 mg, 0.96 mmol) in acetic acid (3 mL) and ethanol (15 mL) was added zinc powder portionwise. After being heated at reflux for 2 hours, the mixture was cooled to room temperature, diluted with dichloromethane (30 mL), filtered through a glass funnel and concentrated in vacuo. The residue was purified by flash column (gradient elution, 0-5% methanol in dichloromethane) to afford [4-(3-amino-benzenesulfonylamino)-4,5,6,7-tetrahydro-indazol-1-yl]-acetic acid ethyl ester (300 mg, 83%) as a semisolid. MS cald. for $C_{17}H_{22}N_4O_4S$ 378, obsd. (ESI$^+$) [(M+H)$^+$] 379.

[4-(3-Acetylamino-benzenesulfonylamino)-4,5,6,7-tetrahydro-indazol-1-yl]-acetic acid ethyl ester

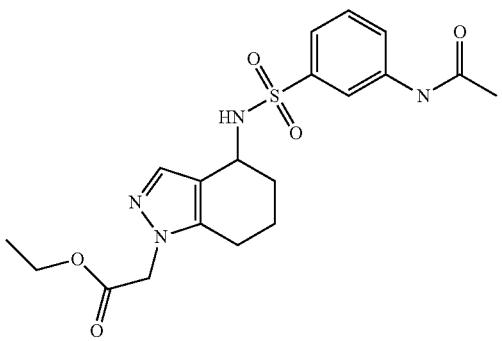

To a solution of [4-(3-amino-benzenesulfonylamino)-4,5,6,7-tetrahydro-indazol-1-yl]-acetic acid ethyl ester (30 mg, 0.079 mmol) and acetyl chloride (9.2 mg, 0.119 mmol) in tetrahydrofuran (3 mL) was added triethylamine (16 mg, 0.158 mmol) at 0° C. After being stirred at room temperature overnight, the mixture was concentrated in vacuo. The residue was purified by flash column (gradient elution, 0-5% methanol in dichloromethane) to afford [4-(3-acetylamino-benzenesulfonylamino)-4,5,6,7-tetrahydro-indazol-1-yl]-acetic acid ethyl ester (24 mg, 72%) as a white solid. MS cald. for $C_{19}H_{24}N_4O_5S$ 420, obsd. (ESI$^+$) [(M+H)$^+$] 421.

Example 22-1a

[4-(3-Acetylamino-benzenesulfonylamino)-4,5,6,7-tetrahydro-indazol-1-yl]-acetic acid

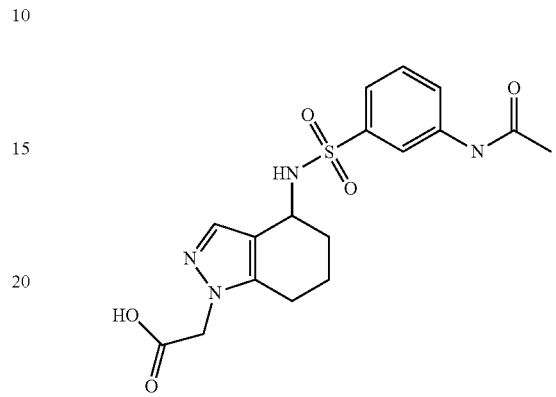

Starting with [4-(3-acetylamino-benzenesulfonylamino)-4,5,6,7-tetrahydro-indazol-1-yl]-acetic acid ethyl ester using the method analogous to the one described for example 1-1a, [4-(3-acetylamino-benzenesulfonylamino)-6,7-dihydro-indazol-1-yl]-acetic acid (11.0 mg, 50%) was obtained as a white solid. $^1$H NMR (400 MHz, CD$_3$OD) δ ppm 8.30 (s, 1H), 7.80 (d, 1H), 7.67 (d, 1H), 7.57 (d, 1H), 6.72 (s, 1H), 4.77 (s, 2H), 4.38 (s, 1H), 3.76 (s, 3H), 2.60-2.45 (m, 2H), 1.90-1.75 (m, 4H). MS cald. for $C_{17}H_{20}N_4O_5S$ 392, obsd. (ESI$^+$) [(M+H)$^+$] 393.

Example 23-1

[4-(3-Methanesulfonylamino-benzenesulfonylamino)-4,5,6,7-tetrahydro-indazol-1-yl]-acetic acid ethyl ester

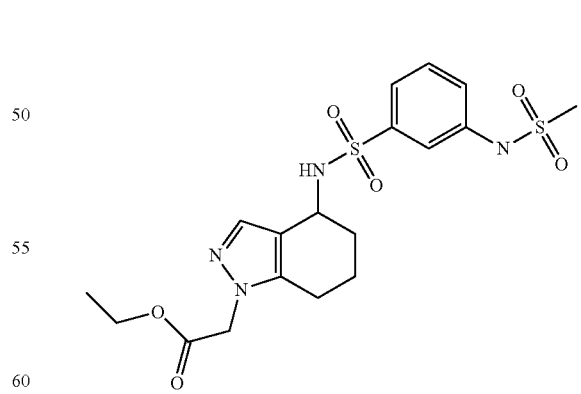

Starting with [4-(3-amino-benzenesulfonylamino)-4,5,6,7-tetrahydro-indazol-1-yl]-acetic acid ethyl ester and methanesulfonyl chloride, and using the method analogous to the one described for example 22-1, [4-(3-methanesulfonylamino-benzene-sulfonyl-amino)-4,5,6,7-tetrahydro-indazol-1-yl]-acetic acid ethyl ester (15 mg, 70%) was obtained as a white solid. MS calcd. for $C_{18}H_{24}N_4O_6S_2$ 456, obsd. (ESI$^+$) [(M+H)$^+$]:457.

Example 23-1a

[4-(3-Methanesulfonylamino-benzenesulfonylamino)-4,5,6,7-tetrahydro-indazol-1-yl]-acetic acid

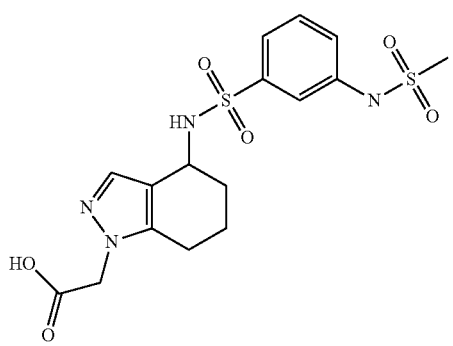

Starting from [4-(3-methanesulfonylamino-benzenesulfonylamino)-4,5,6,7-tetrahydro-indazol-1-yl]-acetic acid ethyl ester, and using the method analogous to the one described for example 1-1a, [4-(3-methanesulfonylamino-benzenesulfonylamino)-4,5,6,7-tetrahydro-indazol-1-yl]-acetic acid (10 mg, 50%) was obtained as a white solid. $^1$H NMR (400 MHz, CD$_3$OD) δ ppm 7.82 (t, 1H), 7.75 (d, 2H), 6.02 (s, 1H), 5.08-4.99 (m, 1H), 4.79 (s, 2H), 2.60 (s, 3H), 2.57-2.44 (m, 2H), 2.08-1.95 (m, 1H), 1.91-1.73 (m, 2H), 1.71-1.62 (m, 1H), 1.40-1.37 (m, 18H). MS cald. for $C_{16}H_{20}N_4O_6S_2$ 428, obsd. (ESI$^+$) [(M+H)$^+$] 429.

Example 24-1a

{(R)-4-[Methyl-(3-pyrrolidin-1-yl-5-trifluoromethyl-benzenesulfonyl)-amino]-4,5,6,7-tetrahydro-indazol-1-yl}-acetic acid

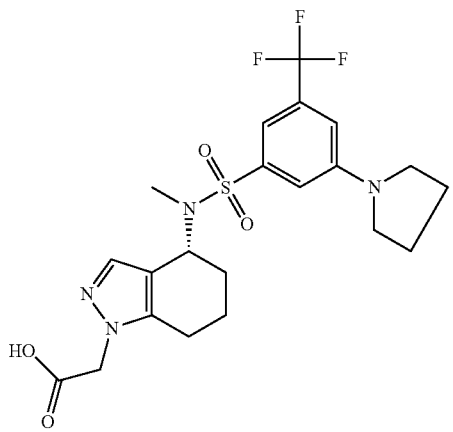

{(R)-4-[(3-Fluoro-5-trifluoromethyl-benzenesulfonyl)-methyl-amino]-4,5,6,7-tetrahydro-indazol-1-yl}-acetic acid (25 mg, 0.066 mmol) and pyrrolidine (47 mg, 0.66 mmol) were dissolved in dimethyl sulfoxide (1.5 mL). The mixture was heated in a microwave oven at 180° C. for 50 minutes. The resulting mixture was acidified with acetic acid to pH 4, and then filtered and purified by preparative HPLC to afford {(R)-4-[methyl-(3-pyrrolidin-1-yl-5-trifluoromethyl-benzenesulfonyl)-amino]-4,5,6,7-tetrahydro-indazol-1-yl}-acetic acid (15 mg, 48.5%) as a white powder. $^1$H NMR (400 MHz, CD$_3$OD) δ ppm 7.24 (s, 1H), 7.14 (s, 1H), 6.98 (s, 1H), 6.41 (s, 1 H), 5.05 (t, 1H), 4.75 (s, 2H), 3.35 (t, 4H), 2.61 (s, 3H), 2.45 (m, 2H), 2.08-1.61 (m, 8H). MS calcd. for $C_{21}H_{25}F_3N_4O_4S$ 486, obsd. (ESI$^+$) [(M+H)$^+$] 487.

Examples 24-2a to 24-4a

The following examples 24-2a to 24-4a were prepared in an analogous manner as described for example 24-1 using {(R)-4-[(3-fluoro-5-trifluoromethyl-benzenesulfonyl)-methyl-amino]-4,5,6,7-tetrahydro-indazol-1-yl}-acetic acid and the appropriate commercially available amines

| Example No. | Systematic Name | $^1$H NMR (400 MHz, CD$_3$OD) δ ppm | MS (ESI+, M + H) | Structure |
|---|---|---|---|---|
| 24-2a | ((R)-4-{[3-(Isopropyl-methyl-amino)-5-trifluoromethyl-benzenesulfonyl]-methyl-amino}-4,5,6,7-tetrahydro-indazol-1-yl)-acetic acid | 7.38 (s, 1 H), 7.27 (s, 1 H), 7.21 (s, 1 H), 6.38 (s, 1 H), 5.05 (t, 1 H), 4.74 (s, 2 H), 4.21 (m, 1 H), 2.83 (s, 3 H), 261 (s, 3 H), 2.51 (s, 2 H), 1.99 (s, 1 H), 1.85-1.60 (m, 3 H), 1.20 (m, 6 H) | 489 | 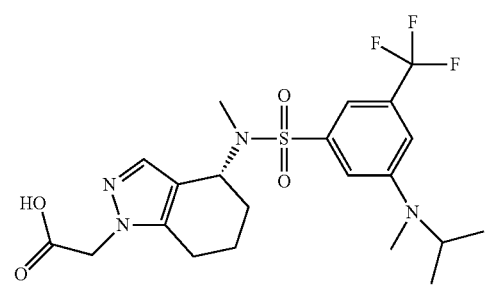 |

| Example No. | Systematic Name | ¹H NMR (400 MHz, CD$_3$OD) δ ppm | MS (ESI+, M + H) | Structure |
|---|---|---|---|---|
| 24-3a | {(R)-4-[(3-Dimethylamino-5-trifluoromethyl-benzenesulfonyl)-methyl-amino]-4,5,6,7-tetrahydro-indazol-1-yl}-acetic acid | 7.32 (s, 2 H), 7.16 (s, 1 H), 6.43 (s, 1 H), 5.08 (t, 1 H), 4.76 (s, 2 H), 3.08 (s, 6 H), 2.63 (s, 3 H), 2.57 (t, 2 H), 2.03-1.63 (m, 4 H) | 461 | 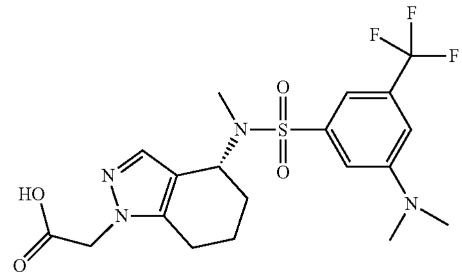 |
| 24-4a | {(R)-4-[(3-Diethylamino-5-trifluoromethyl-benzenesulfonyl)-methyl-amino]-4,5,6,7-tetrahydro-indazol-1-yl}-acetic acid | 7.25 (s, 1 H), 7.21 (s, 1 H), 7.07 (s, 1 H), 6.37 (s, 1 H), 5.03 (t, 1 H), 4.70 (s, 2 H), 3.45 (m, 4 H), 2.60 (s, 3 H), 2.51 (s, 2 H), 1.98-1.61 (m, 4 H), 1.15 (t, 6 H) | 489 | 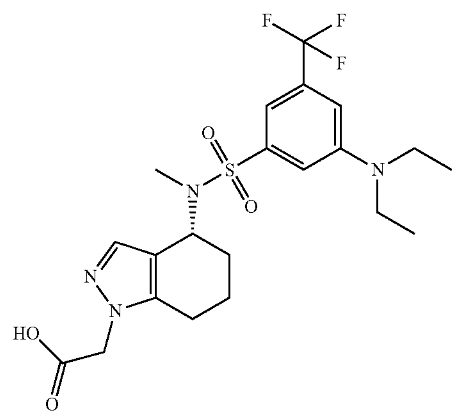 |

Example 25-1a

[4-(3-Cyclopropyl-5-trifluoromethyl-benzenesulfonylamino)-4,5,6,7-tetrahydro-indazol-1-yl]-acetic acid

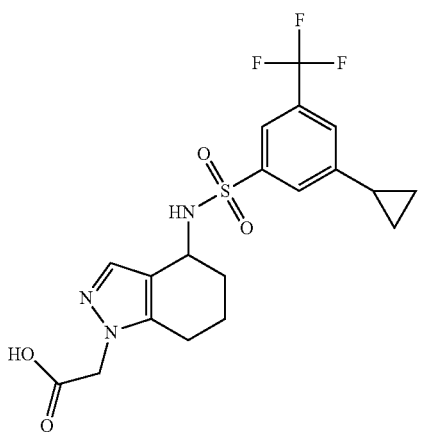

[4-(3-Bromo-5-trifluoromethyl-benzenesulfonylamino)-4,5,6,7-tetrahydro-indazol-1-yl]-acetic acid ethyl ester (51.0 mg, 0.10 mmol, example 1-8), cyclopropylboronic acid (10.4 mg, 0.12 mmol), palladium (II) acetate (1.2 mg, 0.005 mmol), tricyclohexylphosphine (2.8 mg, 0.010 mmol) and potassium phosphate (76.4 mg, 0.36 mmol) were dissolved in toluene (0.5 mL) and water (0.1 mL). The mixture was heated in a microwave oven at 180° C. for 30 minutes under an argon atmosphere. The resulting mixture was quenched with saturated ammonium chloride solution, and then extracted with ethyl acetate. The organic layer was washed with brine, dried over sodium sulfate and concentrated in vacuo. The residue was purified by preparative HPLC to afford [4-(3-cyclopropyl-5-trifluoromethyl-benzenesulfonylamino)-4,5,6,7-tetrahydro-indazol-1-yl]-acetic acid (4.2 mg, 18.9%) as a white powder. ¹H NMR (400 MHz, CD$_3$OD) δ ppm 7.97 (s, 1H), 7.85 (s, 1H), 7.70 (s, 1H), 6.65 (s, 1H), 4.80 (s, 2H), 4.41 (t, 1H), 2.50 (m, 2H), 2.20 (m, 1H), 2.00-1.73 (m, 4H), 1.15 (, 2H), 0.85 (m, 2H). MS cald. for C$_{19}$H$_{20}$F$_3$N$_3$O$_4$S 443, obsd. (ESI$^+$) [(M+H)$^+$] 444.

Examples 25-2a to 25-3a

The following examples 25-2a to 25-3a were prepared in an analogous manner as described for example 25-1a starting with [4-(3-bromo-5-trifluoromethyl-benzene-sulfonylamino)-4,5,6,7-tetrahydro-indazol-1-yl]-acetic acid ethyl ester (example 1-8) and the appropriate commercially available alkylboronic acids.

| Example No. | Systematic Name | ¹H NMR (400 MHz, CD₃OD) δ ppm | MS (ESI+, M + H) | Structure |
|---|---|---|---|---|
| 25-2a | [4-(3-Methyl-5-trifluoromethyl-benzenesulfonylamino)-4,5,6,7-tetrahydro-indazol-1-yl]-acetic acid | 8.03 (d, 2 H), 7.82 (s, 1 H), 6.70 (s, 1 H), 4.80 (s, 2 H), 4.41 (t, 1 H), 2.50 (m, 5 H), 2.20 (m, 1 H), 1.94-1.72 (m, 4 H). | 418 | 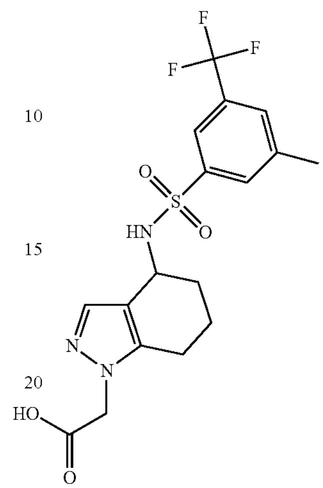 |
| 25-3a | [4-(3-Isopropenyl-5-trifluoromethyl-benzenesulfonylamino)-4,5,6,7-tetrahydro-indazol-1-yl]-acetic acid | 8.28 (s, 1 H), 8.12 (s, 1 H), 8.05 (s, 1 H), 6.70 (s, 1 H), 5.64 (s, 1 H), 5.38 (s, 1 H), 4.83-4.76 (m, 2 H), 4.43 (t, 1 H), 2.54 (d, J = 23.24 Hz, 2 H), 2.26 (s, 3 H), 1.98-1.89 (m, 1 H), 1.80 (m, 3 H) | 472 | 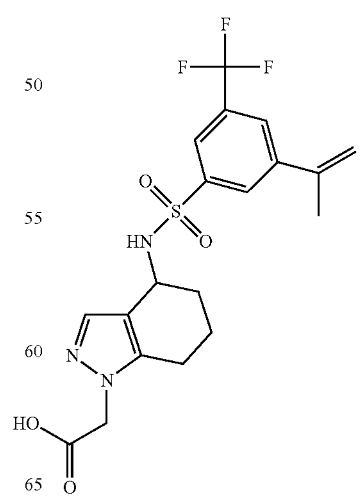 |

Example 26-1

{(R)-4-[(3-Cyclopropyl-5-trifluoromethyl-benzene-sulfonyl)-methyl-amino]-4,5,6,7-tetrahydro-indazol-1-yl}-acetic acid methyl ester

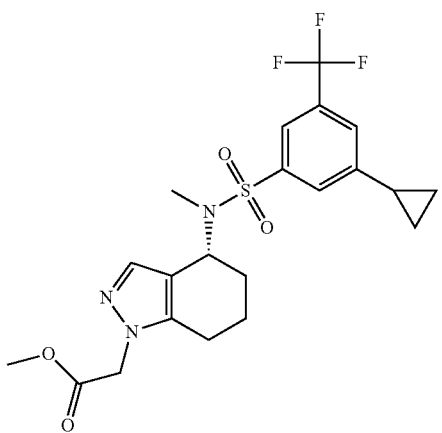

Starting with [(R)-4-(3-cyclopropyl-5-trifluoro-methyl-benzenesulfonylamino)-4,5,6,7-tetrahydro-indazol-1-yl]-acetic acid (prepared by a method analogous to the one described above for example 25-1a) and methyl iodide using a method analogous to the procedure described for example 2-1, {(R)-4-[(3-cyclopropyl-5-trifluoromethyl-benzene-sulfonyl)-methyl-amino]-4,5,6,7-tetrahydro-indazol-1-yl}-acetic acid methyl ester (45 mg, 86%) was obtained as a yellow solid. MS cald. for $C_{21}H_{24}F_3N_3O_4S$ 471, obsd. (ESI$^+$) [(M+H)$^+$] 472.

Example 26-1a

{(R)-4-[(3-Cyclopropyl-5-trifluoromethyl-benzene-sulfonyl)-methyl-amino]-4,5,6,7-tetrahydro-indazol-1-yl}-acetic acid

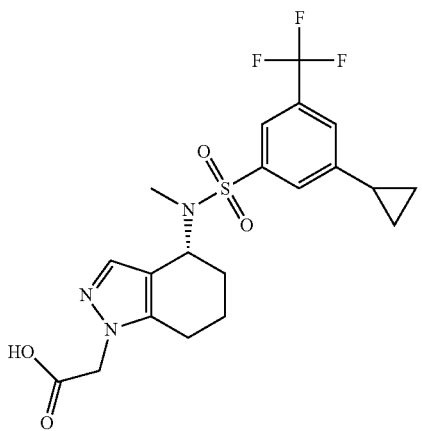

Starting with {(R)-4-[(3-cyclopropyl-5-trifluoromethyl-benzene-sulfonyl)-methyl-amino]-4,5,6,7-tetrahydro-indazol-1-yl}-acetic acid methyl ester (example 26-1) and using a method analogous to the procedure described for example 1-1a, {(R)-4-[(3-cyclopropyl-5-trifluoromethyl-benzene-sulfonyl)-methyl-amino]-4,5,6,7-tetrahydro-indazol-1-yl}-acetic acid methyl ester (24.5 mg, 83.2%) was obtained as a yellow solid. $^1$H NMR (400 MHz, CD$_3$OD) δ ppm 7.97 (s, 1H), 7.85 (s, 1H), 7.70 (s, 1H), 6.65 (s, 1H), 5.15 (q, 1H), 4.80 (s, 2H), 2.65 (s, 3 H), 2.50 (m, 2H), 2.20 (m, 1H), 2.00-1.73 (m, 4H), 1.15 (m, 2H), 0.85 (m, 2H). MS cald. for $C_{20}H_{22}F_3N_3O_4S$ 457, obsd. (ESI$^+$) [(M+H)$^+$] 458.

Activity and Use of the Compounds

The compounds of formula I possess valuable pharmacological properties. It has been found that said compounds are antagonists at the CRTH2 receptor and may be useful in treating diseases and disorders associated with that receptor such as asthma. The activity of the present compounds as CRTH2 receptor antagonists is demonstrated by the following biological assays.

Human CRTH2 Receptor Binding Assay

A whole cell receptor binding assay using [$^3$H]ramatroban as the competing radioactive ligand was employed to evaluate the compound binding activity to human CRTH2. The radioactive ligand [$^3$H]ramatroban was synthesized according to Sugimoto et. al. (*Eur. J. Pharmacol.* 524, 30-37, 2005) to a specific activity of 42 Ci/mmol A cell line stably expressing human CRTH2 was established by transfecting CHO-K1 cells with two mammalian expression vectors that harbored human CRTH2 and G-alpha16 cDNAs, respectively, using FuGene® 6 transfection reagent (from Roche). Stable clones expressing CRTH2 were selected by staining each clone with BM16 (BD Pharmingen™ from BD Biosciences, a division of Becton, Dickinson and Company), which is a rat monoclonal antibody to human CRTH2. The cells were maintained as monolayer cultures in Ham's F-12 medium containing 10% fetal bovine serum, 100 units/mL penicillin, 100 μg/mL streptomycin, 2 mM glutamine, 0.5 mg/mL G418 (geneticin) for CRTH2, and 0.2 mg/mL hygromycin-B (for G-alpha 16). For whole cell receptor binding assay, the monolayer cells were rinsed once with PBS (phosphate buffered saline), dissociated using ethylenediaminetetraacetate (Versene™ EDTA from Lonza Inc.), and suspended in PBS containing 10 mM MgCl$_2$ and 0.06% BSA (bovine serum albumin) at 1.5×10$^6$ cells/mL.

The binding reactions (0.2 mL) were performed in 96-well plates at room temperature in PBS containing 1.5×10$^5$ cells, 10 mM MgCl$_2$, 0.06% BSA, 20 nM [$^3$H]ramatroban, and test compound at various concentrations. After 1 hour of binding reactions, the cells were harvested on GF™/B filter microplates (microtiter plates with embedded glass fiber from PerkinElmer, Inc.) and washed 5 times with PBS using a Filtermate™ Harvester (a cell harvester that harvests and washes cells from microplates from PerkinElmer, Inc.). The radioactivities bound to the cells were determined using a microplate scintillation counter (TopCount® NXT, from PerkinElmer, Inc.) after adding 50 μL of Microscint™ 20 scintillation fluid (from PerkinElmer, Inc.) to each well of the filter plates. The radioactivity from non-specific binding was determined by replacing compound with 10 μM of 15(R)-15-methyl PGD$_2$ (from Cayman Chemical Company) in the reaction mixtures. The radioactivity bound to the cells in the absence of compound (total binding) was determined by replacing compound with 0.25% of DMSO (dimethyl sulfoxide) in the reaction mixture. Specific binding data were obtained by subtracting the radioactivity of non-specific binding from each binding data.

The IC$_{50}$ value is defined as the concentration of the tested compound that is required for 50% inhibition of total specific binding. In order to calculate the IC$_{50}$ value, the percent inhibition data were determined for 7 concentrations for each compound. The percent inhibition for a compound at each concentration was calculated according to the following formula, [1−(specific binding in the presence of compound)/(total specific binding)]×100. The IC$_{50}$ value was then obtained by fitting the percent inhibition data to a sigmoidal dose-response (4 parameter logistic) model in the XLfit® software Excel add-in program [from ID Business Solutions Ltd., model 205, where F(x)=(A+(B−A)/(1+((C/x)^D)))].

All the acid compounds of the foregoing examples were tested using the above Human CRTH2 Receptor Binding Assay (examples 1-1a to 1-18a, 2-1a to 2-8a, 3-1a to 3-4a, 4-1a to 4-4a, 5-1a, 6-1a, 7-1a, 7-2a, 8-1a, 9-1a, 10-1a to 10-7a, 11-1a, 12-1a, 13-1a, 14-1a, 15-1a, 16-1a, 17-1a, 18-1a, 19-1a, 20-1a, 21-1a, 22-1a, 23-1a, 24-1a to 24-4a, 25-1a to 25-3a, and 26-1a). The results of the assay showed that all of these compounds have binding activity exhibiting IC$_{50}$ values ranging from 0.0021 µM to 0.4307 µM. For instance, the following table shows the specific IC$_{50}$ values for some of these compounds:

| Example No. | Human CRTH2 Binding IC$_{50}$ (µM) |
|---|---|
| 1-1a | 0.013 |
| 1-2a | 0.3855 |
| 1-3a | 0.2341 |
| 1-4a | 0.0164 |
| 1-5a | 0.2248 |
| 1-6a | 0.397 |
| 1-7a | 0.0357 |
| 1-8a | 0.4307 |
| 1-9a | 0.2769 |
| 1-10a | 0.1194 |
| 1-11a | 0.2912 |
| 1-12a | 0.0533 |
| 1-13a | 0.205 |
| 1-14a | 0.0432 |
| 1-15a | 0.2624 |
| 1-16a | 0.0059 |
| 1-17a | 0.381 |
| 1-18a | 0.2639 |
| 2-1a | 0.0121 |
| 2-2a | 0.0978 |
| 2-3a | 0.0786 |
| 2-4a | 0.2531 |
| 2-5a | 0.0112 |
| 2-6a | 0.0502 |
| 2-7a | 0.1658 |
| 2-8a | 0.0434 |
| 3-1a | 0.1449 |
| 3-2a | 0.3695 |
| 3-3a | 0.0103 |
| 3-4a | 0.1942 |
| 4-1a | 0.0992 |
| 4-2a | 0.0391 |
| 4-3a | 0.0372 |
| 4-4a | 0.0539 |
| 5-1a | 0.0031 |
| 6-1a | 0.0025 |
| 7-1a | 0.0026 |
| 7-2a | 0.0029 |
| 8-1a | 0.0033 |
| 9-1a | 0.0126 |
| 10-1a | 0.0025 |
| 10-2a | 0.0029 |
| 10-3a | 0.0021 |
| 10-4a | 0.0047 |
| 10-5a | 0.0024 |
| 10-6a | 0.0033 |
| 10-7a | 0.0125 |
| 11-1a | 0.0078 |
| 12-1a | 0.022 |
| 13-1a | 0.0073 |
| 14-1a | 0.0062 |
| 15-1a | 0.0123 |
| 16-1a | 0.0698 |
| 17-1a | 0.0556 |
| 18-1a | 0.0286 |
| 19-1a | 0.007 |
| 20-1a | 0.0035 |
| 21-1a | 0.2775 |
| 22-1a | 0.0801 |
| 23-1a | 0.0395 |
| 24-1a | 0.0381 |
| 24-2a | 0.0457 |
| 24-3a | 0.0622 |
| 24-4a | 0.1461 |
| 25-1a | 0.022 |
| 25-2a | 0.1424 |
| 25-3a | 0.0404 |
| 26-1a | 0.0163 |

Calcium Flux Assay Using Fluorometric Imaging Plate Reader (FLIPR)

Cell Culture Conditions:

CHO-K1 cells previously transfected with G-alpha 16 were subsequently transfected with the human CRTH2 receptor and the neomycin resistance gene. Following selection in 800 µg/mL G418 (geneticin), individual clones were assayed for their receptor expression based on staining with an anti human CRTH2 IgG, followed by assaying for their response to 13,14-dihydro-15-keto Prostaglandin D$_2$ (DK-PDG$_2$) (ligand) in the Ca$^{2+}$ Flux assay. Positive clones were then cloned by limiting dilution cloning. The transfected cells were cultured in Ham's F-12 medium supplemented with 10% fetal bovine serum, 2 mM glutamine, 100 U/mL penicillin/100 µg/mL streptomycin, 200 µg/mL hygromycin B, and 800 µg/mL G418 (geneticin). Cells were harvested with trypsin-EDTA (trypsin-ethylenediaminetetraacetic acid) and counted using ViaCount® reagent (from Guava Technologies, Inc. which contains two DNA-binding dyes that enable the reagent user to distinguish between viable and non-viable cells). The cell suspension volume was adjusted to 2.5×10$^5$ cells/mL with complete growth media. Aliquots of 50 µL were dispensed into BD Falcon™ 384 well black/clear microplates (from BD Biosciences, a division of Becton, Dickinson and Company) and the microplates were placed in a 37° C. CO$_2$ incubator overnight. The following day, the microplates were used in the assay.

Dye Loading and Assay:

Loading Buffer containing dye (from the FLIPR® Calcium 3 Assay Kit from Molecular Devices, a division of MDS Analytical Technologies and MDS Inc.) was prepared by dissolving the contents of one bottle into 200 mL Hank's Balanced Salt Solution containing 20 mM HEPES (4-(2-hydroxyethyl)-1-piperazineethanesulfonic acid) and 2.5 mM probenecid. Growth media was removed from the cell plates and 25 µL of Hank's Balanced Salt Solution (HBSS) containing 20 mM HEPES, 0.05% BSA and 2.5 mM probenecid was added to each well followed by 25 µL of diluted dye using a Multidrop dispenser. The plates were then incubated for 1 hour at 37° C.

During the incubation, test compound plates were prepared by adding 90 µL of HBSS/20 mM HEPES/0.005% BSA buffer to the 2 μL of serial diluted compounds. To prepare serial diluted compounds, 20 mM stocks of compounds were dissolved in 100% DMSO. The compound dilution plate was set up as follows: well #1 received 5 μL of compound plus 10 μL of DMSO. Wells 2-10 received 10 μL of DMSO. 5 μL was mixed and transferred from well #1 into well #2. 1:3 serial dilutions were continued out 10 steps. 2 μL of diluted compound was transferred into duplicate wells of a 384 well "assay plate" and then 90 μL of buffer was added.

After incubation, both the cell and "assay plate" plates were brought to the fluorometric imaging plate reader (FLIPR®) and 20 μL of the diluted compounds were transferred to the cell plates by the FLIPR®. Plates were then incubated for 1 hour at room temperature. After the 1 hour incubation, plates were returned to the FLIPR® and 20 μL of 4.5× concentrated ligand was added to the cell plates. During the assay, fluorescence readings were taken simultaneously from all 384 wells of the cell plate every 1.5 seconds. Five readings were taken to establish a stable baseline, then 20 μL of sample was rapidly (30 μL/sec) and simultaneously added to each well of the cell plate. The fluorescence was continuously monitored before, during and after sample addition for a total elapsed time of 100 seconds. Responses (increase in peak fluorescence) in each well following agonist addition were determined. The initial fluorescence reading from each well, prior to ligand stimulation, was used as a zero baseline value for the data from that well. The responses were expressed as % inhibition of the buffer control. The $IC_{50}$ value, defined as the concentration of a compound that was required for 50% inhibition of the buffer control, was calculated by fitting the percent inhibition data for 10 concentrations to a sigmoidal dose-response (4 parameter logistic) model using Genedata Screener® Condoseo software program [from Genedata AG, model 205, where $F(x)=(A+(B-A)/(1+((C/x)^D)))$].

Representative compounds tested in the binding assay were tested using the above FLIPR® assay. The results of the FLIPR® assay showed that all of the representative compounds tested in this assay have activity exhibiting $IC_{50}$ values ranging from 0.0003 μM to 34.815 μM.

DK-PGD$_2$-Induced IL-13 Production Assay in Th2 Cells

Inhibition of 13,14-dihydro-15-keto Prostaglandin D$_2$ (DK-PGD$_2$)-induced IL-13 production in T helper type 2 (Th2) cells was applied to evaluate compound cellular potency.

Cultures of Th2 cells were established from blood of healthy human volunteers according to the following procedure. Peripheral blood mononuclear cells (PBMC) were first isolated from 50 mL of fresh blood by Ficoll-Hypaque density gradient centrifugation, followed by CD4$^+$ cell purification using a CD4$^+$ T Cell Isolation Kit II (from Miltenyi Biotec Inc.). The CD4$^+$ T cells were then differentiated to Th2 cells by culturing the cells in X-VIVO 15® medium (from Cambrex BioScience Walkersville Inc.) containing 10% human AB serum (serum of blood type AB from Invitrogen Corporation), 50 U/mL of recombinant human interleukin-2 (rhIL-2) (from PeproTech Inc.) and 100 ng/mL of recombinant human interleukin-4 (rhIL-4) (from PeproTech Inc.) for 7 days. The Th2 cells were isolated using a CD294 (CRTH2) MicroBead Kit (from Miltenyi Biotec Inc.) and amplified in X-VIVO 15® medium containing 10% human AB serum and 50 U/mL of rhIL-2 for 2 to 5 weeks. In general, 70% to 80% of the Th2 cells used in the assay are CRTH2-positive when analyzed by fluorescence-activated cell sorting using the BM16 antibody (as previously described) conjugated to phycoerythrin (PE).

To determine cellular inhibitory potency, compounds at various concentrations were incubated with $2.5 \times 10^4$ Th2 cells and 500 nM DK-PGD$_2$ for 4 hrs at 37° C. in 200 μL of X-VIVO 15® medium containing 10% human AB serum. IL-13 production to the medium was detected by ELISA (enzyme-linked immunosorbent assay) using an "Instant ELISA™" kit (from Bender MedSystems Inc.) according to the procedure suggested by the vendor. The spontaneous production of IL-13 by Th2 cells was determined in the absence of DK-PGD2 stimulation and the value was subtracted from that in the presence of each compound for percent inhibition and $IC_{50}$ calculations.

The percent inhibition of interleukin 13 (IL-13) production for a compound at various concentrations was calculated according to the following formula, $[1-(IL-13 \text{ production in the presence of compound})/(IL-13 \text{ production in the presence of 0.15\% DMSO})]_{\times 100}$. The $IC_{50}$ value, defined as the concentration of a compound that is required for 50% inhibition of IL-13 production, was calculated by fitting the percent inhibition data for 7 concentrations to a sigmoidal dose-response (4 parameter logistic) model in the XLfit® software Excel add-in program [ID Business Solutions Ltd., model 205, where $F(x)=(A+(B-A)/(1+((C/x)^D)))$].

Representative compounds tested in the binding assay were tested using the foregoing DK-PGD$_2$-induced IL-13 production assay. The results of the DK-PGD$_2$-induced IL-13 production assay showed that all of the representative compounds tested in this assay have activity in inhibiting IL-13 production, exhibiting $IC_{50}$ values ranging from 0.0003 μM to 0.309 μM.

Thus, the compounds of the present invention possess a specific, substantial and credible utility since the compounds tested show some activity in at least one of the above three assays (i.e., binding at the CRTH2 receptor), and therefore may be useful as antagonists in treating diseases and disorders associated with this receptor such as asthma.

In one embodiment, the present invention relates to a method for the treatment and/or prevention of diseases and disorders which are associated with the modulation of CRTH2 receptors, which method comprises administering a therapeutically effective amount of a compound of formula I to a human being or animal. A method for the treatment and/or prevention of an inflammatory or allergic disease or disorder is preferred. Such diseases or disorders may include (but are not limited to) asthma, chronic obstructive pulmonary disease (COPD), allergic inflammation, allergic rhinitis, and atopic dermatitis.

The present invention is also directed to the administration of a therapeutically effective amount of a compound of formula I in combination or association with other drugs or active agents for the treatment of inflammatory or allergic diseases and disorders. In one embodiment, the present invention relates to a method for the treatment and/or prevention of such diseases or disorders comprising administering to a human or animal simultaneously, sequentially, or separately, a therapeutically effective amount of a compound of formula I and another drug or active agent (such as another anti-inflammatory or anti-allergic drug or agent). These other drugs or active agents may have the same, similar, or a completely different mode of action. Suitable other drugs or active agents may include, but are not limited to: Beta2-adrenergic agonists such as albuterol or salmeterol; corticosteroids such as dexamethasone or fluticasone; antihistamines such as loratidine; leukotriene antagonists such as montelukast or zafirlukast; anti-IgE antibody therapies such as omalizumab; anti-infectives such as fusidic acid (particularly for the treatment of atopic dermatitis); anti-fungals such as clotrimazole (particularly for the treatment of atopic dermatitis); immunosuppressants such as tacrolimus and pimecrolimus; other antagonists of PGD2 acting at other receptors such as DP antagonists; inhibitors of phoshodiesterase type 4 such as cilomilast; drugs that modulate cytokine production such as inhibitors of TNF-alpha converting enzyme (TACE); drugs that modulate the activity of Th2 cytokines IL-4 and IL-5 such as blocking monoclonal antibodies and soluble receptors; PPAR-gamma agonists such as rosiglitazone; and 5-lipoxygenase inhibitors such as zileuton.

Unless stated to the contrary, all compounds in the examples were prepared and characterized as described. All patents and publications cited herein are hereby incorporated by reference in their entirety.

The invention claimed is:
1. A compound of formula I:

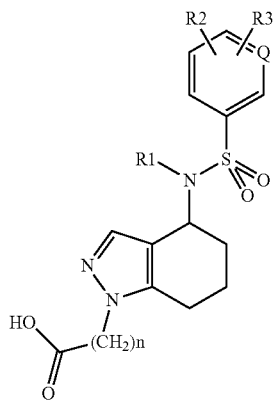

or a pharmaceutically acceptable salt or ester thereof; wherein:
Q is nitrogen,
R1 is hydrogen or lower alkyl optionally substituted by halogen;
R2 and R3 are bonded to the ring containing Q by substitution of a hydrogen atom of a ring carbon atom; and R2 and R3 are independently selected from the group consisting of:
(1) hydrogen;
(2) halogen;
(3) —NH$_2$;
(4) —NO$_2$;
(5) lower alkyl optionally substituted by halogen,
(6) lower cycloalkyl optionally substituted by lower alkyl;
(7) lower alkenyl;
(8) lower alkynyl;
(9) lower alkanoyl;
(10) lower alkoxy;
(11) lower cycloalkoxy;
(12) lower heterocycloalkyl;
(13) lower heterocycloalkyloxy;
(14) lower alkylsulfanyl, lower cycloalkylsulfanyl, or lower heterocycloalkylsulfanyl;
(15) lower alkylsulfinyl, lower cycloalkylsulfinyl, or lower heterocycloalkylsulfinyl;
(16) lower alkylsulfonyl, lower cycloalkylsulfonyl, or lower heterocycloalkylsulfonyl;
(17) lower alkylcarbonylamino;
(18) lower alkylsulfonylamino;
(19) lower dialkylamino; and
(20) lower trialkylsilyl;
wherein at least one of R2 or R3 is a moiety other than hydrogen; and
n is 1 or 2.
2. A compound of claim 1 which is an (R)-enantiomer.
3. A compound of claim 1 wherein R1 is hydrogen or unsubstituted lower alkyl.
4. A compound of claim 1 wherein R1 is hydrogen.
5. A compound of claim 1 wherein R1 is methyl.
6. A compound of claim 1 wherein n is 1.
7. A compound of claim 1 wherein R2 and R3 are independently selected from the group consisting of:
(1) halogen;
(2) lower alkyl optionally substituted by halogen,
(3) lower cycloalkyl optionally substituted by lower alkyl;
(4) lower alkenyl;
(5) lower alkynyl;
(6) lower alkanoyl;
(7) lower alkoxy;
(8) lower cycloalkoxy;
(9) lower alkylsulfonyl, lower cycloalkylsulfonyl, or lower heterocycloalkylsulfonyl;
(10) lower alkylcarbonylamino;
(11) lower alkylsulfonylamino;
(12) lower dialkylamino; and
(13) lower trialkylsilyl.
8. A compound of claim 1 wherein R2 and R3 are independently selected from the group consisting of:
(1) halogen;
(2) lower alkyl optionally substituted by halogen,
(3) lower cycloalkyl optionally substituted by lower alkyl;
(4) lower alkoxy;
(5) lower cycloalkoxy; and
(6) lower alkylsulfonyl or lower cycloalkylsulfonyl.
9. A compound of claim 1 wherein R2 and R3 are independently selected from the group consisting of:
(1) halogen;
(2) lower alkyl optionally substituted by halogen, and
(3) lower alkylsulfonyl or lower cycloalkylsulfonyl.
10. A compound of claim 1 wherein R2 and R3 are independently selected from the group consisting of trifluoromethyl, lower alkylsulfonyl and lower cycloalkylsulfonyl.
11. A compound of claim 1 wherein one of R2 or R3 is trifluoromethyl.
12. A compound of claim 1 wherein R2 and R3, independently of each other, are bonded to the ring containing Q at positions 3, 4 or 5 but not at the same position as each other.
13. A compound of claim 1 wherein one of R2 or R3 is bonded to position 3 and the other is bonded to position 5 on the ring containing Q.
14. A compound of claim 1 wherein one of R2 or R3 is bonded to position 3 and the other is bonded to position 5 on the ring containing Q, and at least one of R2 or R3 is trifluoromethyl.
15. A compound of claim 1 selected from the group consisting of:
[4-(5-Bromo-6-chloro-pyridine-3-sulfonylamino)-4,5,6,7-tetrahydro-indazol-1-yl]-acetic acid;
[4-(5-Bromo-6-ethoxy-pyridine-3-sulfonylamino)-4,5,6,7-tetrahydro-indazol-1-yl]-acetic acid; and
[4-(5-Bromo-6-cyclopentyloxy-pyridine-3-sulfonylamino)-4,5,6,7-tetrahydro-indazol-1-yl]-acetic acid.

16. A compound of claim 1 selected from the group consisting of:
- {(R)-4-[(5-Bromo-6-cyclobutoxy-pyridine-3-sulfonyl)-methyl-amino]-4,5,6,7-tetrahydro-indazol-1-yl}-acetic acid;
- {(R)-4-[(5-Bromo-6-isopropoxy-pyridine-3-sulfonyl)-methyl-amino]-4,5,6,7-tetrahydro-indazol-1-yl}-acetic acid; and
- ((R)-4-{[5-Bromo-6-(tetrahydro-pyran-4-yloxy)-pyridine-3-sulfonyl]-methyl-amino}-4,5,6,7-tetrahydro-indazol-1-yl)-acetic acid.

17. A pharmaceutically acceptable salt of a compound of claim 15.

18. A pharmaceutically acceptable salt of a compound of claim 16.

19. A compound of claim 1 selected from the group consisting of:
- [4-(5-Bromo-6-chloro-pyridine-3-sulfonylamino)-4,5,6,7-tetrahydro-indazol-1-yl]-acetic acid ethyl ester;
- [4-(5-Bromo-6-ethoxy-pyridine-3-sulfonylamino)-4,5,6,7-tetrahydro-indazol-1-yl]-acetic acid ethyl ester;
- [4-(5-Bromo-6-cyclopentyloxy-pyridine-3-sulfonylamino)-4,5,6,7-tetrahydro-indazol-1-yl]-acetic acid ethyl ester;
- {(R)-4-[(5-Bromo-6-cyclobutoxy-pyridine-3-sulfonyl)-methyl-amino]-4,5,6,7-tetrahydro-indazol-1-yl}-acetic acid ethyl ester;
- {(R)-4-[(5-Bromo-6-isopropoxy-pyridine-3-sulfonyl)-methyl-amino]-4,5,6,7-tetrahydro-indazol-1-yl}-acetic acid ethyl ester; and
- ((R)-4-{[5-Bromo-6-(tetrahydro-pyran-4-yloxy)-pyridine-3-sulfonyl]-methyl-amino}-4,5,6,7-tetrahydro-indazol-1-yl)-acetic acid ethyl ester.

20. A pharmaceutical composition comprising a therapeutically effective amount of a compound according to claim 1 and a pharmaceutically acceptable carrier.

* * * * *